United States Patent
Sarkorov et al.

(10) Patent No.: US 12,102,797 B2
(45) Date of Patent: Oct. 1, 2024

(54) AUTOMATIC INJECTION DEVICE WITH A DAMPENING ELEMENT

(71) Applicant: E3D A.C.A.L LTD, Merom Hagalil (IL)

(72) Inventors: Dmitri Sarkorov, Rama Gan (IL); David Daily, Herzliya (IL); Lior Raday, Kibbutz Bror Hail (IL)

(73) Assignee: E3D A.C.A.L LTD, Merom Hagalil (IL)

( * ) Notice: Subject to any disclaimer, the term of this patent is extended or adjusted under 35 U.S.C. 154(b) by 334 days.

(21) Appl. No.: 17/329,775

(22) Filed: May 25, 2021

(65) Prior Publication Data

US 2021/0275744 A1    Sep. 9, 2021

Related U.S. Application Data

(63) Continuation of application No. 16/298,283, filed on Mar. 11, 2019, now Pat. No. 11,040,142.

(60) Provisional application No. 62/641,985, filed on Mar. 12, 2018.

(51) Int. Cl.
*A61M 5/20* (2006.01)
*A61M 5/24* (2006.01)
(Continued)

(52) U.S. Cl.
CPC ............ *A61M 5/20* (2013.01); *A61M 5/2033* (2013.01); *A61M 5/24* (2013.01);
(Continued)

(58) Field of Classification Search
CPC ............ A61M 2005/2086; A61M 5/20; A61M 5/2033
See application file for complete search history.

(56) References Cited

U.S. PATENT DOCUMENTS 5,578,015 A    11/1996 Robb
6,258,068 B1    7/2001 Kirchhofer et al.
(Continued)

FOREIGN PATENT DOCUMENTS

EP    0956875 B1    8/2005
EP    2218473 A1    8/2010
(Continued)

OTHER PUBLICATIONS

EP Application # 21155271.6 office action dated Nov. 27, 2023.
EP Application # 21155952.1 Search report dated Feb. 26, 2021.
IN Application # 201914009447 office action dated Dec. 1, 2023.

*Primary Examiner* — Deanna K Hall
(74) *Attorney, Agent, or Firm* — Sughrue Mion, PLLC

(57) ABSTRACT

An automatic injection device including a generally cylindrical syringe body having an opening, an outlet and an inner cylindrical surface adapted to contain an injectable liquid to be injected at an injection site via the outlet; a piston disposed in the cylindrical syringe body; a driving assembly, including an elongate plunger element having a forward end adapted to be axially inserted into the generally cylindrical syringe body and an at least partial forward sealing element mounted onto the elongate plunger element adjacent the forward end for creating an at least temporary slidable seal between the elongate plunger element and the inner cylindrical surface, whereby axial insertion of the elongate plunger element and the forward sealing element into the generally cylindrical syringe body creates friction between the forward sealing element and the inner cylindrical surface and also creates an at least temporary air spring between the forward sealing element and the piston, wherein the friction and the air spring dampen motion of the elongate plunger element.

15 Claims, 52 Drawing Sheets

(51) Int. Cl.
*A61M 5/315* (2006.01)
*A61M 5/32* (2006.01)
*A61M 5/46* (2006.01)

(52) U.S. Cl.
CPC ...... *A61M 5/31513* (2013.01); *A61M 5/3202* (2013.01); *A61M 5/3275* (2013.01); *A61M 5/46* (2013.01); *A61M 2005/202* (2013.01); *A61M 2005/208* (2013.01); *A61M 2005/2086* (2013.01); *A61M 2005/2407* (2013.01); *A61M 2005/2411* (2013.01); *A61M 2005/2492* (2013.01); *A61M 2205/42* (2013.01)

(56) References Cited

U.S. PATENT DOCUMENTS

| | | | |
|---|---|---|---|
| 7,128,728 | B2 | 10/2006 | Kirchhofer et al. |
| 7,357,791 | B2 | 4/2008 | Kirchhofer et al. |
| 7,931,625 | B2 | 4/2011 | Kirchhofer et al. |
| 7,931,626 | B2 | 4/2011 | Kirchhofer et al. |
| 8,398,593 | B2 | 3/2013 | Eich et al. |
| 2012/0191047 | A1* | 7/2012 | Raday .................. A61M 5/2033 604/198 |
| 2014/0364805 | A1 | 12/2014 | Llewellyn-Hyde et al. |
| 2015/0182691 | A1 | 7/2015 | McLoughlin et al. |
| 2019/0167906 | A1 | 6/2019 | Auld et al. |
| 2019/0275251 | A1 | 9/2019 | Sarkorov |

FOREIGN PATENT DOCUMENTS

| | | |
|---|---|---|
| WO | 2010146358 A2 | 12/2010 |
| WO | 2011012849 A1 | 2/2011 |
| WO | 2011032731 A1 | 3/2011 |
| WO | 2016055334 A1 | 4/2016 |
| WO | 2017/033193 A2 | 3/2017 |

* cited by examiner

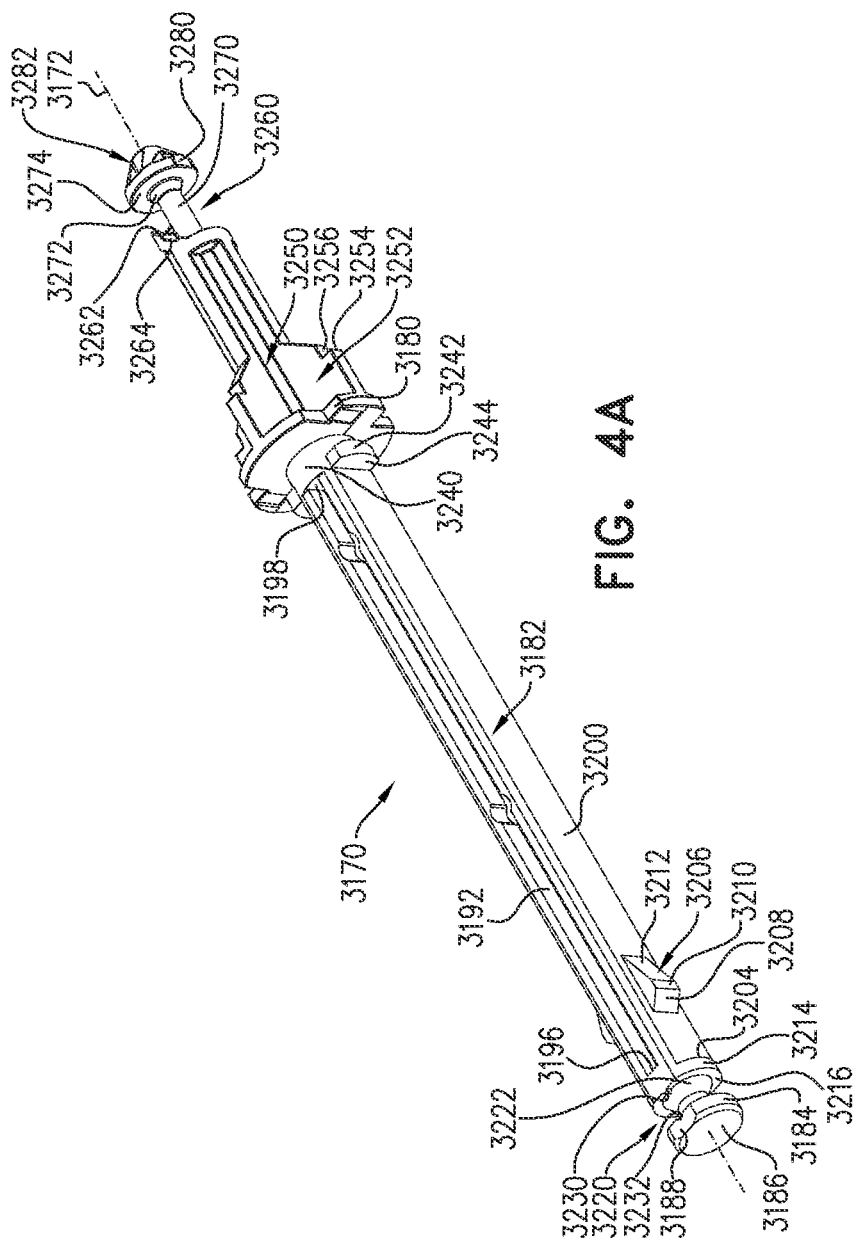

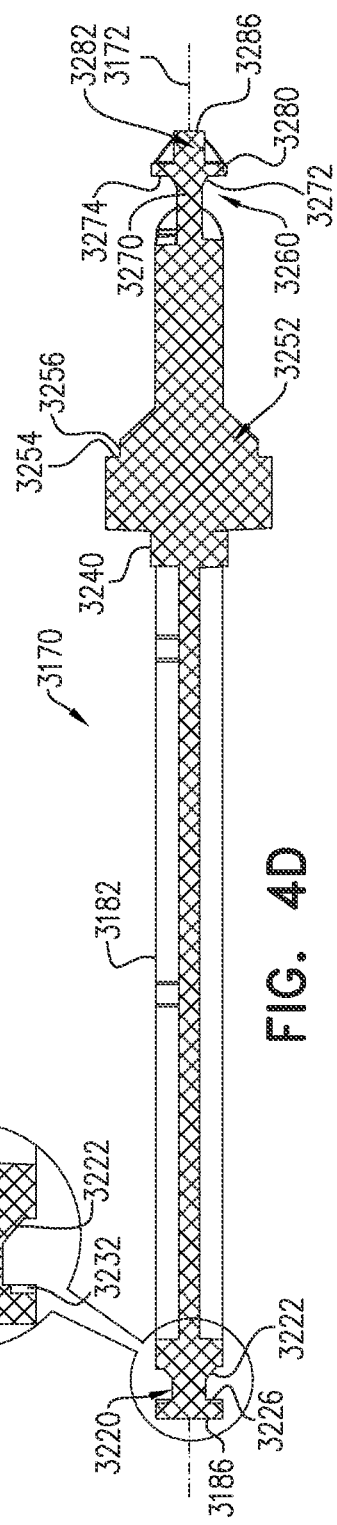
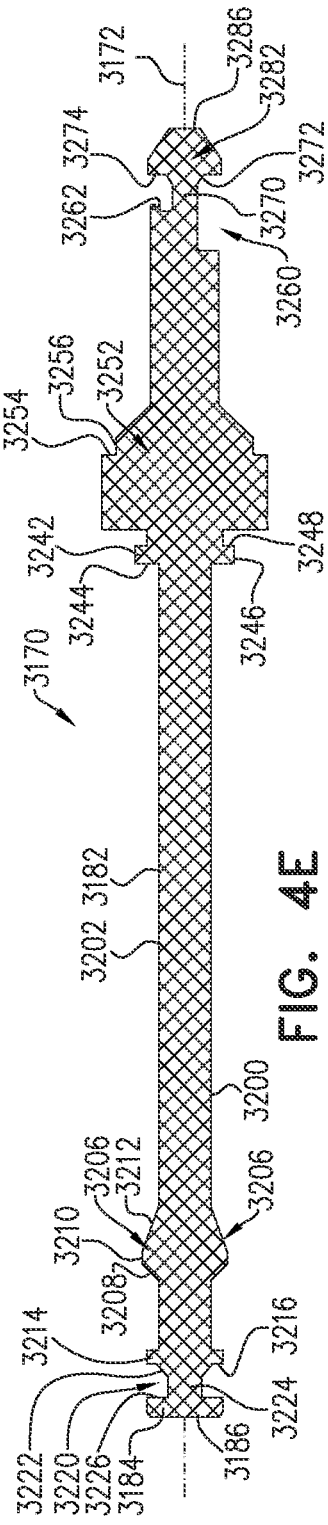
FIG. 4D
FIG. 4E

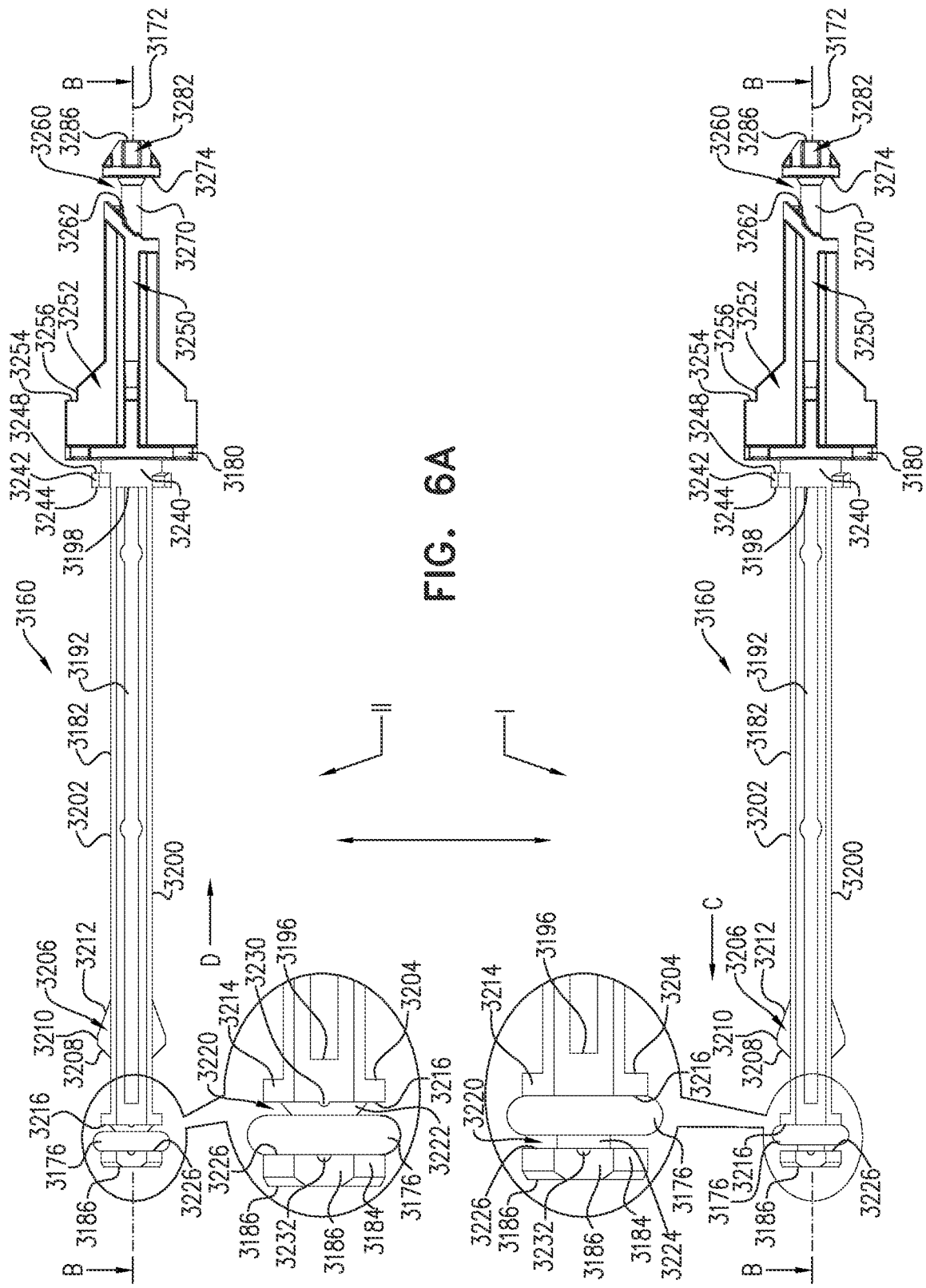

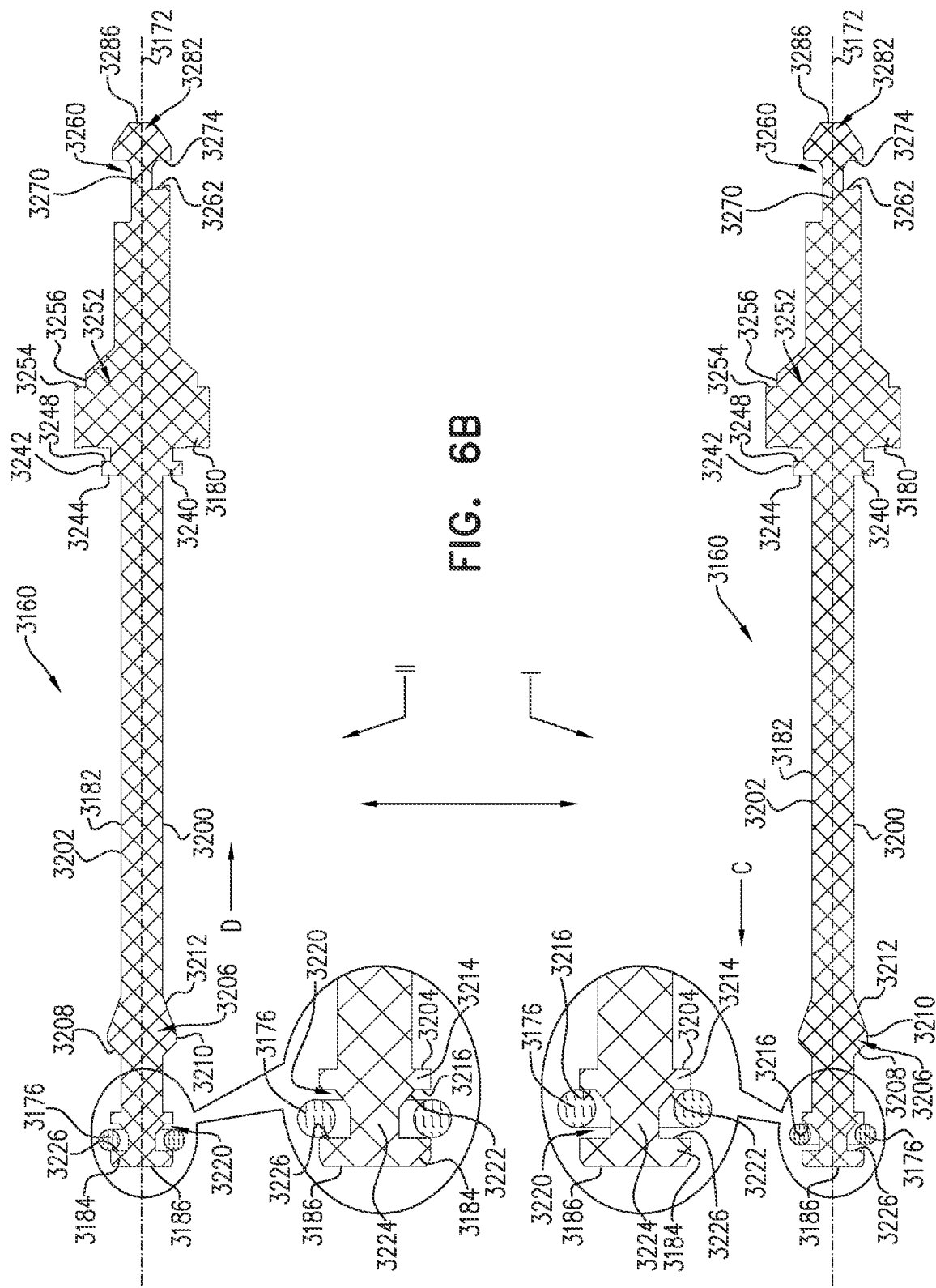

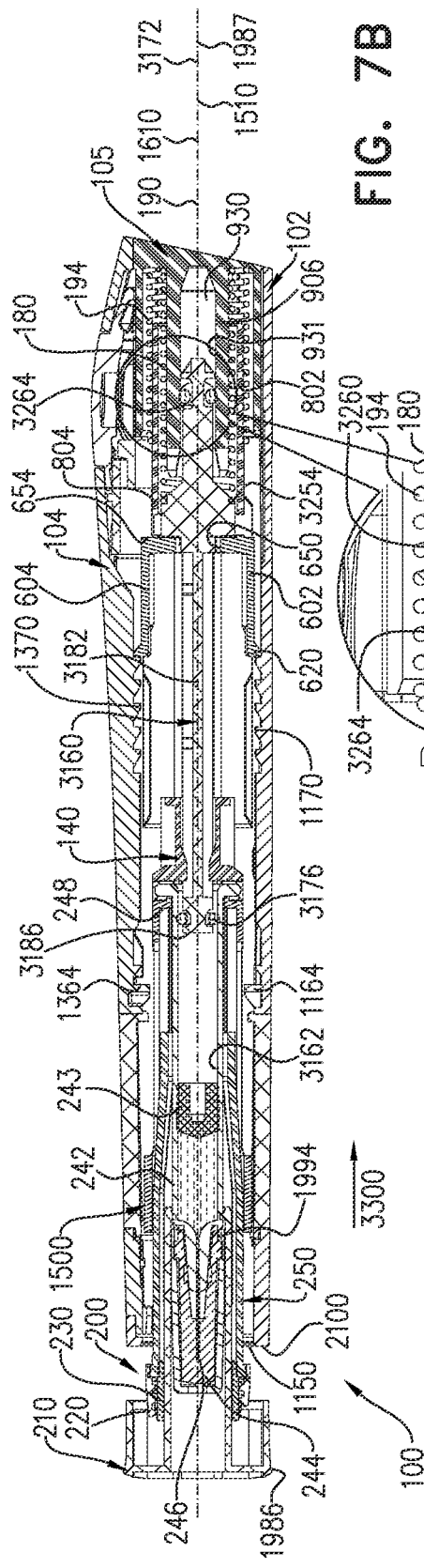
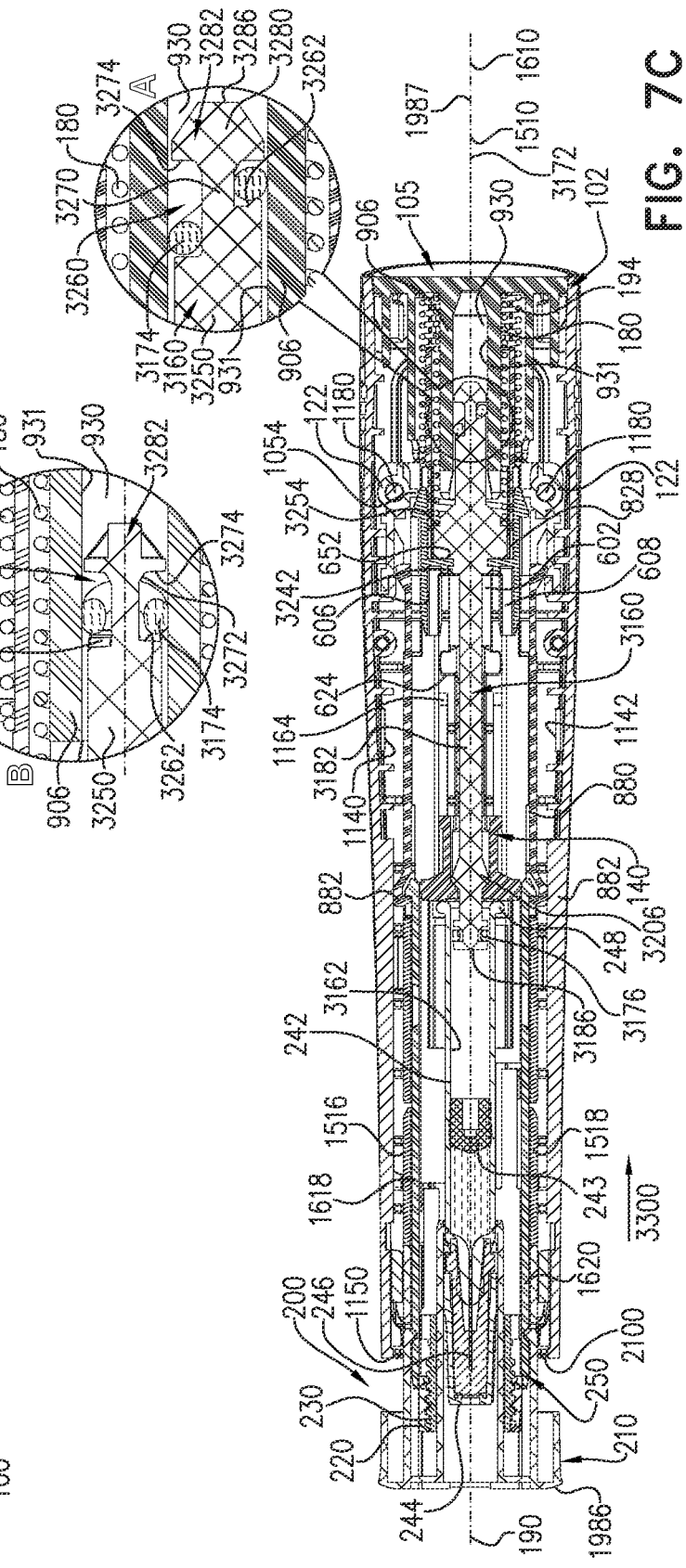

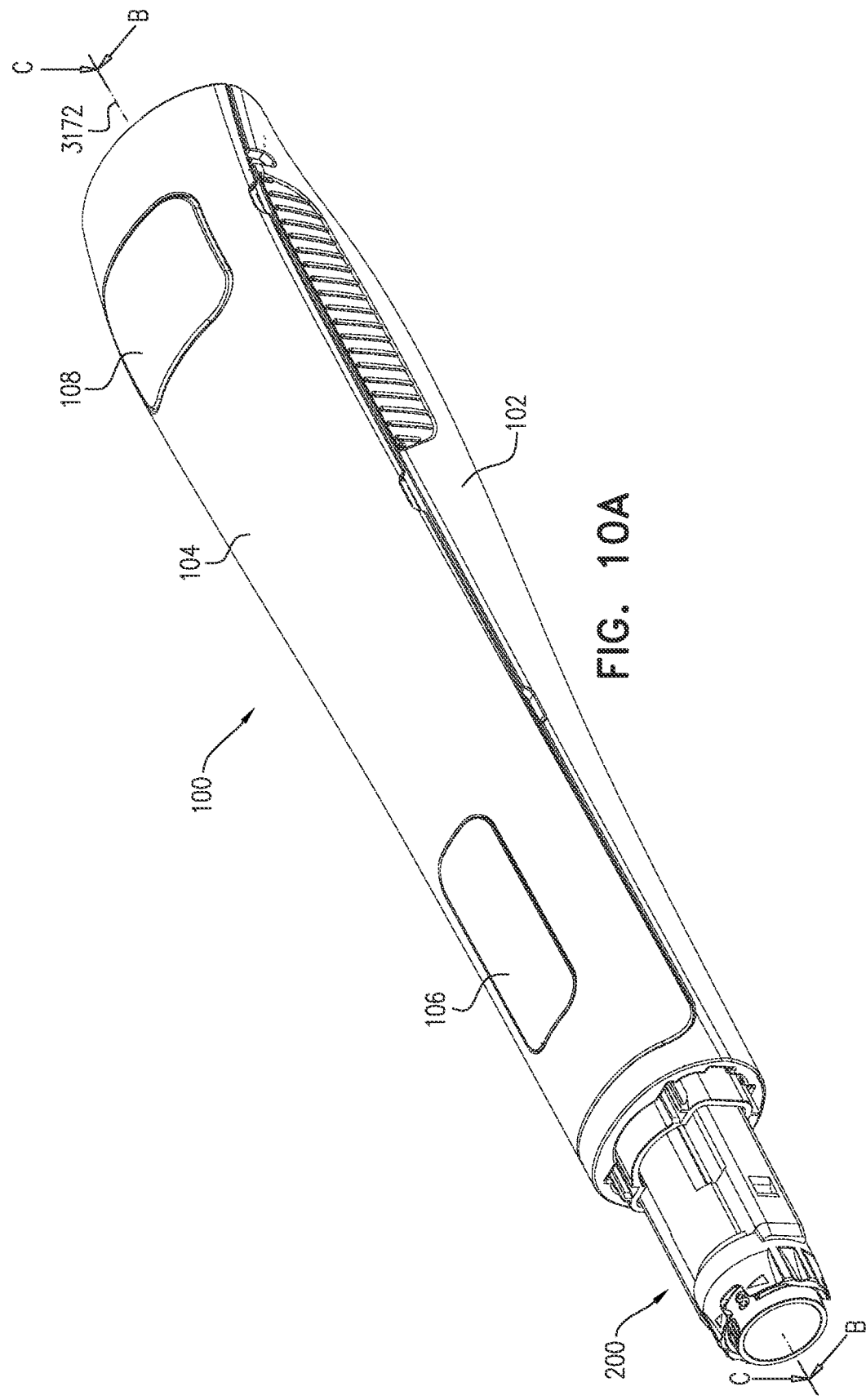

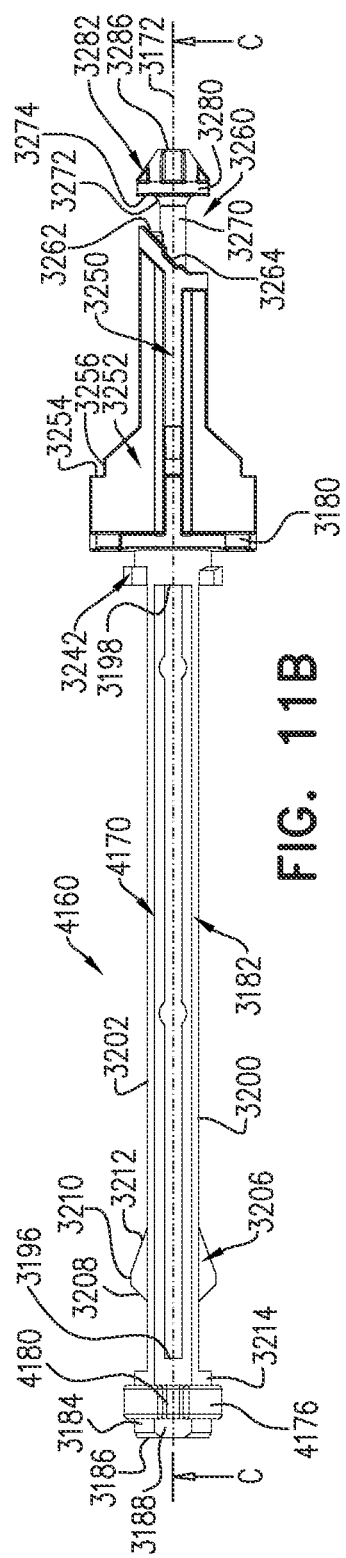
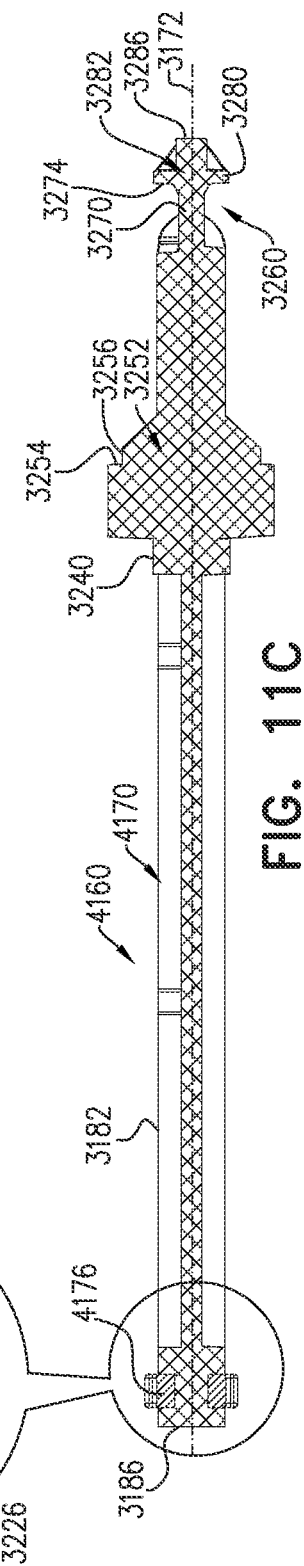

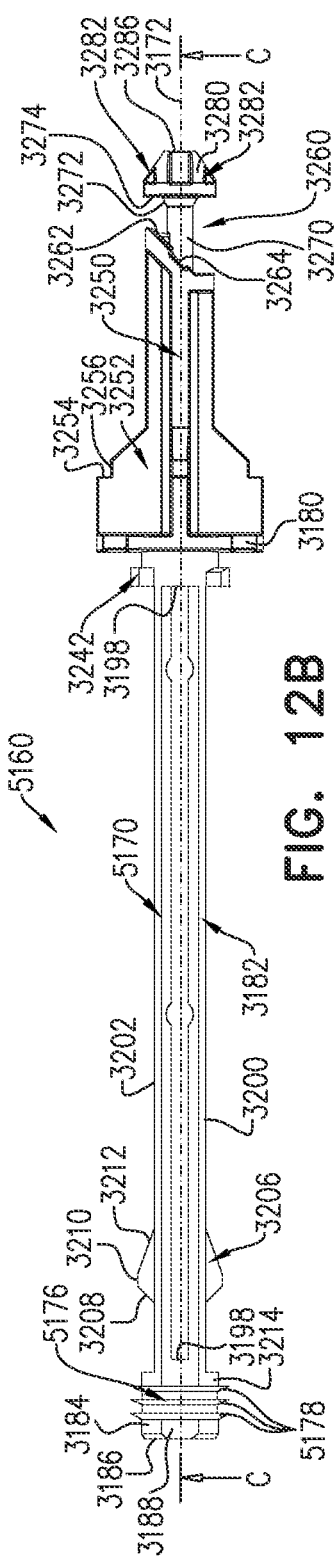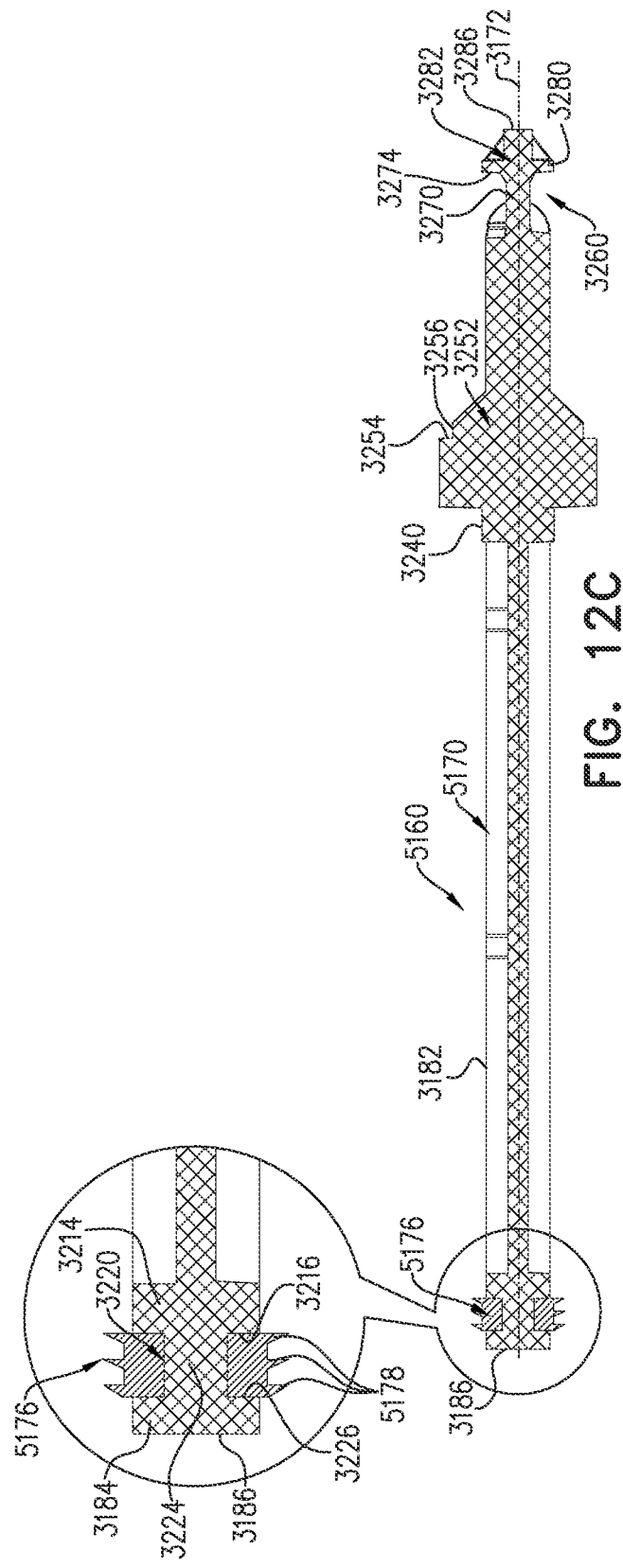

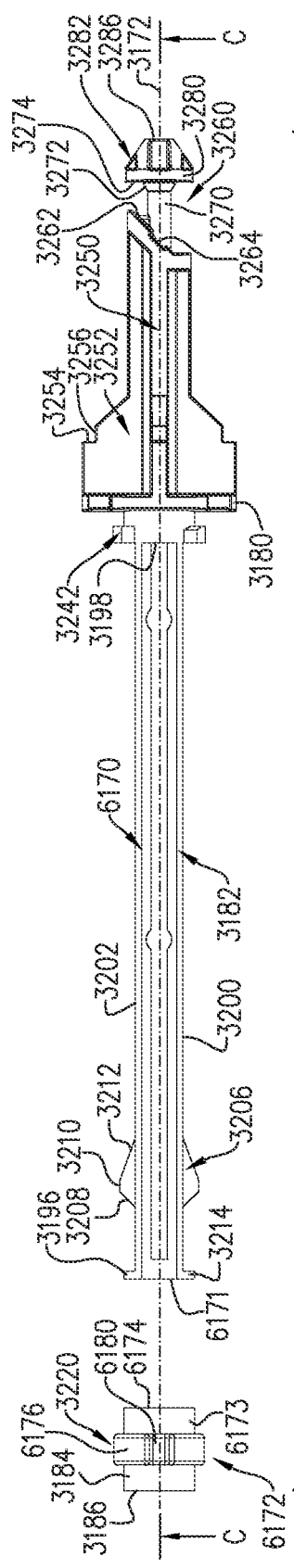
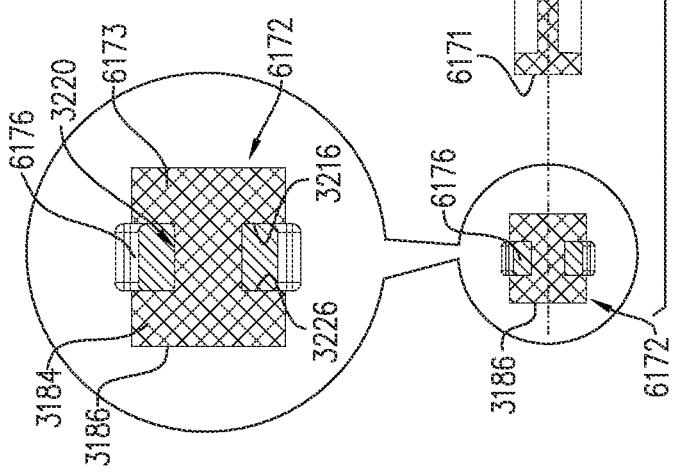
FIG. 13B
FIG. 13C

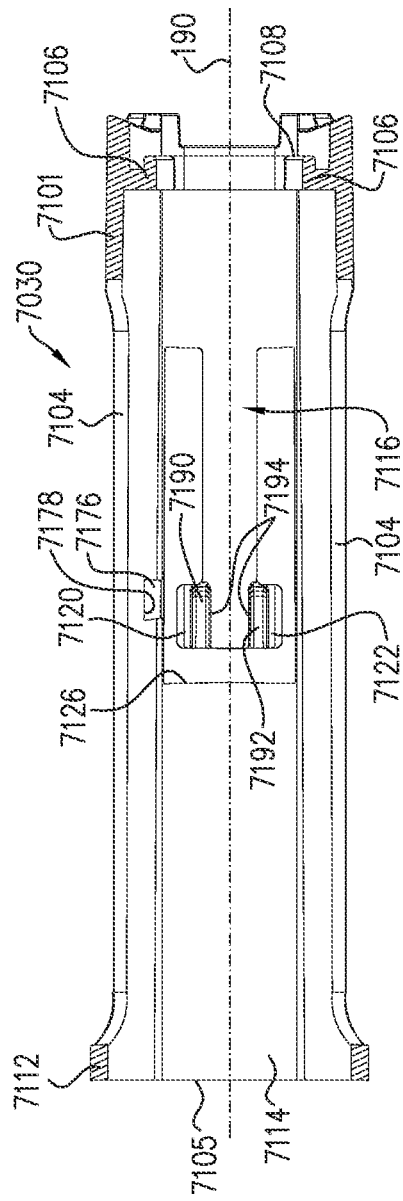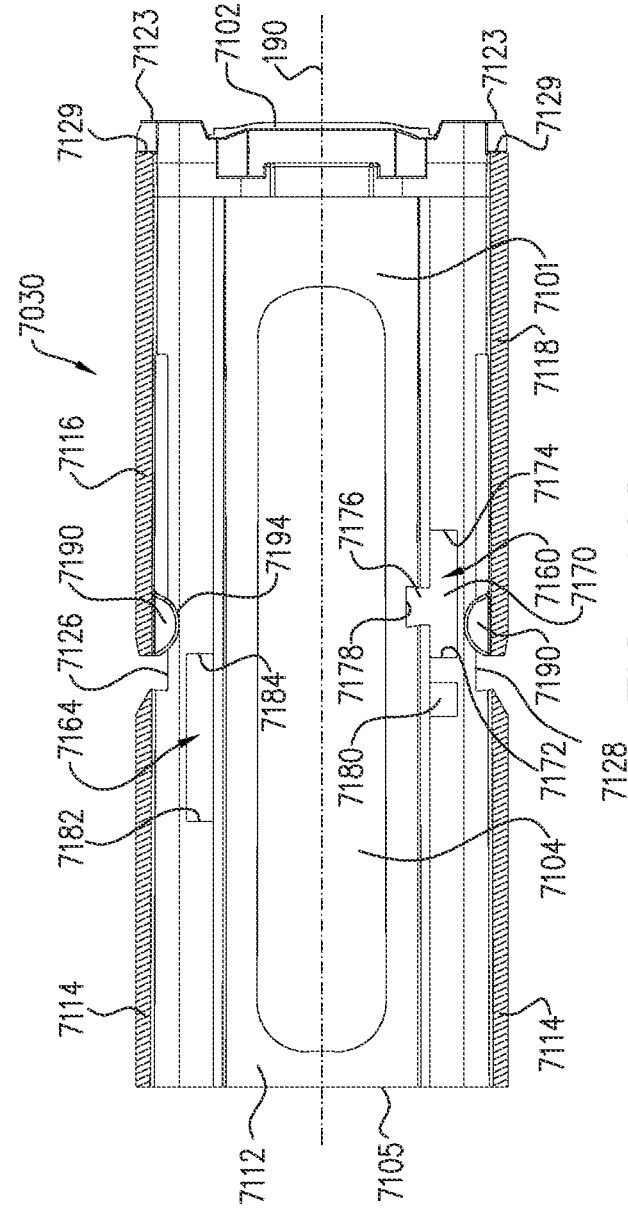

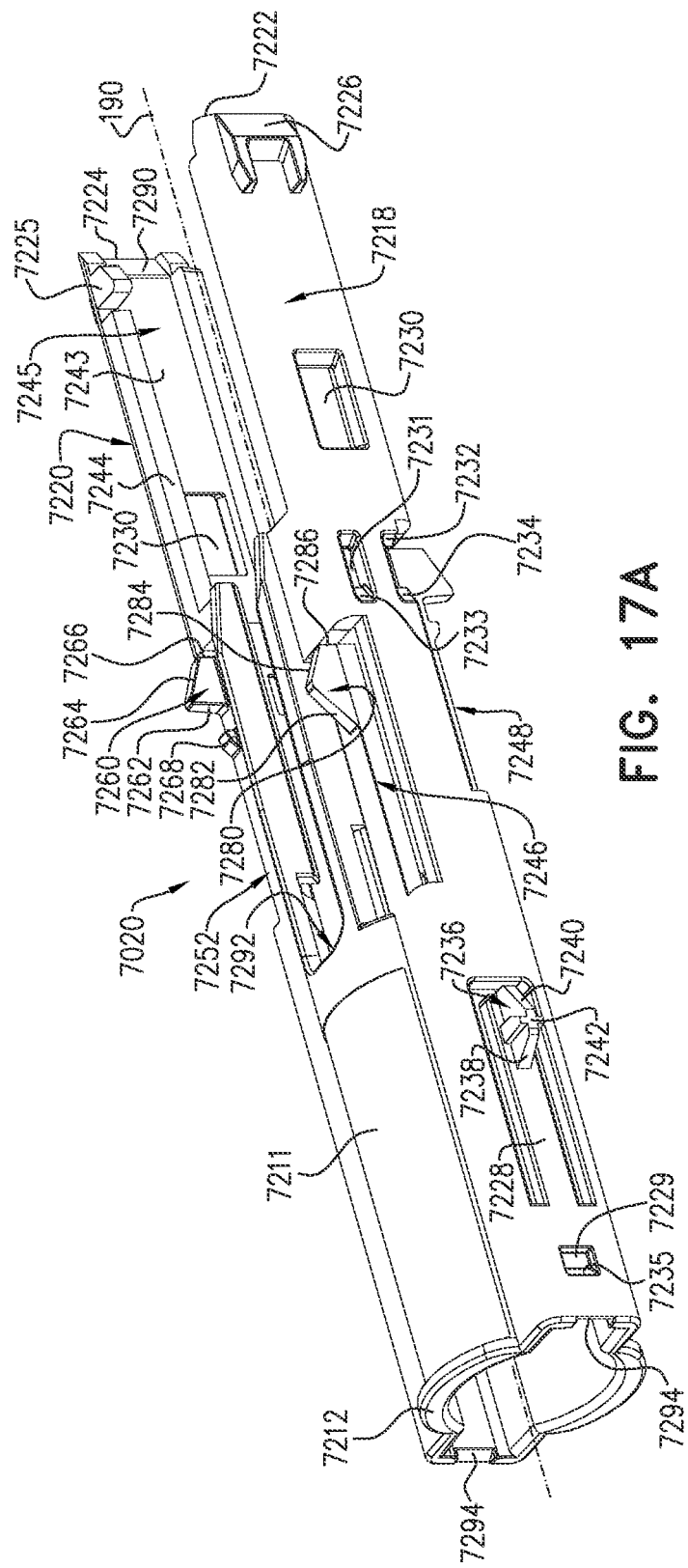

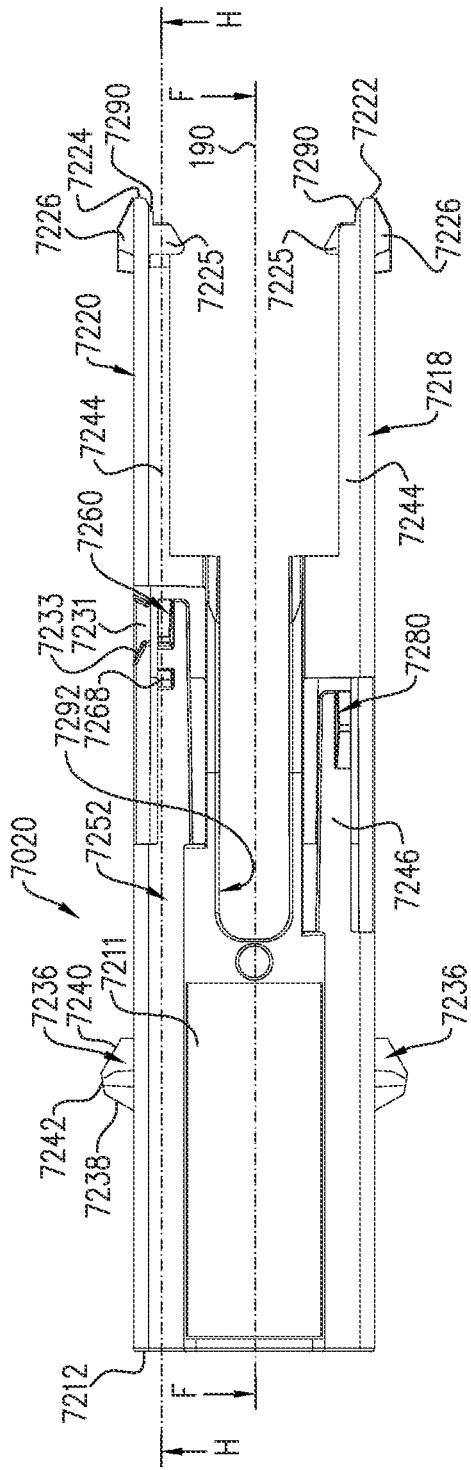
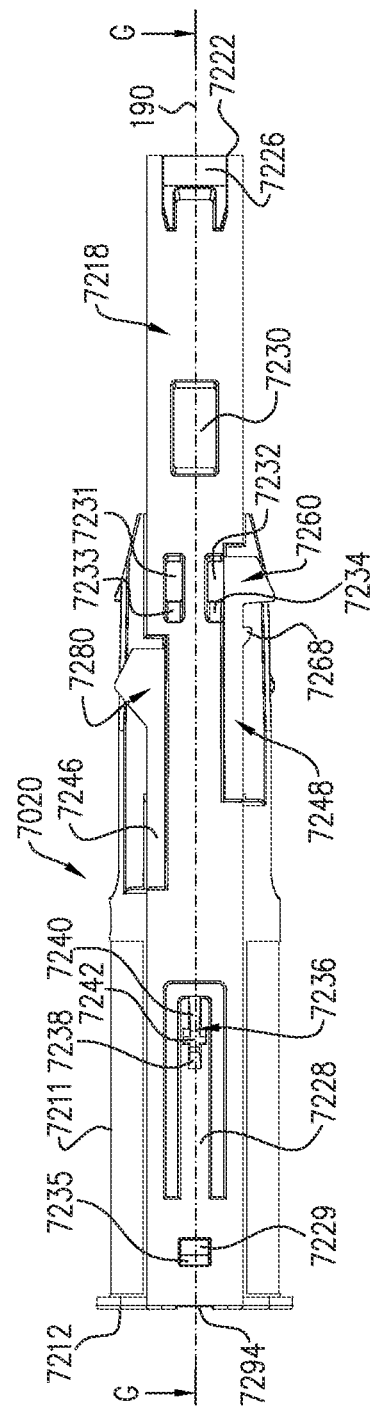
FIG. 17B
FIG. 17C

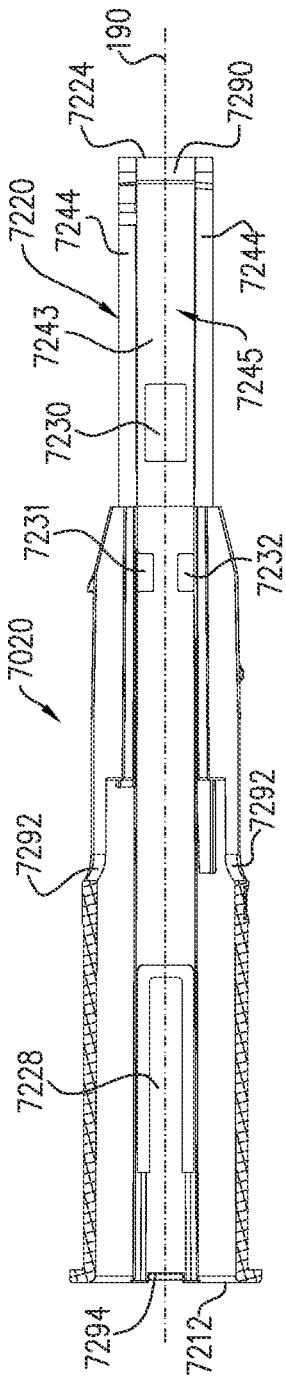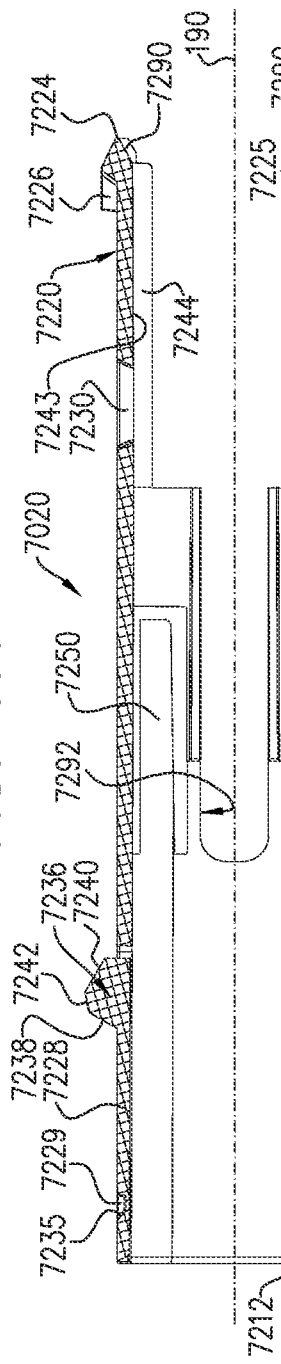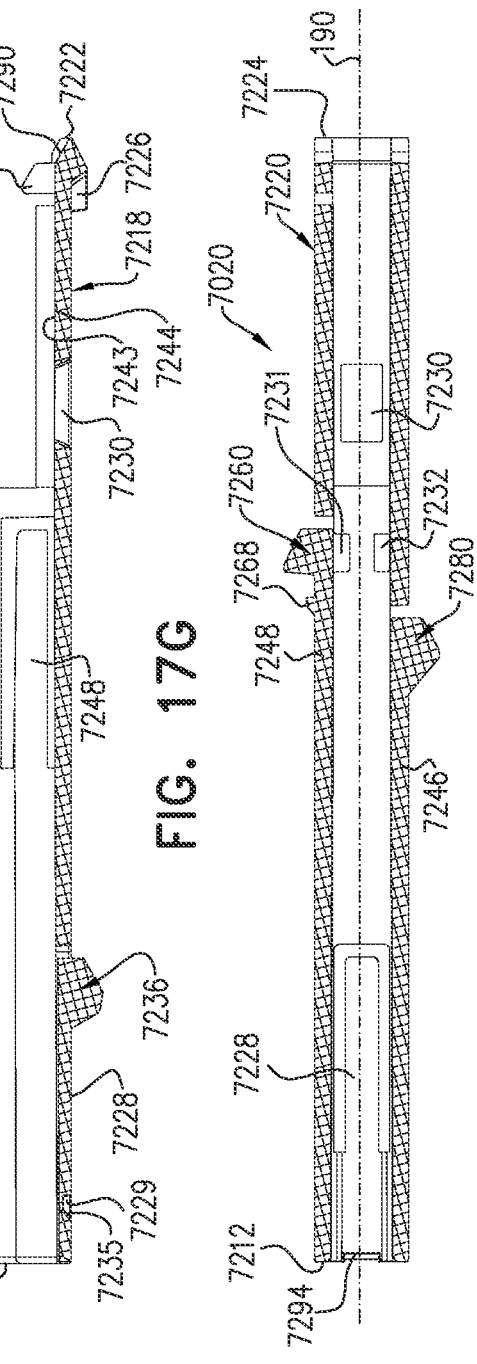

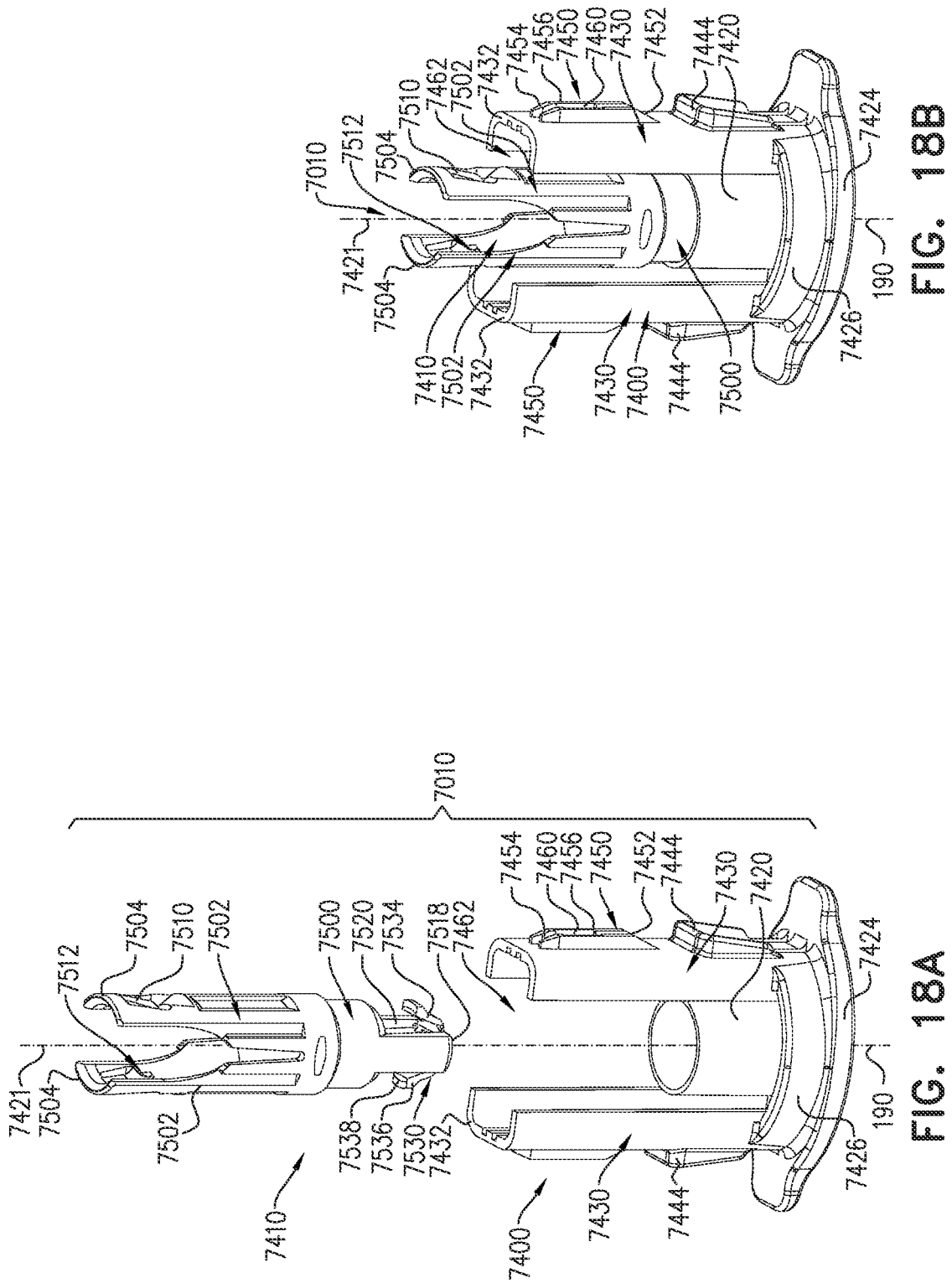

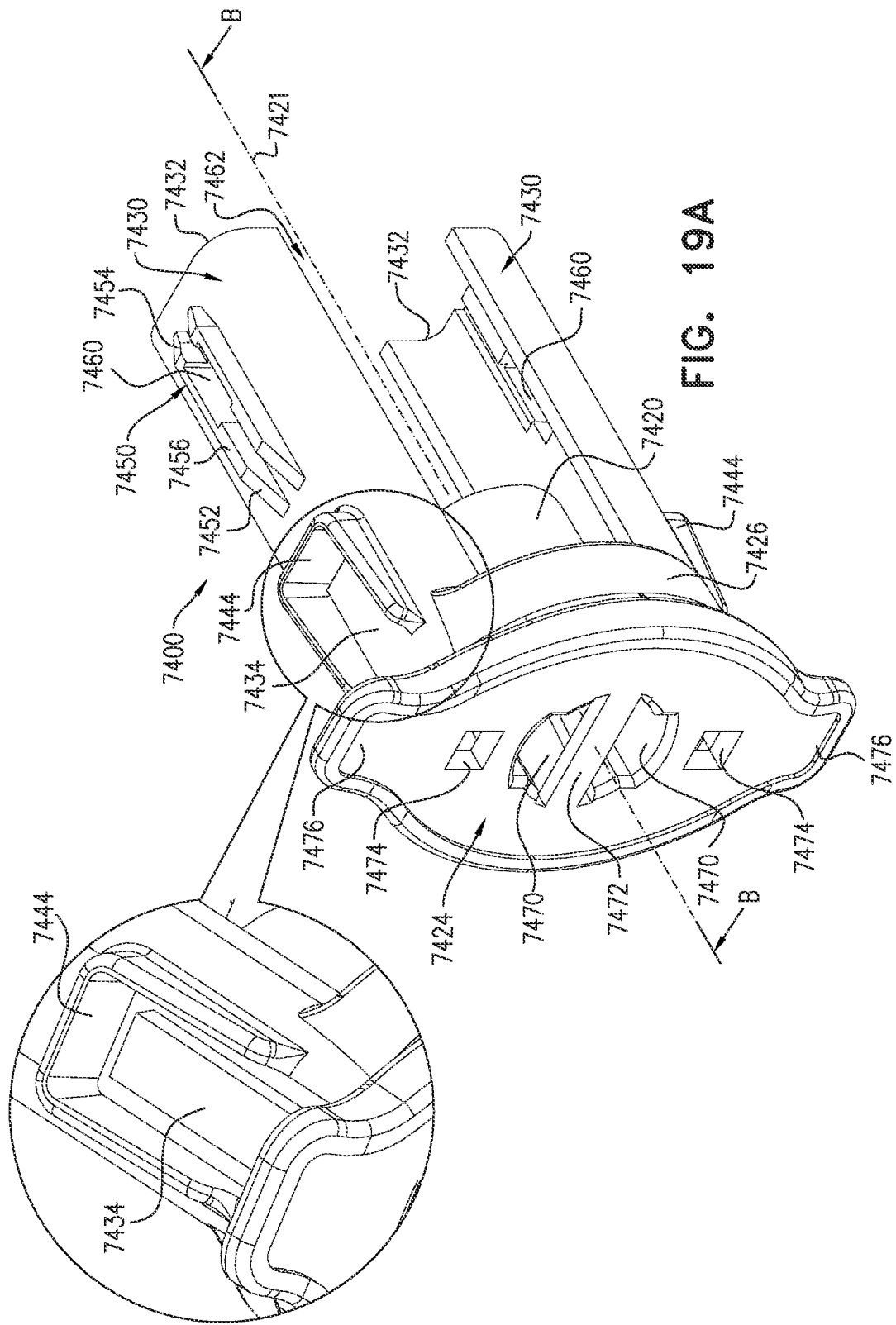

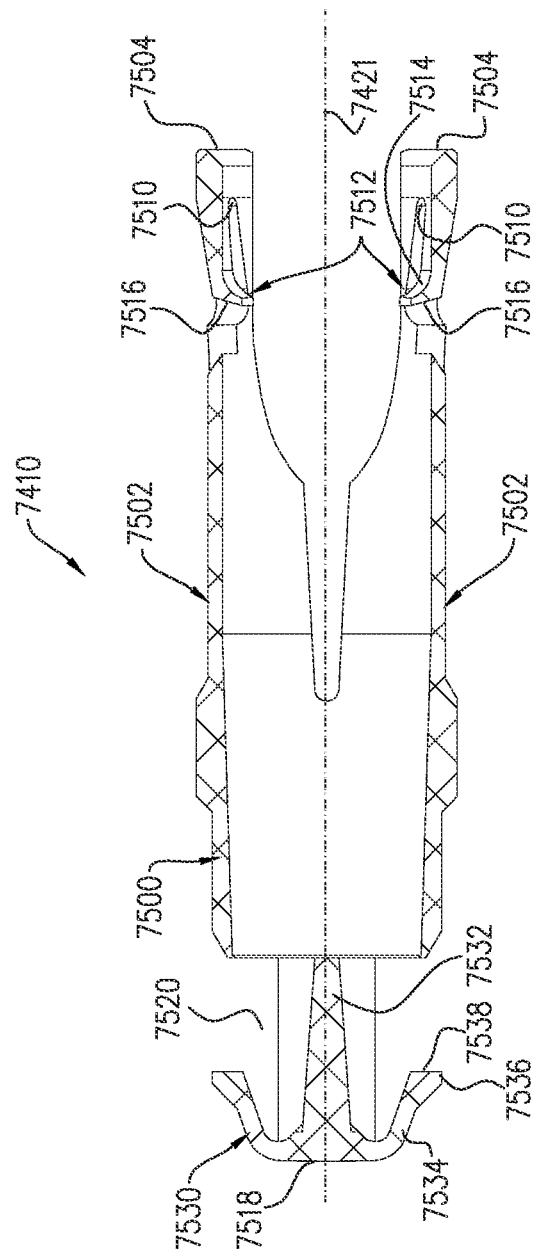

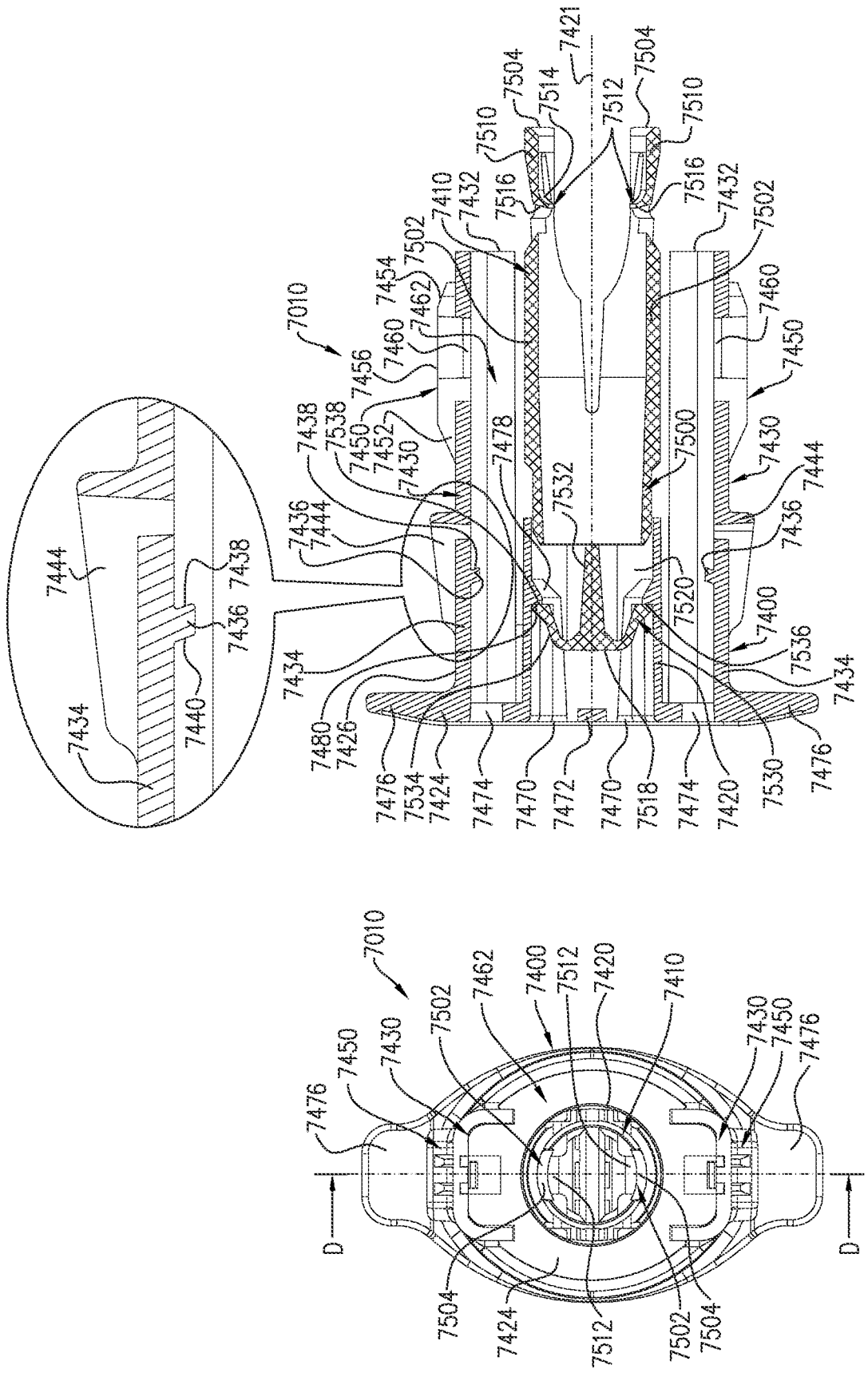

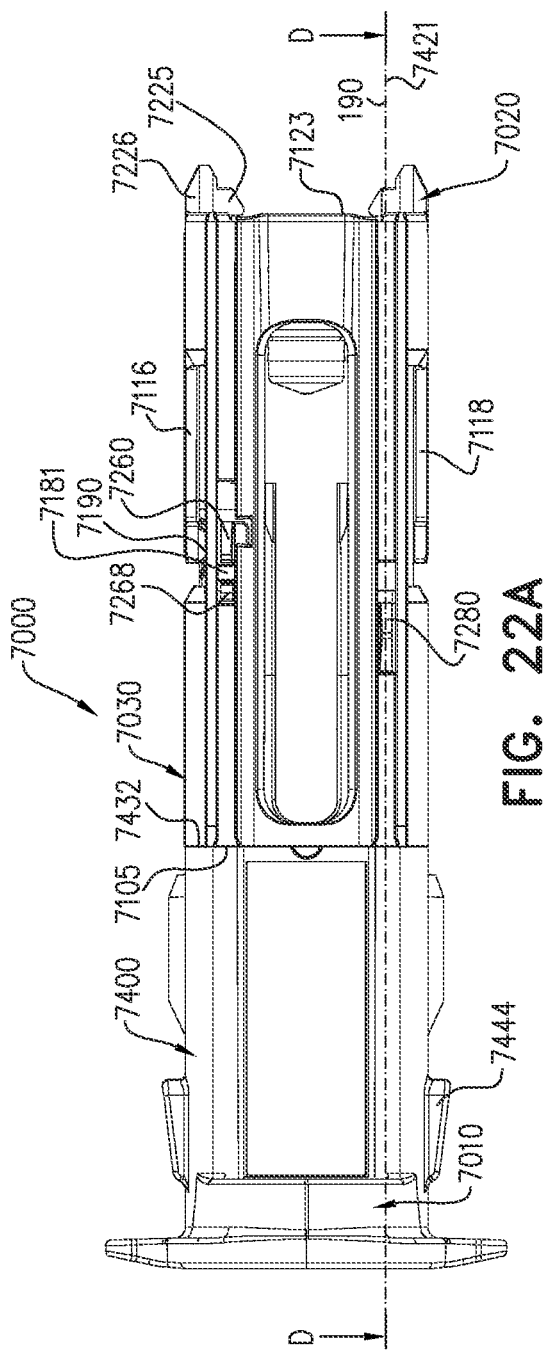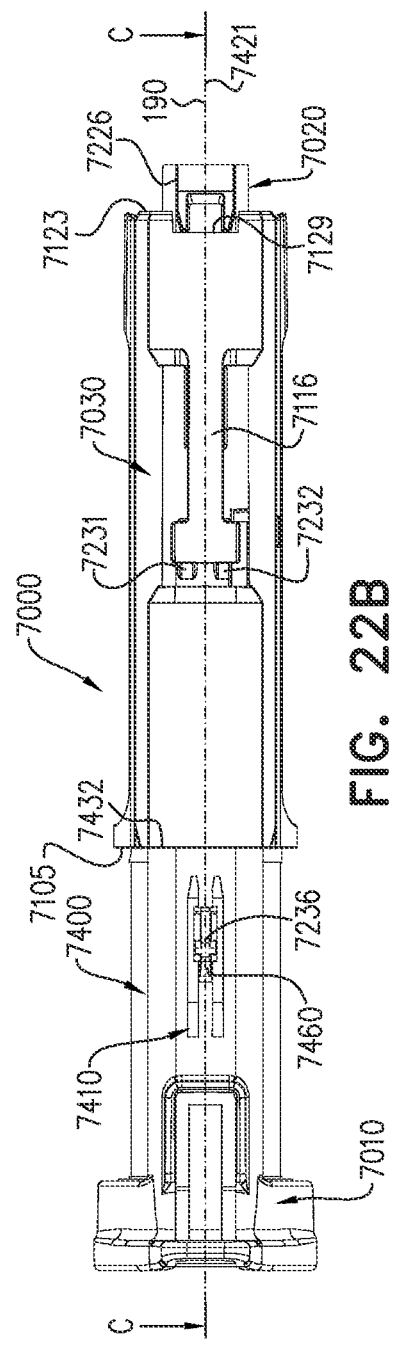

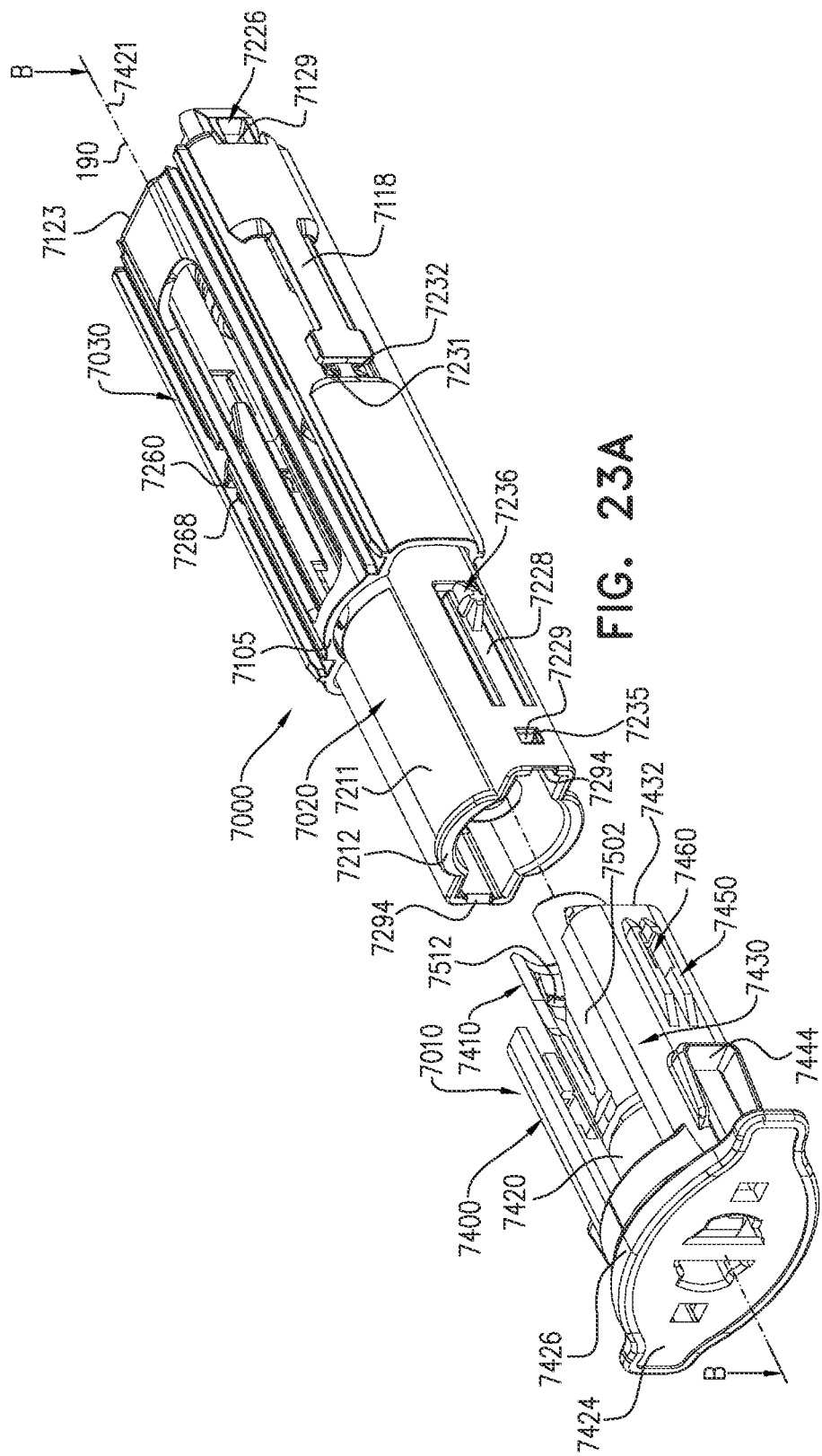

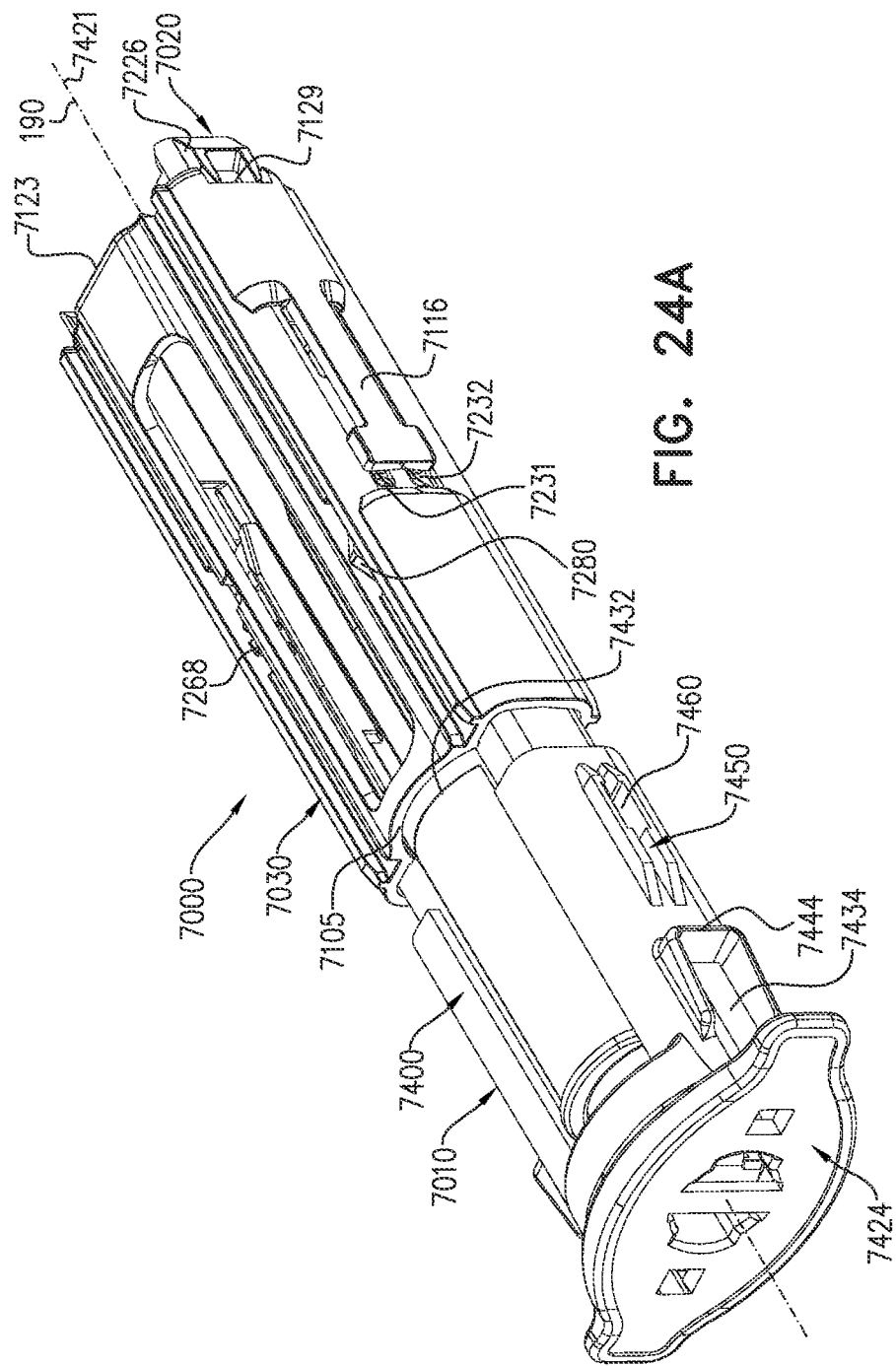

AUTOMATIC INJECTION DEVICE WITH A DAMPENING ELEMENT

REFERENCE TO RELATED APPLICATIONS

This is a Continuation application of U.S. application Ser. No. 16/298,283, filed Mar. 11, 2019, claiming priority based on U.S. Provisional application No. 62/641,985, filed Mar. 12, 2018, the contents of which are hereby incorporated by reference in their entireties.

FIELD OF THE INVENTION

The present invention generally relates to an auto injector, and more specifically to an auto injector adapted for parenteral administration of substances (e.g., a medication) to a living organism (human or animal).

BACKGROUND OF THE INVENTION

Many automatic injectors are known in the art. It is known that while using automatic injectors, there is a mechanical impact applied to a medicament container by a driving mechanism, this impact can damage the medicament container or cause spillage of the medicament contained therein. It is desired to provide a mechanism which prevents such damage to medicament container or spillage of medicament before activation of the automatic injector.

SUMMARY OF THE INVENTION

It is thus one object of the present invention to present a cost effective and safe auto-injector adapted for parenteral administration of substances to a patient, having a dampening mechanism incorporated therein.

The invention is further related to, but is not limited to a self-administration of patients with chronic diseases such as rheumatoid arthritis (RA), multiple sclerosis (MS), HIV, and growth hormone deficiency.

In accordance with an embodiment of the present invention, an automatic injection device including a generally cylindrical syringe body having an opening, an outlet and an inner cylindrical surface adapted to contain an injectable liquid to be injected at an injection site via the outlet; a piston disposed in the cylindrical syringe body; a driving assembly, including an elongate plunger element having a forward end adapted to be axially inserted into the generally cylindrical syringe body and an at least partial forward sealing element mounted onto the elongate plunger element adjacent the forward end for creating an at least temporary slidable seal between the elongate plunger element and the inner cylindrical surface, whereby axial insertion of the elongate plunger element and the forward sealing element into the generally cylindrical syringe body creates friction between the forward sealing element and the inner cylindrical surface and also creates an at least temporary air spring between the forward sealing element and the piston, wherein the friction and the air spring dampen motion of the elongate plunger element.

Preferably, the driving assembly, including a housing defining an axial travel path having an inner wall surface, the elongate plunger element extending along a longitudinal axis and having a rearward end arranged for axial travel along the axial travel path and defining a rearward sealing element seat and an at least partial rearward sealing element mounted onto the elongate plunger element at the rearward sealing element seat for creating an at least temporary slidable seal between the elongate plunger element and the inner wall surface.

Further preferably, the rearward sealing element seat having a rearward sealing element support which is generally perpendicular to the longitudinal axis and a forward sealing element support, facing the rearward sealing element but being angled with respect thereto and with respect to the longitudinal axis, thereby allowing the rearward sealing element to be axially tilted from an orientation perpendicular to the longitudinal axis upon rearward axial displacement of the plunger element causing at least partial disengagement of the rearward sealing element from the inner wall surface of the axial travel path.

Still further preferably, the forward sealing element is an O-ring. Yet further preferably, the rearward sealing element is an O-ring.

In accordance with an embodiment of the present invention, at least one forward sealing element seat is defined adjacent the forward end of the elongate plunger element. Preferably, the at least one forward sealing element seat includes a rearwardly-facing wall portion, a forwardly-facing wall portion facing the rearwardly-facing wall portion, a narrowed cylindrical axial portion extending therebetween and a forwardly-facing tapered wall portion formed adjacent the forwardly-facing wall portion. Further preferably, at least one protrusion is formed on the forwardly-facing wall portion and extends towards the forwardly-facing tapered wall portion. Still further preferably, the at least one rearwardly-facing wall portion has at least one slot formed therein.

Further in accordance with an embodiment of the present invention, upon forward axial displacement of the plunger element relative the syringe, the forward sealing element engages the forwardly-facing tapered wall portion, thereby providing for a relatively high level of damping of axial motion of the plunger element relative the syringe.

Preferably, the protrusion is configured to at least partially disable the air spring during forward axial displacement of the plunger element. Alternatively, the piston is displaced axially forwardly by the plunger element, without mechanical contact therebetween.

Further preferably, upon rearward axial displacement of the plunger element relative the syringe, the forward sealing element engages the rearwardly-facing wall portion, thereby providing for a relatively low level of damping of axial motion of the plunger element relative the syringe. Still further preferably, upon rearward axial displacement of the plunger element, air contained within the syringe is configured to be released via the at least one slot.

Preferably, the forward sealing element is displaceable axially along the narrowed cylindrical axial portion. Alternatively, the forward sealing element is an annular element, being fixedly attached to the plunger element and radially extends outwardly with respect to the circumference of the plunger element. Further alternatively, the forward sealing element is a rubber-edged blade set, being fixedly attached to the plunger element and radially extends outwardly with respect to the circumference of the plunger element. Still further alternatively, the plunger element includes a plunger body and a separate forward dampening portion, configured for mounting of the forward sealing element thereon, and wherein the forward sealing element is radially extends outwardly with respect to the circumference of the separate forward dampening portion.

In accordance with an embodiment of the present invention, an automatic injection device including: a generally cylindrical syringe body having an opening, an outlet and an inner cylindrical surface adapted to contain an injectable liquid to be injected at an injection site via the outlet; a piston disposed in the cylindrical syringe body; a driving assembly, including a housing defining an axial travel path having an inner wall surface, an elongate axial plunger element extending along a longitudinal axis and having a rearward end arranged for axial travel along the axial travel path and defining at least one rearward sealing element seat and an at least partial rearward sealing element mounted onto the elongate plunger element at the at least one rearward sealing element seat for creating an at least temporary slidable seal between the elongate plunger element and the inner wall surface, the rearward sealing element seat having a rearward sealing element support which is generally perpendicular to the longitudinal axis and a forward sealing element support, facing the rearward sealing element support but being angled with respect thereto and with respect to the longitudinal axis, thereby allowing the rearward sealing element to be axially tilted from an orientation perpendicular to the longitudinal axis upon rearward axial displacement of the plunger element causing at least partial disengagement of the rearward sealing element from the inner wall surface of the axial travel path.

Preferably, the elongate axial plunger element having a forward end adapted to be axially inserted into the generally cylindrical syringe body and an at least partial forward sealing element mounted onto the elongate axial plunger element adjacent the forward end for creating an at least temporary slidable seal between the elongate plunger element and the inner cylindrical surface. Further preferably, axial insertion of the elongate axial plunger element and the forward sealing element into the generally cylindrical syringe body creates friction between the forward sealing element and the inner cylindrical surface and also creates an at least temporary air spring between the forward sealing element and the piston, wherein the friction and the air spring dampen motion of the elongate axial plunger element. Still further preferably, the forward sealing element support has at least one slot formed therein.

In accordance with an embodiment of the present invention, the at least one rearward sealing element seat includes a cylindrical axial portion extending from the rearward sealing element support to the forward sealing element support and a tapered axial portion formed adjacent the rearward sealing element support. Preferably, engagement of the rearward sealing element with the forward sealing element support provides for a relatively low level of damping of axial motion of the plunger element relative the housing. Further preferably, upon forward axial displacement of the plunger element, the rearward sealing element is displaced to an orientation perpendicular to the longitudinal axis causing engagement of the rearward sealing element with the inner wall surface of the axial travel path and thus a relatively high level of damping of axial motion of the plunger element relative the housing. Still further preferably, upon forward axial displacement of the plunger element, the rearward sealing element engages the tapered axial portion. Yet further preferably, upon rearward axial displacement of the plunger element, air contained within the housing is configured to be released via the at least one slot.

In accordance with an embodiment of the present invention, upon forward axial displacement of the plunger element, a partial vacuum is created between the housing and the rearward sealing element, thus enhancing damping of forward axial motion of the plunger element relative the housing. Preferably, the rearward sealing element is displaceable axially along the cylindrical axial portion. Further preferably, the rearward sealing element is an O-ring.

In accordance with another embodiment of the present invention, a medicament module, including: a module housing at least partially surrounding a needle shield and arranged along a mutual longitudinal axis therewith; an RNS remover assembly, attached to the needle shield and configured to be detachable from the needle shield but not to be subsequently re-attachable thereto.

Preferably, the module housing has a forward end and a rearward end and at least one finger disposed between the forward end and the rearward end and wherein the finger has at least one side protrusion. Further preferably, the needle shield has at least one mounting arm formed with a recess, the needle shield has a forward circumferential rim. Still further preferably, the at least one mounting arm is also formed with at least one slot, arranged rearwardly of the recess. Yet further preferably, the recess is disposed at a forward end of the mounting arm, the recess has a forward tapered surface.

In accordance with an embodiment of the present invention, the RNS remover assembly has an outer portion and an inner portion, the inner portion is slidable relative the outer portion along the longitudinal axis. Preferably, the outer portion has at least one longitudinally extending arm, which extends to an edge surface, and wherein the at least one longitudinally extending arm is formed with a protrusion. Further preferably, the outer portion has at least one rearwardly extending arm, which extends to a rearwardmost edge surface, and wherein the at least one rearwardly extending arm is formed with an inwardly extending protrusion, having a rearwardly-facing angled edge and a forwardly-facing angled edge, both being angled with respect to the longitudinal axis.

Preferably, the needle shield has at least one mounting arm formed with a recess and at least one slot, arranged rearwardly of the recess, the needle shield also has a forward circumferential rim. Further preferably, the module housing has a forward end and a rearward end and at least one finger disposed between the forward end and the rearward end and wherein the finger has at least one side protrusion.

In accordance with an embodiment of the present invention, in a storage operative orientation, when the RNS remover assembly is attached to the needle shield, the forward end of the module housing abuts the rearwardmost edge surface of the outer portion of the RNS remover assembly.

Preferably, in the storage operative orientation, relative displacement between the module housing and the needle shield is not permitted due to engagement of the at least one side protrusion of the module housing with the at least one slot of the needle shield. Further preferably, the protrusion of the outer portion is inserted into the recess of the needle shield in the storage operative orientation. Still further preferably, the RNS remover assembly is configured to be detached from the needle shield when the RNS remover assembly being pulled forwardly relative to the needle shield. Yet further preferably, the protrusion of the outer portion is disengaged from the recess of the needle shield when the RNS remover assembly is being detached from the needle shield. Still further preferably, the RNS remover assembly is being detached from the needle shield due to slidable displacement of the rearwardly-facing angled edge of the protrusion of the outer portion relative to the tapered surface of the recess of the needle shield.

In accordance with an embodiment of the present invention, when the RNS remover assembly is being pushed forwardly with respect to the needle shield, re-attachment of the RNS remover assembly to the needle shield is prevented by engagement of the protrusion of the outer portion with the circumferential rim of the needle shield. Preferably, during re-attachment of the RNS remover assembly to the needle shield, the forward end of the module housing is spaced from the rearwardmost edge surface of the outer portion of the RNS remover assembly, thus allowing relative displacement between the needle shield and the module housing. Further preferably, during re-attachment of the RNS remover assembly to the needle shield, relative displacement between the module housing and the needle shield is allowed due to disengagement of the at least one side protrusion of the module housing from the at least one slot of the needle shield.

BRIEF DESCRIPTION OF DRAWINGS

Some embodiments of the invention are described herein with reference to the accompanying drawings. The description, together with the drawings, makes apparent to a person having ordinary skill in the art how some embodiments of the invention may be practiced. The drawings are for the purpose of illustrative discussion and no attempt is made to show structural details of an embodiment in more detail than is necessary for a fundamental understanding of the invention. For the sake of clarity, some objects depicted in the drawings are not to scale.

FIGS. 4A-4E are respectively a simplified pictorial, two simplified different side views and two orthogonal sectional illustrations of the plunger and damper body, forming part of the improved plunger and damper assembly of FIG. 2, sections being taken along lines D-D in FIG. 4C and lines E-E in FIG. 4B;

FIGS. 6A and 6B are respectively a simplified plan view illustration and a simplified sectional illustration taken along lines B-B in FIG. 6A of a transition between respective relatively weak and relatively strong damping operative orientations of another portion of the improved plunger and damper assembly of FIG. 2;

FIGS. 7A-7C are respectively a simplified pictorial view and two orthogonal sectional illustrations of the automatic injection device with the medicament module of FIGS. 1A & 1B, where the improved plunger and damper assembly of FIG. 2 is forming part of the automatic injection device, sections being taken along perpendicular lines B-B and C-C in FIG. 7A, the automatic injection device is shown in a charging operative orientation;

FIGS. 10A-10C are respectively a simplified pictorial view and two orthogonal sectional illustrations of the automatic injection device with the medicament module of FIGS. 1A & 1B, where the improved plunger and damper assembly of FIG. 2 is forming part of the automatic injection device, sections being taken along lines B-B and C-C in FIG. 10A, the automatic injection device is shown in a removal from injection site operative orientation;

FIGS. 11A-11C are respectively a simplified pictorial illustration, a side view and a sectional illustration of an improved plunger and damper assembly useful in various automatic injection devices, such as shown in FIGS. 1A & B and constructed and operative in accordance with another embodiment of the present invention, section being taken along lines C-C in FIG. 11B;

FIGS. 12A-12C are respectively a simplified pictorial illustration, a side view and a sectional illustration of an improved plunger and damper assembly useful in various automatic injection devices, such as shown in FIGS. 1A & B and constructed and operative in accordance with still another embodiment of the present invention, section being taken along lines C-C in FIG. 12B;

FIGS. 13A-13C are respectively a simplified pictorial illustration, a side view and a sectional illustration of an improved plunger and damper assembly useful in various automatic injection devices, such as shown in FIGS. 1A & B and constructed and operative in accordance with yet another embodiment of the present invention, section being taken along lines C-C in FIG. 13B;

FIGS. 16A, 16B, 16C, 16D, 16E, 16F, 16G and 16H are simplified respective perspective, top and bottom view, side view, first and second end view and three sectional illustrations taken along lines F-F in FIG. 16B, lines G-G in FIG. 16C and H-H in FIG. 16B of a module housing, forming part of the improved medicament module of FIGS. 15A & 15B;

FIGS. 17A, 17B, 17C, 17D, 17E, 17F, 17G and 17H are simplified respective perspective, top and bottom view, side view, first and second end view and three sectional illustrations taken along lines F-F in FIG. 17B, lines G-G in FIG. 17C and lines H-H in FIG. 17B of a needle shield, forming part of the improved medicament module of FIGS. 15A & 15B;

FIGS. 18A and 18B are respectively simplified assembled view and exploded view pictorial illustrations of an RNS remover assembly, forming part of the improved medicament module of FIGS. 15A & 15B;

FIGS. 19A and 19B are simplified respective pictorial and sectional illustrations of an outer portion of the RNS remover assembly of FIGS. 18A & 18B, section being taken along lines B-B in FIG. 19A;

FIGS. 20A and 20B are simplified respective pictorial and sectional illustrations of an inner portion of the RNS remover assembly of FIGS. 18A & 18B, section being taken along lines B-B in FIG. 20A;

FIGS. 21A, 21B, 21C and 21D are simplified respective first and second perspective views, end view and a sectional view taken along lines D-D in FIG. 21C of an assembled RNS remover assembly, forming part of the improved medicament module of FIGS. 15A & 15B;

FIGS. 22A and 22B are two different simplified plan views of the assembled improved medicament module of FIGS. 15A & 15B in a storage operative orientation, showing the RNS remover assembly of FIGS. 18A & 18B attached to the needle shield of FIGS. 17A-17H;

FIGS. 23A and 23B are respectively simplified pictorial and section view illustrations of the improved medicament module of FIGS. 15A & 15B, showing the RNS remover assembly of FIGS. 18A & 18B detached from the needle shield of FIGS. 17A-17H, section being taken along lines B-B in FIG. 23A;

FIGS. 24A and 24B are respectively simplified pictorial and section view illustrations of the improved medicament module of FIGS. 15A & 15B, shown in a mis-use orientation of the improved medicament module associated with the automatic injection device of FIGS. 1A & 1B, when the user attempts to re-attach the RNS remover assembly back onto the needle shield of FIGS. 17A-17H of the improved medicament module, section being taken along lines B-B in FIG. 24A.

DESCRIPTION OF EMBODIMENTS OF THE INVENTION

Figure 1A:
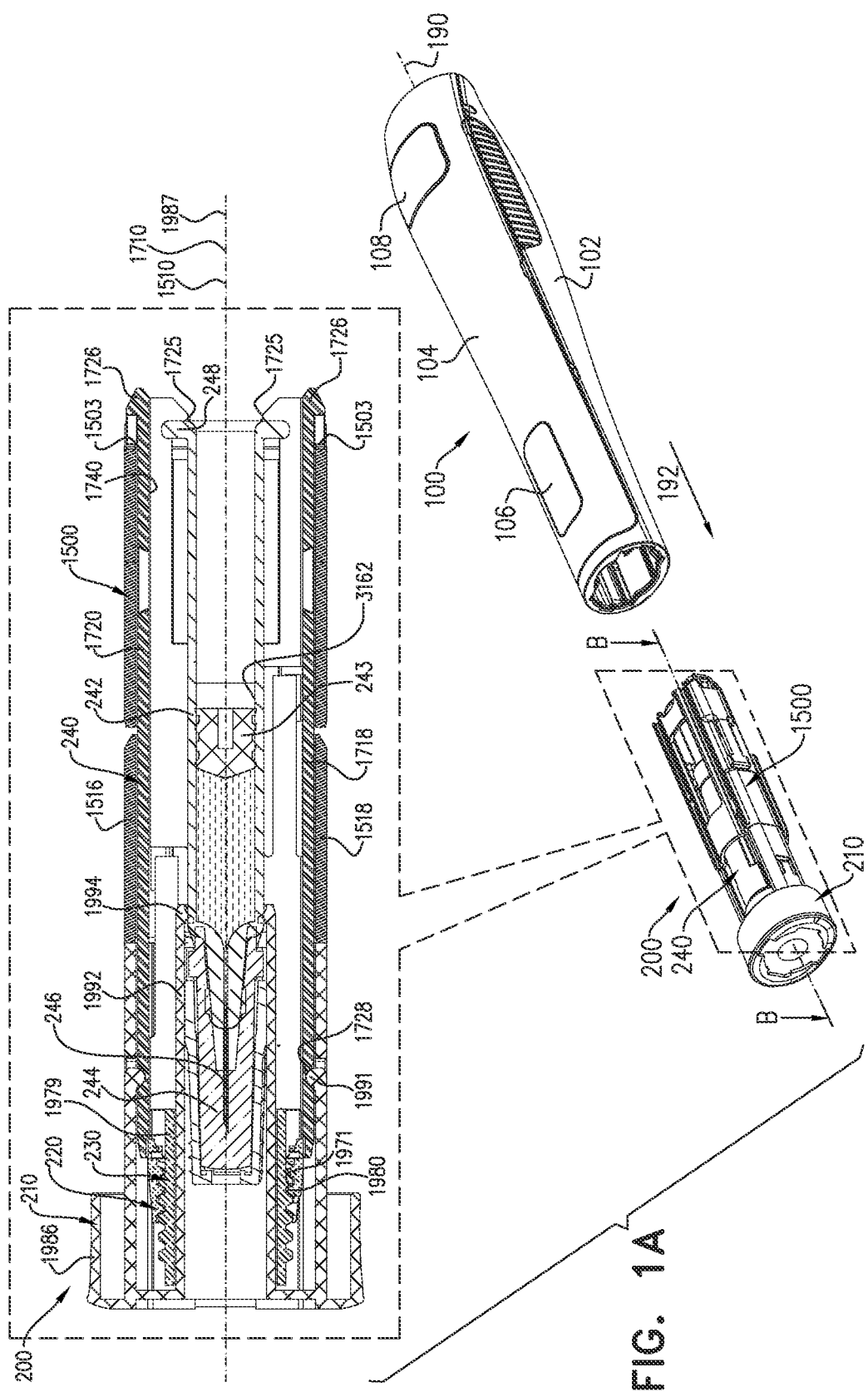
FIG. 1A is a simplified pictorial illustration of an automatic injection device with a medicament module adapted to be inserted thereinto, along with a sectional view of the medicament module as taken along lines B-B, the automatic injection device and the medicament module being constructive and operative in accordance with an embodiment of the present invention.
Figure 1B:
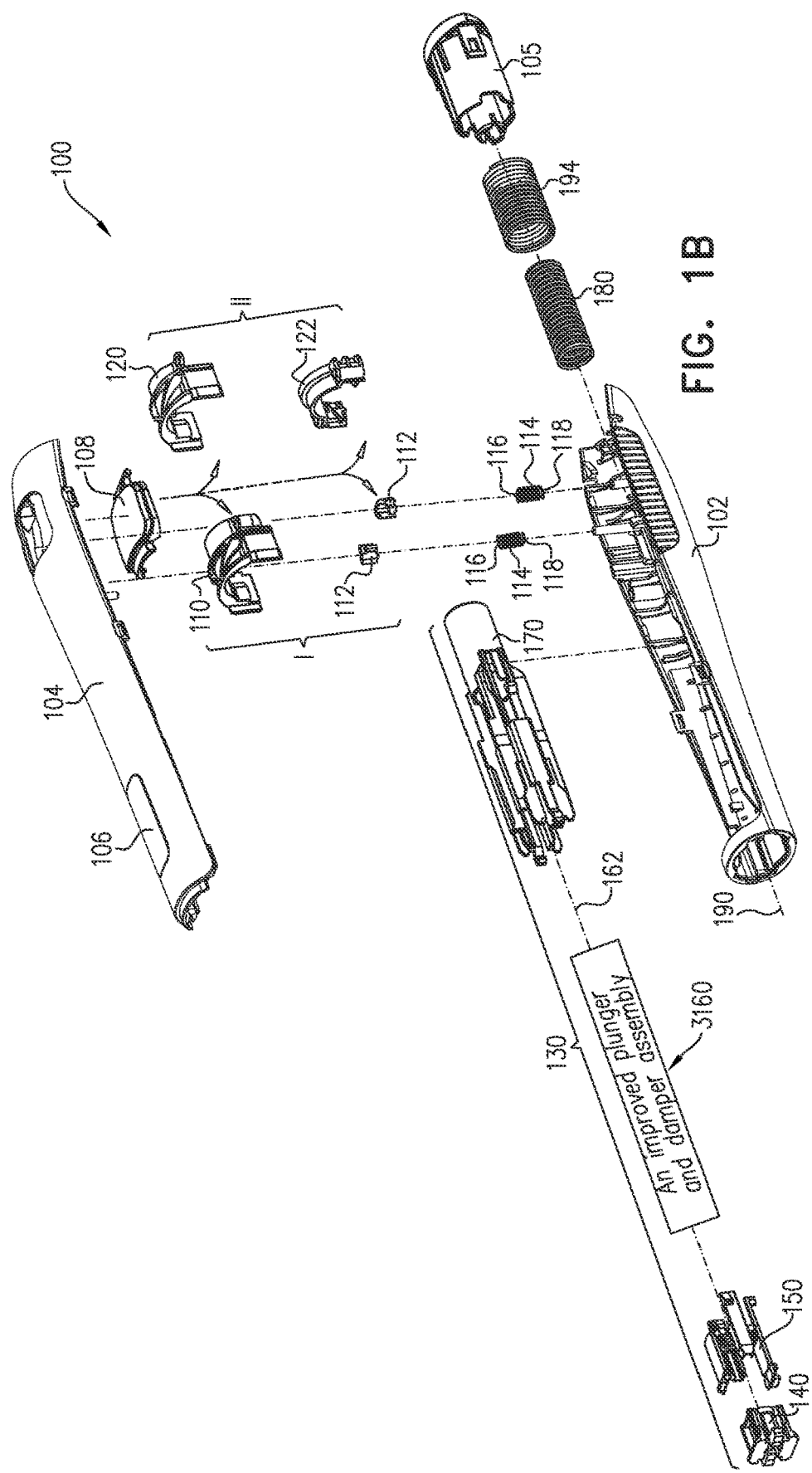
FIG. 1B is a simplified exploded illustration of the automatic injection device of FIG. 1A.

Reference is now made to FIG. 1A, which is a simplified pictorial illustration of an automatic injection device with a medicament module adapted to be inserted thereinto, along with a sectional view of the medicament module as taken along lines B-B in FIG. 1A, the automatic injection device and the medicament module being constructive and operative in accordance with an embodiment of the present invention. Reference is additionally made to FIG. 1B, which is a simplified exploded illustration of the automatic injection device of FIG. 1A.

As seen in FIGS. 1A and 1B, an automatic injection device 100 comprises a main housing portion 102, a cover portion 104 and an end portion 105, both of which are preferably in fixed snap fit engagement with main housing portion 102.

Cover portion 104 is preferably formed with a transparent window portion 106, which is preferably in fixed snap fit engagement with cover portion 104 and with a user-engageable actuation button 108 which is pivotably mounted at one side thereof onto cover portion 104.

Disposed within main housing portion 102 there is provided a driving assembly 130, which includes a control element 140, which operatively engages a multifunctional retaining element 150, which, in turn operatively engages an improved plunger and damper assembly 3160, which is described in detail hereinbelow.

A multifunctional engagement element 170 operatively engages the improved plunger and damper assembly 3160 and multifunctional retaining element 150 and is operatively engaged by either latches 112 or unitary latch element 122.

A first compression spring 180 operatively engages multifunctional retaining element 150 and improved plunger and damper assembly 3160 for driving them forwardly along a longitudinal axis 190 in a direction indicated by an arrow 192. A second compression spring 194 is arranged in coaxial relationship with first compression spring 180 and operatively engages multifunctional engagement element 170 for driving it forwardly along longitudinal axis 190 in a direction indicated by arrow 192.

All components of the automatic injection device 100 are preferably identical to that shown in FIGS. 1A & 1B of PCT Patent application PCT/IL2016/050929 and described therein, other than the improved plunger and damper assembly 3160, which is different from the elongate damping driver element 160 described in the PCT/IL2016/050929. The disclosure of PCT Patent application PCT/IL2016/050929 is hereby incorporated by reference.

It is particularly seen in FIG. 1A that the automatic injection device 100 is adapted to receive a medicament module 200 thereinto. All components of the medicament module 200 are identical to that shown in FIGS. 35A-35D of PCT Patent application PCT/IL2016/050929 and described therein. In an alternative embodiment of the present invention, an improved medicament module is utilized in conjunction with the automatic injection device 100, such as described in detail hereinbelow with reference to FIGS. 14A-24B.

Preferably, the automatic injection device 100 is reusable and the medicament module 200 is disposable. Alternatively, both the automatic injection device 100 and the medicament module 200 are disposable. Further alternatively, both the automatic injection device 100 and the medicament module 200 are reusable.

It is seen in FIG. 1A, particularly in the sectional view of the medicament module 200 that needle shield 240 is located generally inside and coaxial with module housing 1500, such that respective axes 1510 and 1710 are coaxial. It is also seen that in a "storage" operative orientation of the medicament module 200, the needle shield 240, is fixedly retained in the module housing 1500 against axial relative movement therebetween.

It is additionally seen that syringe 242 is fixedly retained against rearward axial motion along axis 1710 relative to needle shield 240 and module housing 1500 by engagement of protrusion 1725 of needle shield 240 with flange 248 of syringe 242.

It is further seen that syringe 242 is fixedly retained against forward axial motion along axis 1710 relative to needle shield 240 and module housing 1500 by engagement of flange 248 of syringe 242 with a portion of the module housing 1500.

It is also described in FIGS. 35A-35D of PCT Patent application PCT/IL2016/050929 that needle shield 240 is retained against forward or rearward axial displacement relative to module housing 1500 along coaxial axes 1510 and 1710.

It is also seen in FIG. 1A that RNS remover 210 is located generally forwardly of the module housing 1500 and both inside and outside of needle shield 240 and coaxially therewith such that, respective axes 1987, 1510 and 1710 are coaxial. It is further seen that protrusions 1991 of RNS remover 210 are seated in corresponding recesses 1728 of the needle shield 240.

It is particularly noted that the syringe 242 defines an inner surface 3162.

Figure 2:
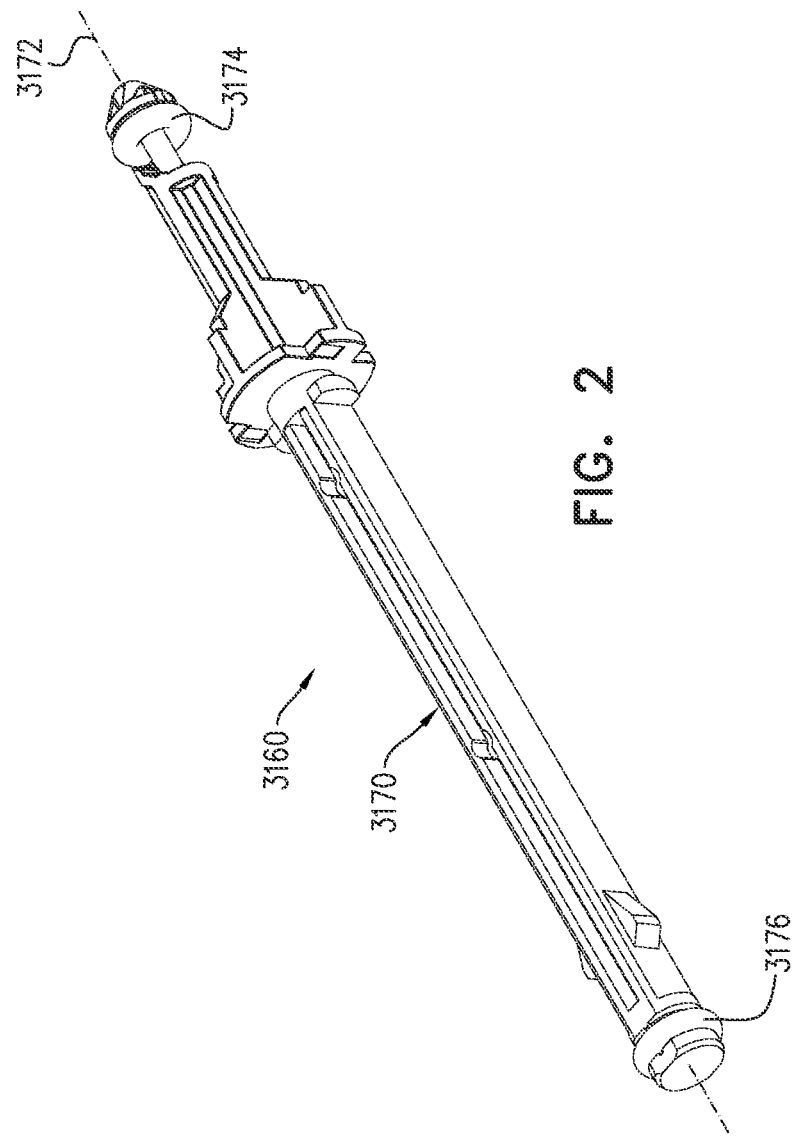
FIG. 2 is a simplified pictorial illustration of an improved plunger and damper assembly useful in various automatic injection devices, such as shown in FIGS. 1A & B.
Figure 3:
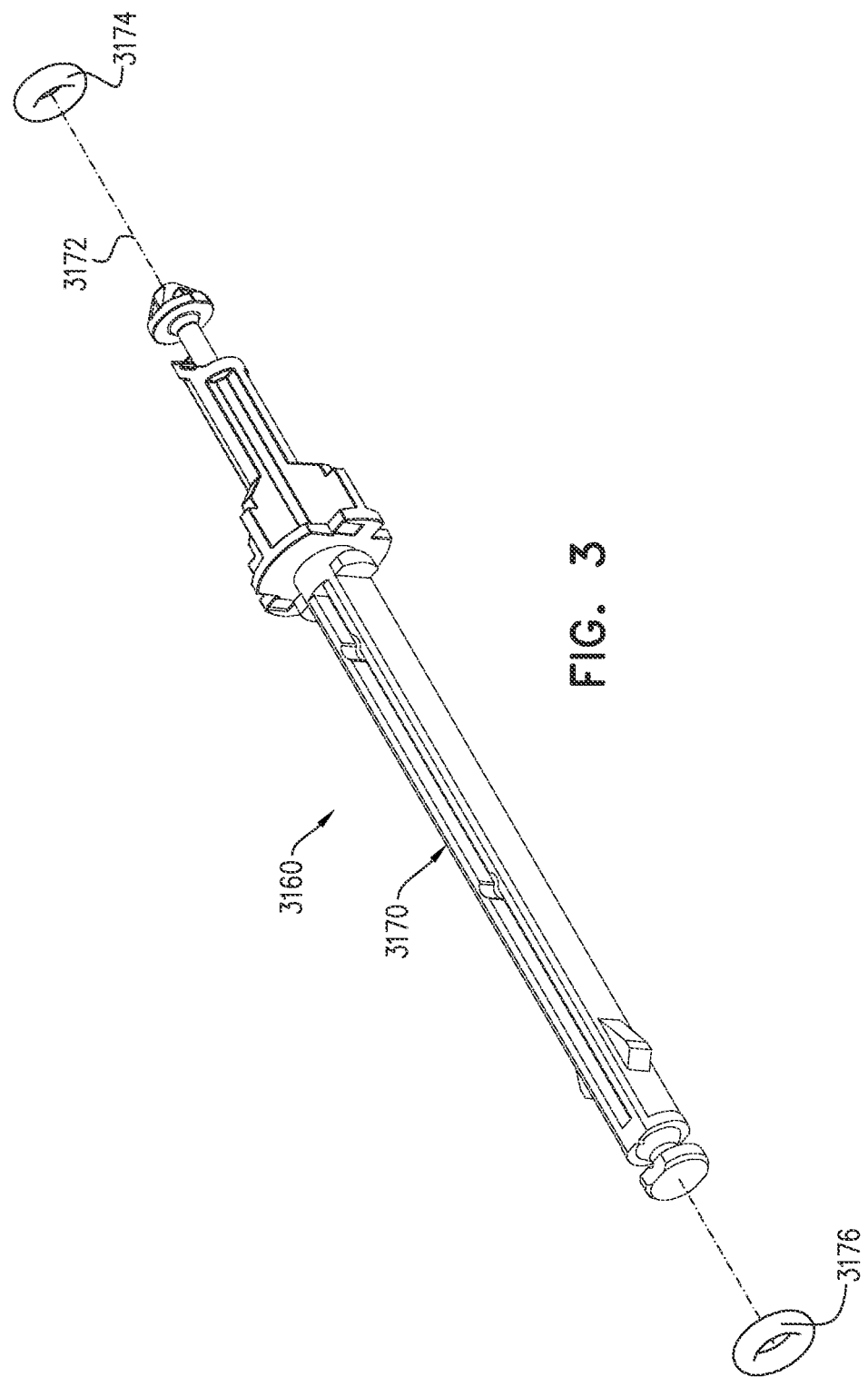
FIG. 3 is a simplified exploded view illustration of the improved plunger and damper assembly of FIG. 2.

Reference is now made to FIG. 2, which is a simplified pictorial illustration of the improved plunger and damper assembly 3160 useful in various automatic injection devices, such as shown in FIGS. 1A & B. Reference is additionally made to FIG. 3, which is a simplified exploded view illustration of the improved plunger and damper assembly 3160 of FIG. 2.

It is noted that the improved plunger and damper assembly 3160 is useful in various automatic injection devices, such as described in the following Published PCT Patent Applications, for example: WO2008/047372; WO2017/033193; WO2015/118550 or WO2014/174519.

As seen in FIGS. 2 & 3, the improved plunger and damper assembly 3160 includes a plunger and damper body 3170, which is generally arranged along a longitudinal axis 3172. The plunger and damper body 3170 is configured for receiving a rearward dampening element 3174, such as an O-ring, for example and a forward dampening element 3176, such as an O-ring for example.

Figure 4B:
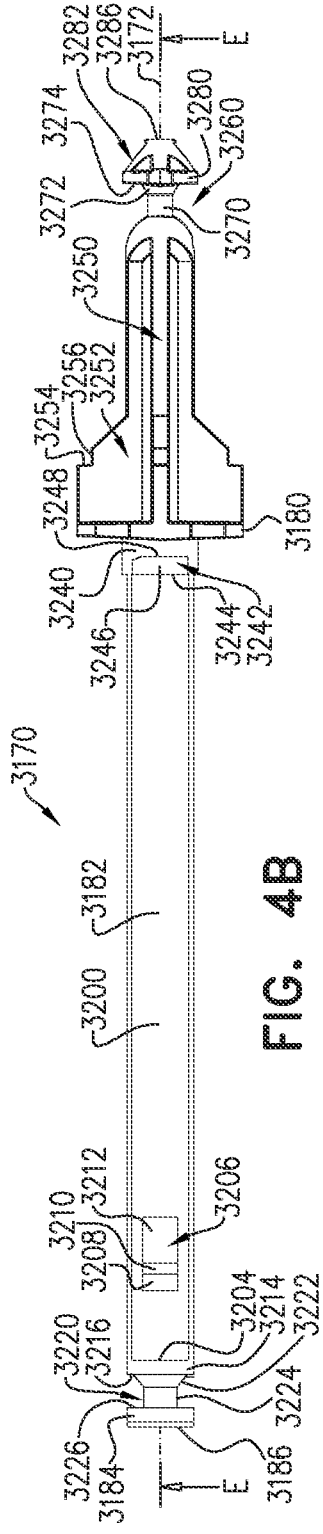
Figure 4C:
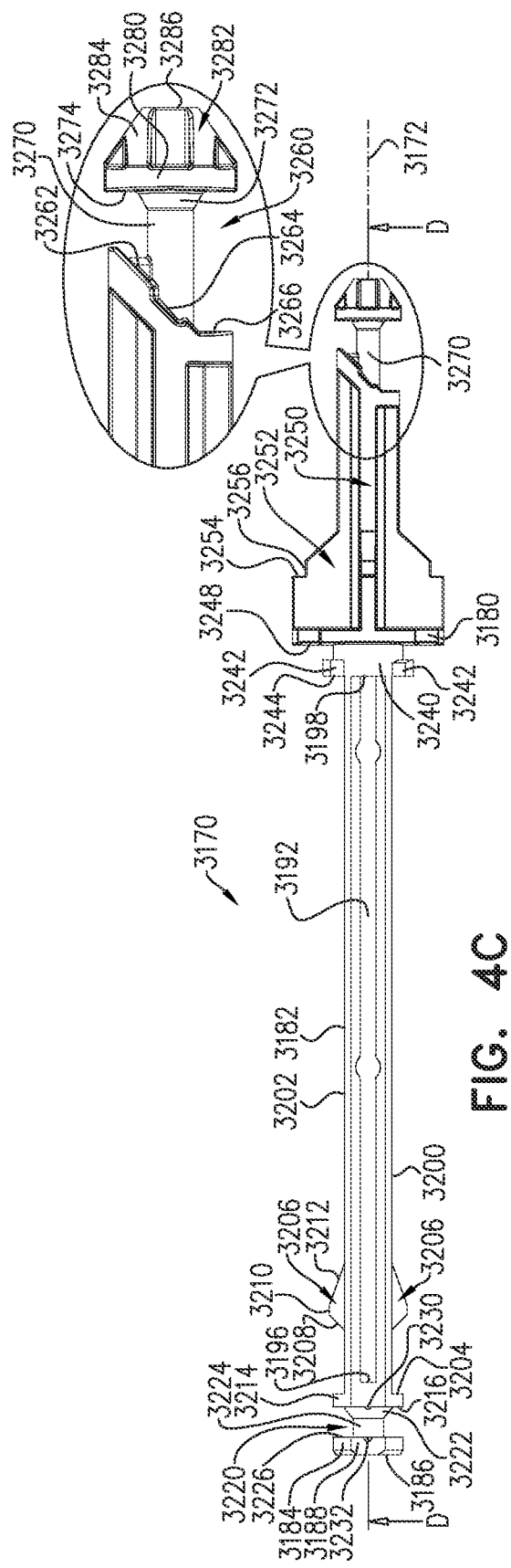

Reference is now made to FIGS. 4A-4E, which are respectively a simplified pictorial, two simplified different side views and two orthogonal sectional illustrations of the plunger and damper body 3170, forming part of the improved plunger and damper assembly 3160 of FIG. 2, sections being taken along lines D-D in FIG. 4C and lines E-E in FIG. 4B.

The plunger and damper body 3170 preferably has top to bottom and side to side general axial symmetry, and includes a generally planar base 3180 from which extends forwardly along axis 3172 a longitudinal rod 3182 having a generally rectangular cross section. The longitudinal rod 3182 terminates at a generally circular cylindrical portion 3184 having a forwardly facing contact surface 3186, which lies in a plane perpendicular to axis 3172.

Generally circular cylindrical portion 3184 is formed with respective top and bottom facing flat wall surfaces 3188 and 3190.

Longitudinal rod 3182 is formed with respective top and bottom facing channels 3192 and 3194, each having respective forward and rearward bulkhead surface 3196 and 3198.

Longitudinal rod 3182 is formed with generally planar side-facing surfaces 3200 and 3202, each terminating at a rearwardly-facing shoulder surface 3204 and each having a forward side protrusion 3206. Each side protrusion 3206 preferably includes a tapered planar forward-facing surface 3208, an apex 3210 and a tapered planar rearward-facing tapered surface 3212 extending from the apex 3210. A generally half-circular section 3214 is formed on each of the planar side-facing surfaces 3200 and 3202, adjacent the rearwardly facing shoulders 3204. The half-circular sections 3214 define a forwardly-facing surface 3216.

It is a particular feature of an embodiment of the present invention that an axial movement direction dependent forward damping control friction element seat 3220 is formed typically between cylindrical portion 3184 and the half circular sections 3214 and is configured for receiving the forward dampening element 3176.

It is seen in FIGS. 4A-4E that axial movement direction dependent forward damping control friction element seat 3220 preferably includes a forwardly tapered section 3222 extending forwardly from the forwardly-facing surface 3216, a narrowed cylindrical portion 3224 extending forwardly from the forwardly tapered section 3222, terminating at a generally planar rearwardly facing surface 3226, formed by the circular cylindrical portion 3184.

Typically, at least one protrusion 3230 is formed on the forwardly-facing surface 3216. Protrusion 3230 generally extends slightly towards forwardly tapered section 3222.

Further, typically, at least one recess 3232 is formed on rearwardly facing surface 3226. Recess 3232 generally extends slightly to the outer surface of circular cylindrical portion 3184.

It is noted that, alternatively, series of axial movement direction dependent forward damping control friction element seats 3220 can be formed at the forward end of longitudinal rod 3182.

It is further noted that, alternatively, the axial movement direction dependent forward damping control friction element seat 3220 can be formed without at least one of protrusion 3230 and recess 3232.

Adjacent planar base 3180, longitudinal rod 3182 includes a generally circular cylindrical portion 3240 from which extend a pair of rearward side protrusions 3242. Each side protrusion 3242 preferably includes a planar forward-facing surface 3244, a convex, radially outwardly facing surface 3246 and a planar rearward-facing surface 3248.

Rearward of base 3180 there is formed an intermediate elongate portion 3250, preferably having four radially extending stepped ribs 3252, each separate by 90 degrees from its neighbors. Each of stepped ribs 3252 preferably includes a shoulder 3254 which defines a spring seat for a forward-facing end of spring 180 (FIG. 1B) and an elongate edge surface 3256. Edge surfaces 3256 together serve to position spring 180 radially with respect to axis 3172.

It is a particular feature of an embodiment of the present invention that rearwardly of intermediate elongate portion 3250 is a tilted axial movement direction dependent rearward damping control friction element seat 3260, configured for receiving the rearward dampening element 3174.

Rearward damping control friction element seat 3260 includes a rearwardly facing circumferential inclined surface 3262, which lines in a plane disposed at an angle with respect to longitudinal axis 3172, preferably having a pair of mutually oppositely radially outwardly directed slots 3264. The inclined surface 3262 is typically slightly truncated to form a relatively small planar rearwardly facing surface 3266 adjacent the inclined surface 3262.

Extending rearwardly from inclined surface 3262 is a generally circular cylindrical axial portion 3270. Extending rearwardly from generally circular cylindrical axial portion 3270 is a generally circularly symmetric forwardly and outwardly tapered axial portion 3272, which terminates at a forwardly facing planar annular surface 3274, which lies in a plane generally perpendicular to the longitudinal axis 3172. Planar annular surface 3274 faces the inclined surface 3262 and disposed at an angle with respect thereto.

It is appreciated that planar annular surface 3274 of the rearward damping control friction element seat 3260 and inclined surface 3262 of the rearward damping control friction element seat 3260 are defined on a single radially extending bulkhead, such as a bulkhead designated by reference numeral 3280.

Rearwardly of the rearward damping control friction element seat 3260 there is preferably defined a rearward end portion 3282 having a rearwardly and inwardly tapered circumferential surface 3284 and a generally planar rearward facing surface 3286.

Alternatively, there may be a series of rearward damping control friction element seat 3260 that are arranged axially one adjacent the other.

It is noted that in another embodiment of the present invention, the improved plunger and damper assembly 3160 can also include only one of either axial movement direction dependent forward damping control friction element seat 3220 adapted for mounting of forward dampening element 3176 thereon or axial movement direction dependent rearward damping control friction element seat 3260 adapted for mounting of rearward dampening element 3174 thereon.

Figure 5A:
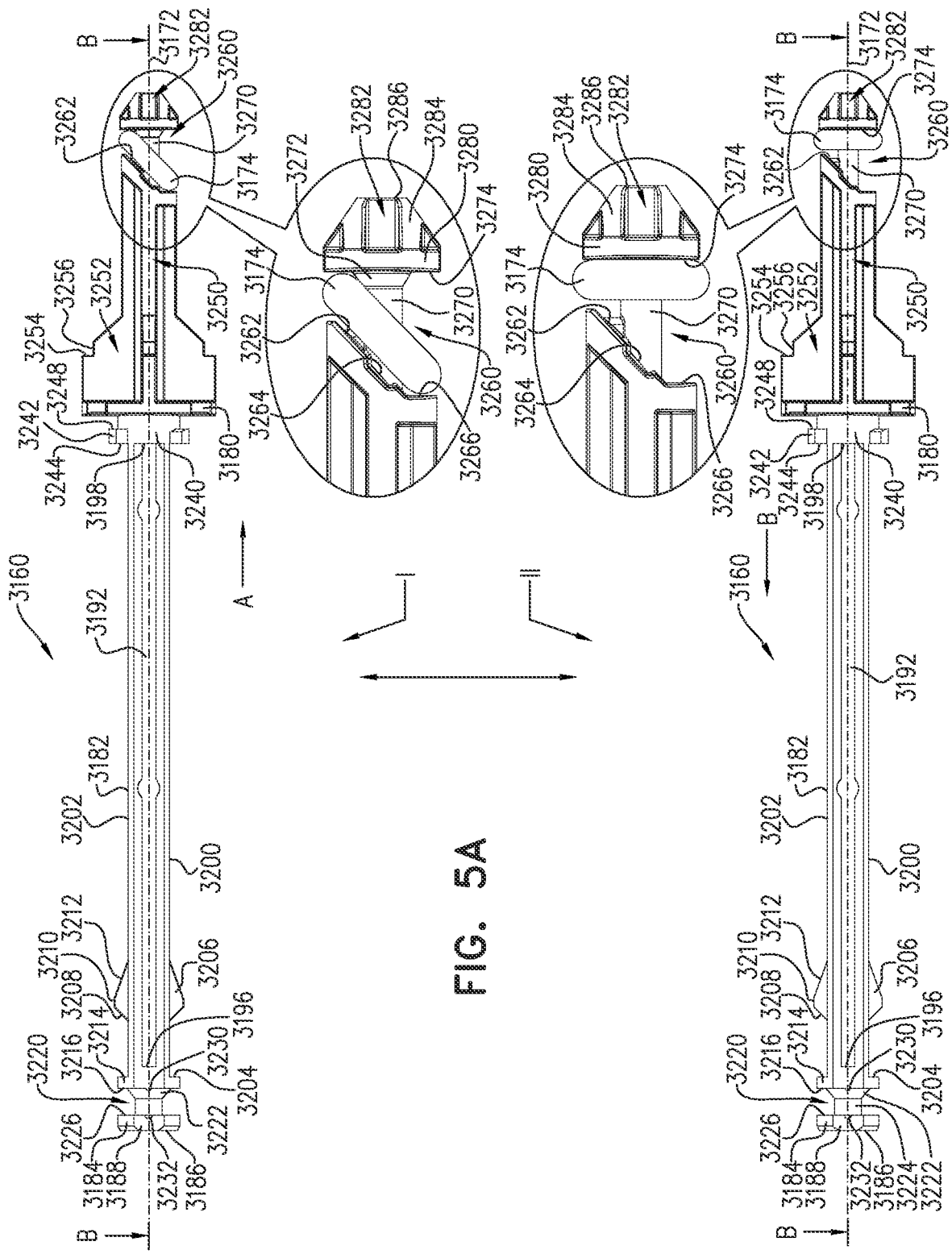
FIGS. 5A and 5B are respectively a simplified plan view illustration and a simplified sectional illustration taken along lines B-B in FIG. 5A of a transition between respective relatively weak and relatively strong damping operative orientations of a portion of the improved plunger and damper assembly of FIG. 2.
Figure 5B:
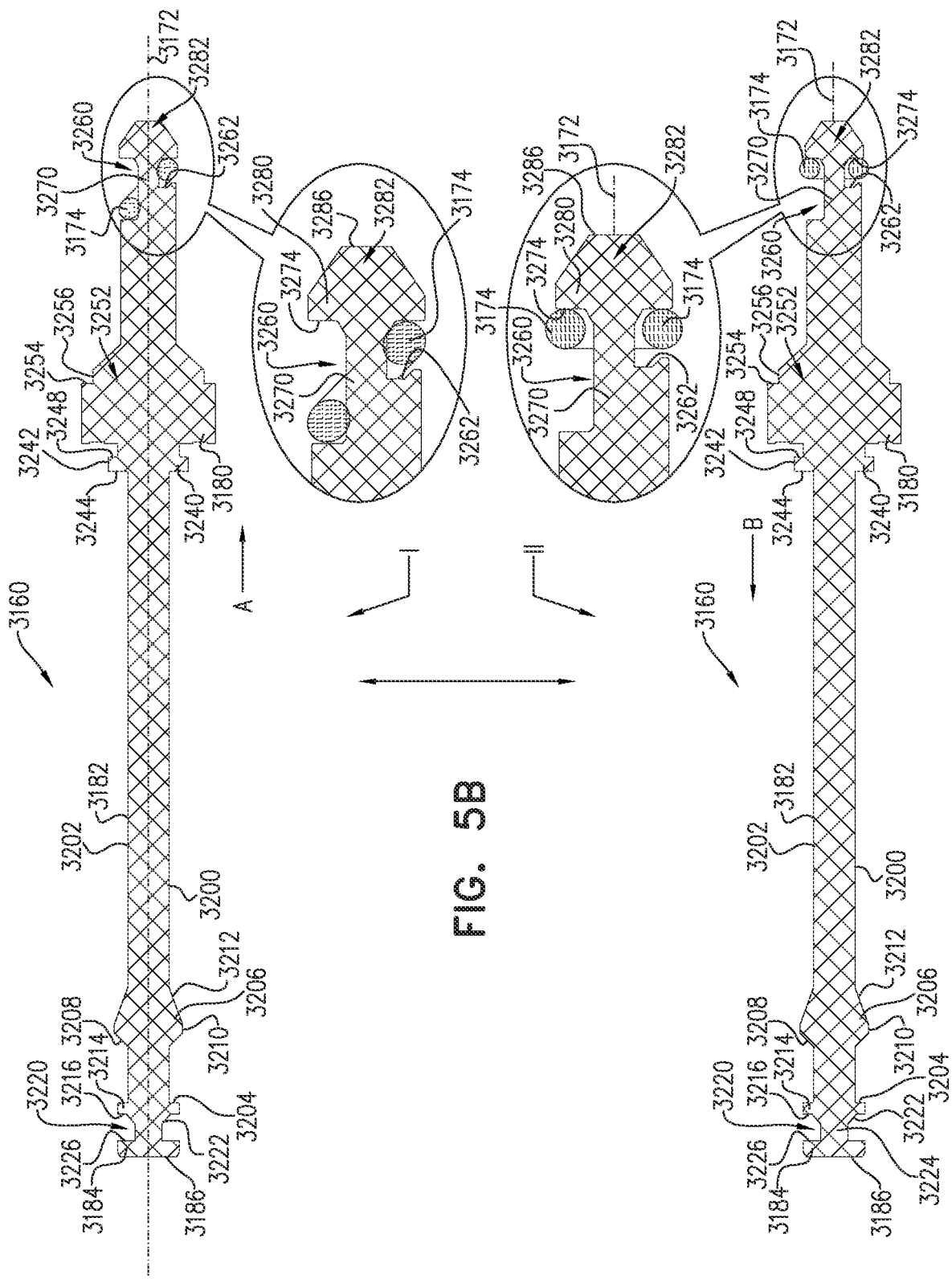

Reference is now made to FIGS. 5A and 5B, which are respectively a simplified plan view illustration and a simplified sectional illustration taken along lines B-B in FIG. 5A of a transition between respective relatively weak and relatively strong damping operative orientations of a portion of the improved plunger and damper assembly 3160 of FIG. 2.

It is noted that in FIGS. 5A & 5B only the rearward dampening element 3174 is shown mounted onto axial movement direction dependent rearward damping control friction element seat 3260 of the improved plunger and damper assembly 3160 and the transition thereof is explained in detail hereinbelow.

As seen in FIGS. 5A and 5B, it is a particular feature of an embodiment of the present invention that when the improved plunger and damper assembly 3160 is in rearward motion, relative to main housing portion 102 as indicated by an arrow A and shown as stage I, the rearward dampening element 3174 located in the rearward damping control friction element seat 3260 is forced forwardly by frictional engagement with end cover 105 (FIG. 1B) into engagement with inclined surface 3262 and surrounds generally circular cylindrical axial portion 3270 and is generally at rest, thus providing a relatively low level of damping of axial motion of the improved plunger and damper assembly 3160 in rearward motion.

When the improved plunger and damper assembly 3160 is in forward motion, relative to main housing portion 102 as indicated by an arrow B and shown as stage II, rearward dampening element 3174 located in the rearward damping control friction element seat 3260 is forced rearwardly by frictional engagement with end cover 105 (FIG. 1B) into engagement with forwardly facing planar annular surface 3274 and surrounds tapered axial portion 3272. Engagement of rearward dampening element 3174 with tapered axial portion 3272 forces rearward dampening element 3174 radially outwardly and thus increases its frictional engagement with end cover 105, thus providing a relatively high level of damping of axial motion of the improved plunger and damper assembly 3160 in forward motion.

It is a particular feature of an embodiment of the present invention that the rearward dampening element 3174 is mounted onto the rearward damping control friction element seat 3260 of the plunger and damper body 3170 for creating an at least temporary slidable seal between the plunger and damper body 3170 and the inner facing surface 931 of the cylindrical portion 906. The rearward damping control friction element seat 3260 has the forwardly facing planar annular surface 3274 which serves as a rearward sealing element support which is generally perpendicular to the longitudinal axis 3172 and the inclined surface 3262, which serves as a forward sealing element support, facing the rearward sealing element but being angled with respect thereto and with respect to the longitudinal axis 3172. Displacement of the rearward dampening element 3174 from its rearward operative orientation engaging the planar annular surface 3274 into its forward operative orientation engaging the inclined surface 3262, allows the rearward dampening element 3174 to be axially tilted from an orientation perpendicular to the longitudinal axis 3172 upon rearward axial displacement of the plunger and damper body 3170. The rearward dampening element 3174 in its forward operative orientation causing at least partial disengagement thereof from the inner facing surface 931 of cylindrical portion 906.

It is an additional particular feature of an embodiment of the present invention that under rearward motion of the improved plunger and damper assembly 3160, air which would otherwise be trapped between the rearward dampening element 3174 and the end cover 105 is released via slots 3264. Were this air not to be released during rearward displacement of the improved plunger and damper assembly 3160, it would resist required rearward motion of the improved plunger and damper assembly 3160.

It is a further particular feature of an embodiment of the present invention that under forward motion of the improved plunger and damper assembly 3160, a partial vacuum is created between the rearward dampening element 3174 and the end cover 105 due to sealing engagement between the rearward dampening element 3174 and the inner-facing surface 931 of the cylindrical portion 906, which enhances damping of forward axial motion of the improved plunger and damper assembly 3160 relative to the main housing portion 102.

Reference is now made to FIGS. 6A and 6B, which are respectively a simplified plan view illustration and a simplified sectional illustration taken along lines B-B in FIG. 6A of a transition between respective relatively weak and relatively strong damping operative orientations of another portion of the improved plunger and damper assembly of FIG. 2.

It is noted that in FIGS. 6A & 6B only the forward dampening element 3176 is shown mounted onto axial movement direction dependent forward damping control friction element seat 3220 of the improved plunger and damper assembly 3160 and the transition thereof is explained in detail hereinbelow.

As seen in FIGS. 6A & 6B, it is a particular feature of an embodiment of the present invention that when the improved plunger and damper assembly 3160 is in forward motion, relative to syringe 242 (FIG. 1A) as indicated by an arrow C and shown as stage I, forward dampening element 3176 located in the forward damping control friction element seat 3220 is forced rearwardly by frictional engagement with the inner surface 3162 of the syringe 242 (FIG. 1A) into engagement with forwardly facing surface 3216 as well as with protrusion 3230 and surrounds tapered axial portion 3222. Engagement of forward dampening element 3176 with tapered axial portion 3222 forces forward dampening element 3176 radially outwardly and thus increases its frictional engagement with the inner surface 3162 of the syringe 242, thus providing a relatively high level of damping of axial motion of the improved plunger and damper assembly 3160 in forward motion.

It is an additional embodiment of the present invention that the forward dampening element 3176 further enables dampening the movement of the improved plunger and damper assembly 3160 before engagement between the improved plunger and damper assembly 3160 and the piston 243, thereby minimizing the risk of syringe breakage, even if the improved plunger and damper assembly 3160 has to travel a substantial distance up until engagement with the piston 243, such as in case of injecting a low volume dosage of medication, such as under 1.5 ml, for example.

Engagement of forward dampening element 3176 with tapered axial portion 3222 forces forward dampening element 3176 radially outwardly, thus partially seals the volume between forward dampening element 3176 and the piston 243, thereby causing pressure build-up therebetween and further enhances level of damping of axial motion of the improved plunger and damper assembly 3160 relative to syringe 242 in forward motion thereof.

It is noted that protrusion 3230 partially separates the forward dampening element 3176 from forwardly facing surface 3216 and thus provides for a small air passage, which in turn enables at least partial seal breakage between the forward dampening element 3176 and the piston 243 in order to allow air to escape in a rate which is slower than the rate of the pressure build-up. Allowing the air to escape enables engagement of the contact surface 3186 with piston 243 during forward displacement of the improved plunger and damper assembly 3160. The release of the air-pressure may occur prior to starting of the medicament injection, during the medicament injection, at the end of medicament injection, or even not released at all, depending on the size of protrusion 3230, or eliminating this protrusion at all.

It is further noted that in accordance with an alternative embodiment of the present invention, there is no such protrusion 3230 on the improved plunger and damper assembly 3160, thus air remains trapped between the forward dampening element 3176 and the piston 243, thus pressure continuously builds-up and forward displacement of the improved plunger and damper assembly 3160 urges forward displacement of the piston 243 through an air-spring formed therebetween, without any mechanical engagement between the contact surface 3186 and the piston 243.

When the improved plunger and damper assembly 3160 is in rearward motion, relative to the syringe 242 as indicated by an arrow D and shown as stage II, the forward dampening element 3176 located in the forward damping control friction element seat 3220 is forced forwardly by frictional engagement with the inner surface 3162 of the syringe 242 (FIG. 1A) into engagement with rearwardly facing surface 3226 and surrounds narrowed cylindrical portion 3224 and is generally at rest, thus providing a relatively low level of damping of axial motion of the improved plunger and damper assembly 3160 in rearward motion.

It is an additional particular feature of an embodiment of the present invention that under rearward motion of the improved plunger and damper assembly 3160, air which would otherwise be trapped between the forward dampening element 3176 and the inner volume of the syringe 242 is released via slots 3232. Were this air not to be released, it would resist required forward motion of the syringe 242 relative to the improved plunger and damper assembly 3160.

Figure 7A:
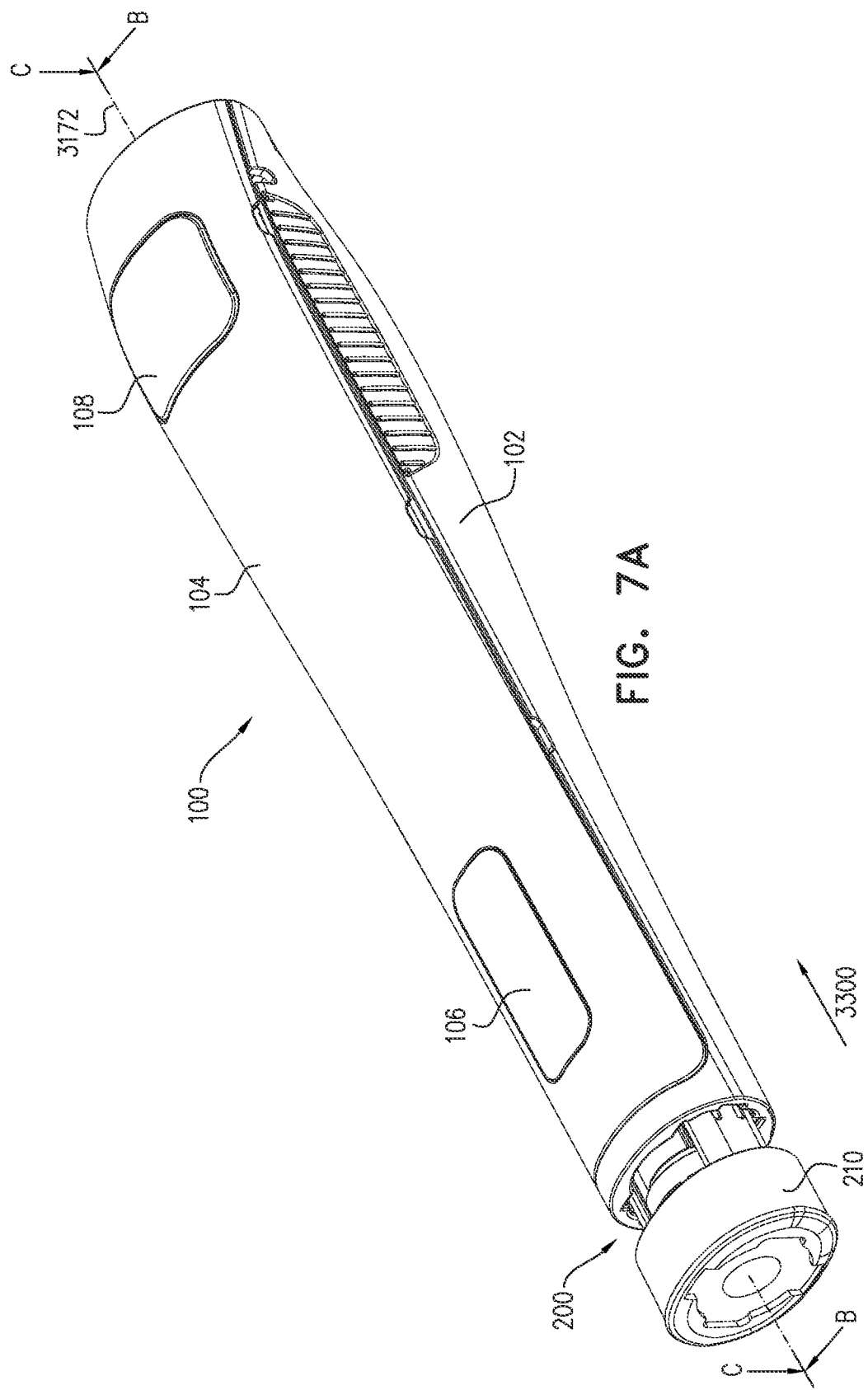

Reference is now made to FIGS. 7A-7C, which are respectively a simplified pictorial view and two orthogonal sectional illustrations of the automatic injection device 100 with the medicament module 200 of FIGS. 1A & 1B, where the improved plunger and damper assembly 3160 of FIG. 2 is forming part of the automatic injection device 100, sections being taken along perpendicular lines B-B and C-C in FIG. 7A, the automatic injection device 100 is shown in a charging operative orientation.

It is noted that all components of the automatic injection device 100 are preferably identical to that shown in PCT Patent application PCT/IL2016/050929 and described therein, other than the improved plunger and damper assembly 3160, which is different from the elongate damping driver element 160 described in the PCT/IL2016/050929. The disclosure of PCT Patent application PCT/IL2016/050929 is hereby incorporated by reference.

It is also noted that the improved plunger and damper assembly 3160 is useful in various automatic injection devices, such as described in the following Published PCT Patent Applications, for example: WO2008/047372; WO2017/033193; WO2015/118550 or WO2014/174519.

It is seen in FIGS. 7B & 7C that in this charging operative orientation an axial force is applied on the improved plunger and damper assembly 3160 in a direction indicated by an arrow 3300. The force is exerted on the improved plunger and damper assembly 3160 against the force of the first compression spring 180, such that the first compression spring 180 is partially compressed in this operative orientation due to the fact that the first compression spring is supported against shoulder 3254 of the improved plunger and damper assembly 3160.

As seen in enlargement A in FIG. 7C, a rearward portion of the improved plunger and damper assembly 3160 including a rearward portion of intermediate elongate portion 3250 and the rearward damping control friction element seat 3260, is partially inserted in inner cylindrical volume 930 of generally circular cylindrical portion 906 of end cover 105, such that rearward dampening element 3174 (FIG. 5A, stage I) is located adjacent the inclined surface 3262 of the improved plunger and damper assembly 3160 opposite bulkhead 3280, inwardly of inner-facing surface 931 of generally circular cylindrical portion 906 of end cover 105, thus exerting less frictional resistance to rearward displacement of the improved plunger and damper assembly 3160, as seen in stage I in FIGS. 5A & 5B.

It is noted that in this particular embodiment of the present invention, the rearward dampening element 3174 is an O-ring, however it may alternatively be any other resilient element that provides for friction-fit interference between the improved plunger and damper assembly 3160 and the inner-facing surface 931 of the circular cylindrical portion 906 of end cover 105.

It is a particular feature of an embodiment of the present invention that upon insertion of the rearward portion of the improved plunger and damper assembly 3160 into cylindrical volume 930 of generally circular cylindrical portion 906 of end cover 105, rearward dampening element 3174 is forced forwardly by frictional engagement with inner-facing surface 931 of generally circular cylindrical portion 906 of end cover 105 into engagement with the inclined surface 3262, thus positioning the rearward dampening element 3174 generally at rest. The positioning of the rearward dampening element 3174 adjacent the inclined surface 3262 (FIG. 5A, stage I) provides for a relatively low level of damping of axial motion of the improved plunger and damper assembly 3160 relative to the end cover 105 during rearward displacement of the improved plunger and damper assembly 3160.

It is appreciated from a consideration of enlargement B in FIG. 7B that air compressed behind rearward dampening element 3174 in generally circular cylindrical portion 906 of end cover 105 is vented to the atmosphere via mutually radially outwardly directed slots 3264 formed on inclined surface 3262 (FIGS. 2-5B), thus effectively preventing air pressure resistance and resulting in that no additional force is required for rearward displacement of the improved plunger and damper assembly 3160 in the direction indicated by arrow 3300. Were this air not to be released, it would resist required rearward motion of the improved plunger and damper assembly 3160.

It is a further particular feature of an embodiment of the present invention that relatively low force is required for displacement of the improved plunger and damper assembly 3160 relative to end cover 105 due to the fact that rearward dampening element 3174 engages inclined surface 3262, thus the profile of the rearward dampening element 3174 is minimized, causing lesser or no deformation of the rearward dampening element 3174, thus lesser contact surface between the rearward dampening element 3174 and the inner-facing surface 931 of the generally circular cylindrical portion 906 of end cover 105.

Due to the tilted geometry of the rearward damping control friction element seat 3260, friction forces resisting to charging of the auto-injection device 100 are minimized in comparison to a planar geometry of damping control friction element seat where the rearward dampening element 3174 engages a planar surface during rearward displacement of the plunger and damper assembly. Therefore, in accordance with an embodiment of the present invention, the user can apply a relatively low force on the charging mechanism in order to charge the auto injection device 100 having the improved plunger and damper assembly 3160.

Figure 8A:
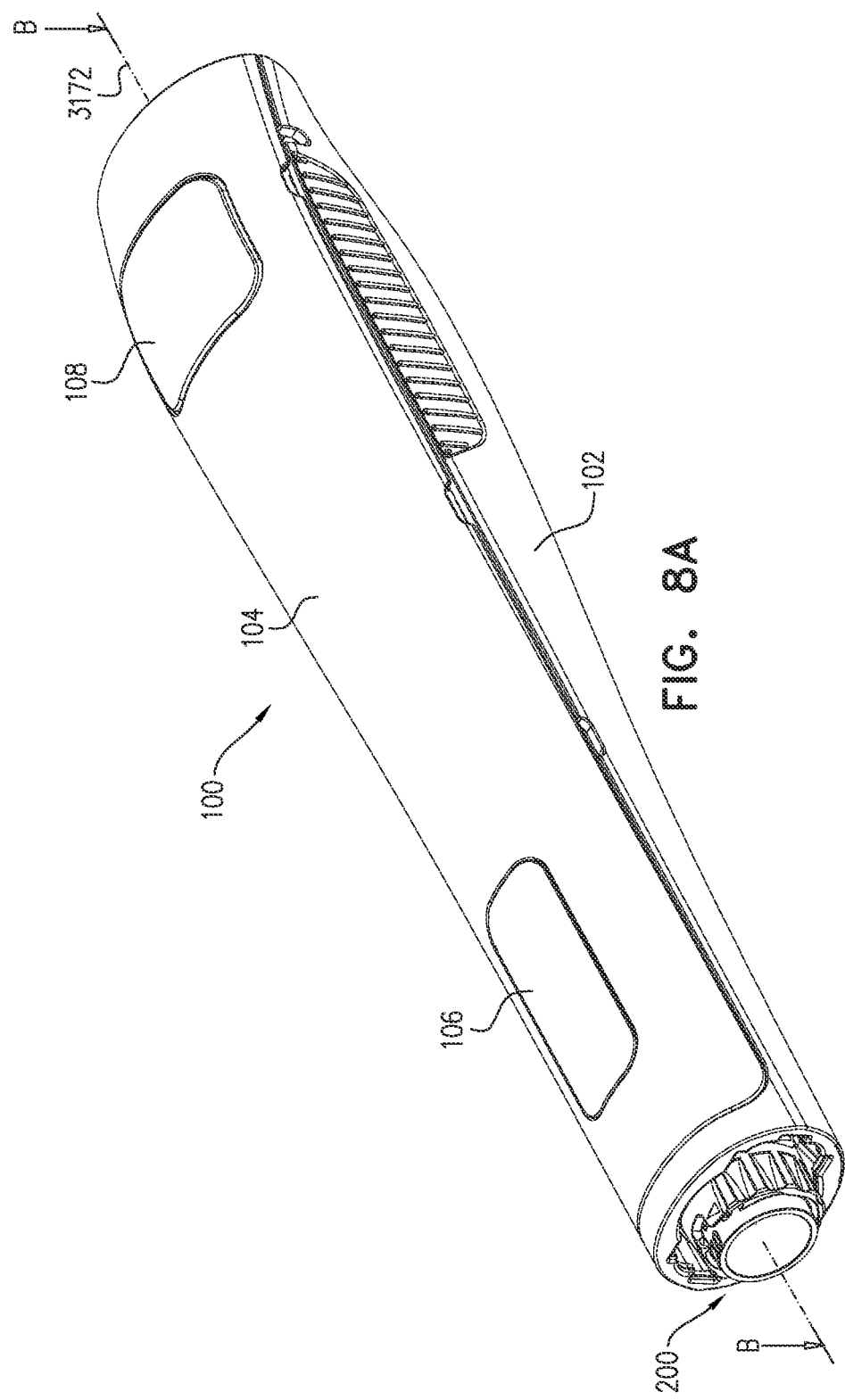
FIGS. 8A & 8B are respectively a simplified pictorial view and a sectional illustration of the automatic injection device with the medicament module of FIGS. 1A & 1B, where the improved plunger and damper assembly of FIG. 2 is forming part of the automatic injection device, section being taken along lines B-B in FIG. 8A, the automatic injection device is shown in an activated operative orientation.
Figure 8B:
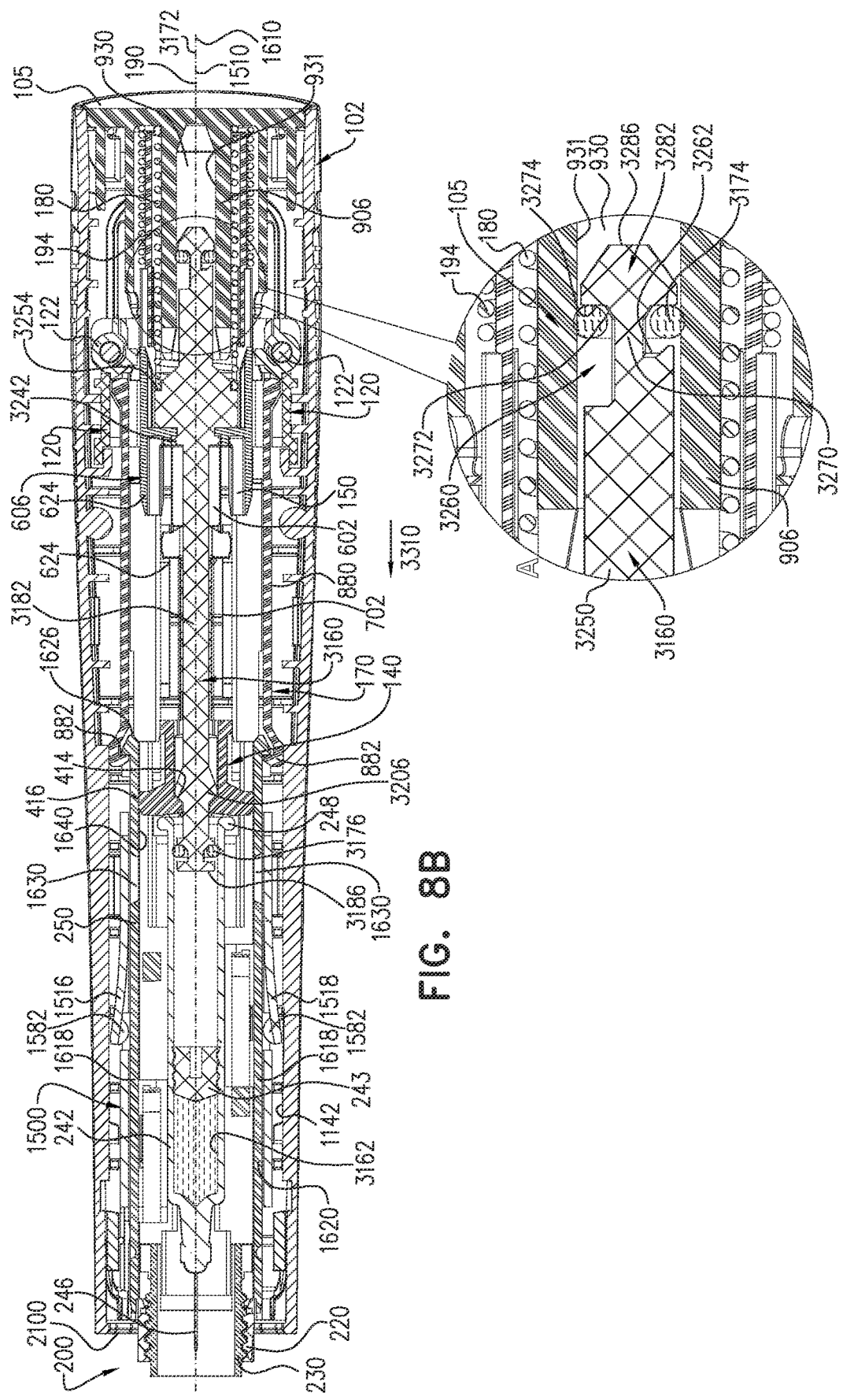

Reference is now made to FIGS. 8A & 8B, which are respectively a simplified pictorial view and a sectional illustration of the automatic injection device 100 with the medicament module 200 of FIGS. 1A & 1B, where the improved plunger and damper assembly 3160 of FIG. 2 is forming part of the automatic injection device 100, section being taken along lines B-B in FIG. 8A, the automatic injection device 100 is shown in an activated operative orientation.

It is noted that all components of the automatic injection device 100 are preferably identical to that shown in PCT Patent application PCT/IL2016/050929 and described therein, other than the improved plunger and damper assembly 3160, which is different from the elongate damping driver element 160 described in the PCT/IL2016/050929. The disclosure of PCT Patent application PCT/IL2016/050929 is hereby incorporated by reference.

It is also noted that the improved plunger and damper assembly 3160 is useful in various automatic injection devices, such as described in the following Published PCT Patent Applications, for example: WO2008/047372; WO2017/033193; WO2015/118550 or WO2014/174519.

It is seen in FIGS. 8B & 8C that in this activated operative orientation an axial force is applied onto the improved plunger and damper assembly 3160 by first compression spring 180 in a direction indicated by an arrow 3310.

It is seen in FIG. 8B that once the auto injection device 100 is activated, the plunger and damper assembly 3160 is slightly axially displaced forwardly along axis 3172 and the 3286 of the plunger and damper assembly 3160 is more forwardly displaced with respect to the rearward end of the cylindrical portion 906 as compared to FIG. 7C. The rearward dampening element 3174 is forced rearwardly towards the forwardly facing planar annular surface 3274 of the improved plunger and damper assembly 3160 and causing engagement thereof with the forwardly and outwardly tapered axial portion 3272. (FIG. 5A, stage II). The rearward dampening element 3174 is inserted in inner cylindrical volume 930 of generally circular cylindrical portion 906 of end cover 105, following forward displacement of the improved plunger and damper assembly 3160 relative to main housing portion 102 and cover portion 104.

It is appreciated from a consideration of enlargement A in FIG. 8B that engagement of rearward dampening element 3174 with the forwardly and outwardly tapered axial portion 3272 causes increased friction during forward displacement of the improved plunger and damper assembly 3160 thus dampening the forward displacement thereof as seen in stage II in FIGS. 5A & 5B. Upon engagement of rearward dampening element 3174 with the forwardly and outwardly tapered axial portion 3272, the profile of the rearward dampening element 3174 is maximized, causing more deformation of the rearward dampening element 3174, thus larger contact surface between the rearward dampening element 3174 and the inner-facing surface 931 of the generally circular cylindrical portion 906 of end cover 105, which in turn provides for increased friction forces therebetween.

It is further appreciated that during forward motion of the improved plunger and damper assembly 3160, a partial vacuum is created between rearward dampening element 3174 and the end cover 105, which enhances damping of forward axial motion of the improved plunger and damper assembly 3160 relative to the main housing portion 102.

It is a particular feature of an embodiment of the present invention that the enhanced friction and partial vacuum are configured for preventing damage to the syringe 242 and additional components of the automatic injection device 100 at the end of forward displacement of the improved plunger and damper assembly 3160 and additionally reduce noise during actuation of the automatic injection device 100.

It is particularly seen in FIG. 8B that during forward displacement of the improved plunger and damper assembly 3160, the rearward dampening element 3174 is forced rearwardly by frictional engagement with the inner-facing surface 931 of circular cylindrical portion 906 into engagement with tapered axial portion 3272 and planar annular surface 3274. This engagement forces rearward dampening element 3174 radially outwardly and thus increases its frictional engagement with the inner-facing surface 931 of circular cylindrical portion 906, thus providing a relatively high level of damping of forward axial motion of the improved plunger and damper assembly 3160 in forward direction, as indicated by arrow 3310. It is noted that the angle of tapered axial portion 3272 can be adjusted to achieve different levels of increase in the friction/dampening of the forward displacement of improved plunger and damper assembly 3160.

It is a particular feature of an embodiment of the present invention that the increased friction-fit interference between rearward dampening element 3174 and the inner-facing surface 931 of circular cylindrical portion 906 acts against the force of the first compression spring 180, thus reduces forward advancement speed of the improved plunger and damper assembly 3160 relative to syringe 242, thereby reducing the impact of the improved plunger and damper assembly 3160 on the piston 243 and thus minimizing the risk of breakage of syringe 242 and reduces the noise created by the impact.

It is seen in FIG. 8B that in this operative orientation the forwardly facing contact surface 3186 of the improved plunger and damper assembly 3160 does not yet engage piston 243.

It is a particular feature of an embodiment of the present invention that damping force can be achieved in at least one of the following ways: friction engagement between dampening element 3174 and the inner-facing surface 931 of circular cylindrical portion 906, vacuum, or a combination of both friction and vacuum.

Figure 9A:
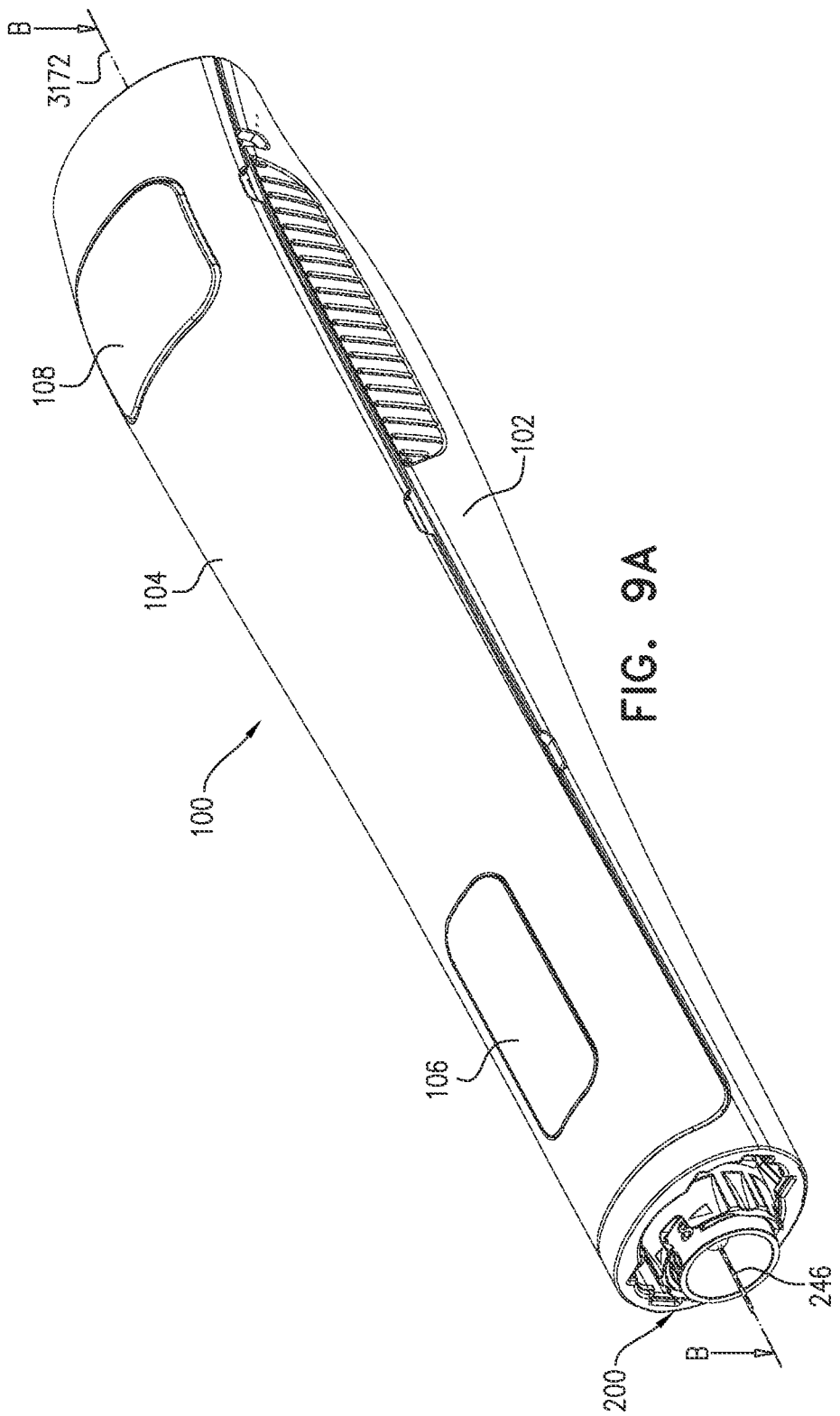
FIGS. 9A & 9B are respectively a simplified pictorial view and a sectional illustration of the automatic injection device with the medicament module of FIGS. 1A & 1B, where the improved plunger and damper assembly of FIG. 2 is forming part of the automatic injection device, section being taken along lines B-B in FIG. 9A, the automatic injection device is shown in a start of injection operative orientation.
Figure 9B:
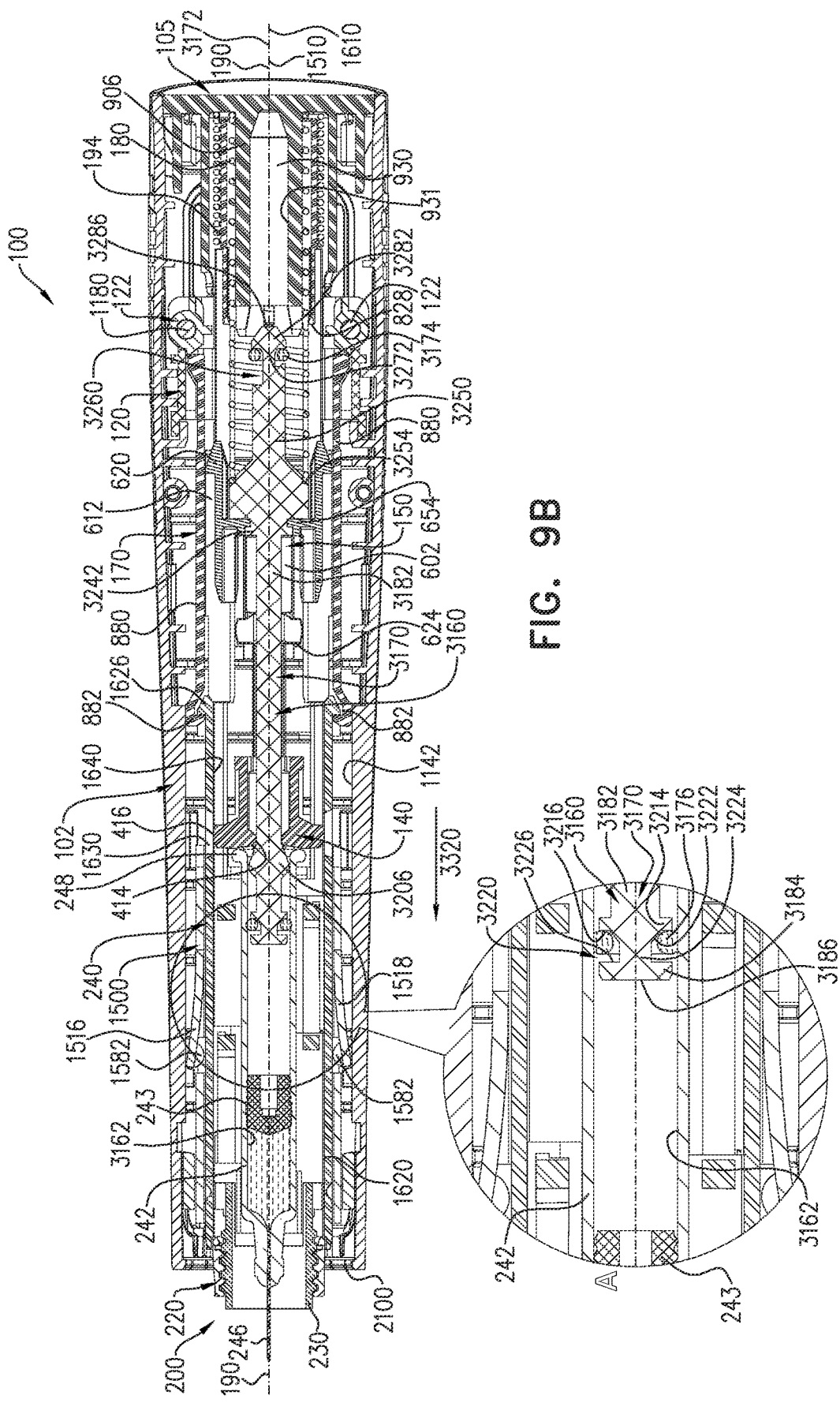

Reference is now made to FIGS. 9A & 9B, which are respectively a simplified pictorial view and a sectional illustration of the automatic injection device 100 with the medicament module 200 of FIGS. 1A & 1B, where the improved plunger and damper assembly 3160 of FIG. 2 is forming part of the automatic injection device 100, section being taken along lines B-B in FIG. 9A, the automatic injection device 100 is shown in a start of injection operative orientation.

It is noted that all components of the automatic injection device 100 are preferably identical to that shown in PCT Patent application PCT/IL2016/050929 and described therein, other than the improved plunger and damper assembly 3160, which is different from the elongate damping driver element 160 described in the PCT/IL2016/050929. The disclosure of PCT Patent application PCT/IL2016/050929 is hereby incorporated by reference.

It is also noted that the improved plunger and damper assembly 3160 is useful in various automatic injection devices, such as described in the following Published PCT Patent Applications, for example: WO2008/047372; WO2017/033193; WO2015/118550 or WO2014/174519.

It is seen specifically in FIG. 9B that there is no more friction-fit interference between the rearward dampening element 3174 and inner-facing surface 931 of the circular cylindrical portion 906, thus the rearward dampening element 3174 is no longer operative to act against the force of spring 180. It is appreciated that termination of damping force applied on the improved plunger and damper assembly 3160 by the rearward dampening element 3174 is dependent on the length of circular cylindrical portion 906, such that if the circular cylindrical portion 906 is longer than the damping force is effective for a longer period of time and a longer longitudinal displacement extent of the improved plunger and damper assembly 3160, thus the rearward dampening element 3174 could still be operative during a certain amount of time at the start of injection, when the forward end of the improved plunger and damper assembly 3160 is inserted into the syringe 242.

Alternatively, the forward dampening element 3176 is effective for further dampening the improved plunger and damper assembly 3160 at the start of injection operative orientation, as is described in detail hereinbelow.

It is noted that medicament module 200 is mounted into automatic injection device 100, as previously described with respect to FIG. 1A. The syringe 242 preferably having inner surface 3162. Needle 246 is preferably mounted to the forward end of syringe 242 and flange 248 is formed at the rearward end of the syringe 242. Piston 243 is positioned within syringe 242 and is configured to confine a medicament contained within syringe 242.

It is appreciated that, alternatively, any type of medicament container can be inserted into the automatic injection device 100 in accordance with an embodiment of the present invention, such as a cartridge for example, which has a septum in its forward end, which is configured to be pierced by a needle.

It is seen in FIG. 9B that in this start of injection operative orientation an axial force is applied onto the improved plunger and damper assembly 3160 by first compression spring 180 in a direction indicated by an arrow 3320, thus urging forward displacement of the improved plunger and damper assembly into syringe 242, such that forward side protrusions 3206 of the improved plunger and damper assembly 3160 is now disposed at least partially within the syringe 242.

It is a particular feature of an embodiment of the present invention that forward dampening element 3176 is mounted within forward damping control friction element seat 3220 of the improved plunger and damper assembly 3160 and the forward end of the improved plunger and damper assembly 3160 is inserted into syringe 242, such that forward dampening element 3176 is disposed in a friction-fit interference with the inner surface 3162 of the syringe 242.

It is a further particular feature of an embodiment of the present invention that the forward dampening element 3176 serves as a partial sealing element mounted onto the forward end of the plunger and damper body 3170 for creating an at least temporary slidable seal between the plunger and damper body 3170 and the inner cylindrical surface 3162 of the syringe 242.

It is particularly seen in FIG. 9B that during forward displacement of the improved plunger and damper assembly 3160, forward dampening element 3176 is urged into engagement to with forwardly tapered section 3222 of forward damping control friction element seat 3220 by means of friction-fit engagement of the forward dampening element 3176 with the inner surface 3162 of the syringe 242, as shown in stage I in FIG. 6A.

It is noted that in this particular embodiment of the present invention, the forward dampening element 3176 is an O-ring, however it may alternatively be any other resilient element that provides for friction-fit interference between the improved plunger and damper assembly 3160 and the inner surface 3162 of the syringe 242.

It is seen in FIG. 9B that in this operative orientation the contact portion 3186 of the improved plunger and damper assembly 3160 is rearwardly spaced from piston 243, such that there is no contact between the contact surface 3186 and the piston 243. It is noted that the forward end of the improved plunger and damper assembly can initially be rearwardly spaced from flange 248 of the syringe 242 or it may alternatively be slightly inserted into the syringe 242 and forwardly spaced from flange 248.

Engagement of forward dampening element 3176 with tapered axial portion 3222 forces forward dampening element 3176 radially outwardly, thus partially seals the volume between forward dampening element 3176 and the piston 243, thereby causing pressure build-up therebetween and further enhances level of damping of axial motion of the improved plunger and damper assembly 3160 relative to syringe 242 in forward motion thereof.

It is noted that protrusion 3230 partially separates the forward dampening element 3176 from forwardly facing surface 3216 and thus provides for a small air passage, which in turn enables at least partial seal breakage between the forward dampening element 3176 and the piston 243 in order to allow air to escape in a rate which is slower than the rate of the pressure build-up. Allowing the air to escape enables engagement of the contact surface 3186 with piston 243 during forward displacement of the improved plunger and damper assembly 3160. The release of the air-pressure may occur prior to starting of the medicament injection, during the medicament injection, at the end of medicament injection, or even not released at all, depending on the size of protrusion 3230, or eliminating this protrusion at all.

It is further noted that in accordance with an alternative embodiment of the present invention, there is no such protrusion 3230 on the improved plunger and damper assembly 3160, thus air remains trapped between the forward dampening element 3176 and the piston 243, thus pressure continuously builds-up and forward displacement of the improved plunger and damper assembly 3160 urges forward displacement of the piston 243 through an air-spring formed therebetween, without any mechanical engagement between the contact surface 3186 and the piston 243.

It is appreciated that, as seen in FIG. 9B, engagement of forward dampening element 3176 with the forwardly tapered section 3222 causes increased friction during forward displacement of the improved plunger and damper assembly 3160 thus dampening the forward displacement thereof as seen in stage I in FIGS. 6A & 6B. Upon engagement of forward dampening element 3176 with the forwardly tapered section 3222, the profile of the forward dampening element 3176 is maximized, causing more deformation of the forward dampening element 3176, thus larger contact surface between the forward dampening element 3176 and the inner surface 3162 of the syringe 242, which in turn provides for increased friction forces therebetween, which acts against the force of the first compression spring 180. Forward dampening element 3176 thus reduces the forward advancement speed of the improved plunger and damper assembly 3160 relative to the syringe 242, thereby reducing the impact of the improved plunger and damper assembly 3160 on the piston 243 and thus minimizing the risk of breakage of syringe 242 and the noise created by the impact.

It is a particular feature of an embodiment of the present invention that axial forward insertion of the plunger and damper body 3170 with the forward dampening element 3176 into the syringe 242 creates friction between the forward dampening element 3176 and the inner surface 3162 of the syringe 242 and also creates an at least temporary air spring between the forward dampening element 3176 and the piston 243, wherein the friction and the air spring dampen motion of the plunger and damper body 3170.

It is noted that the angle of forwardly tapered section 3222 can be adjusted to achieve different levels of increase in the friction/dampening.

In accordance with this embodiment, air is trapped between the forward dampening element 3176 and the piston 243, since the forward dampening element 3176 is disposed in a sealing relationship with the inner surface 3162 of the syringe 242. It is a particular feature of this embodiment of the present invention that upon forward displacement of the improved plunger and damper assembly 3160 under the force of spring 180, the pressure between the forward dampening element 3176 and the piston 243 builds up, thus causing advancement of piston 243 relative to syringe 242 without any mechanical contact between the contact surface 3186 of the improved plunger and damper assembly 3160 and the piston 243. It is noted that in accordance with an embodiment of the present invention, the injection of medicament contained within syringe 242 may begin before engagement of the improved plunger and damper assembly 3160 and the piston 243.

Figure 10B:
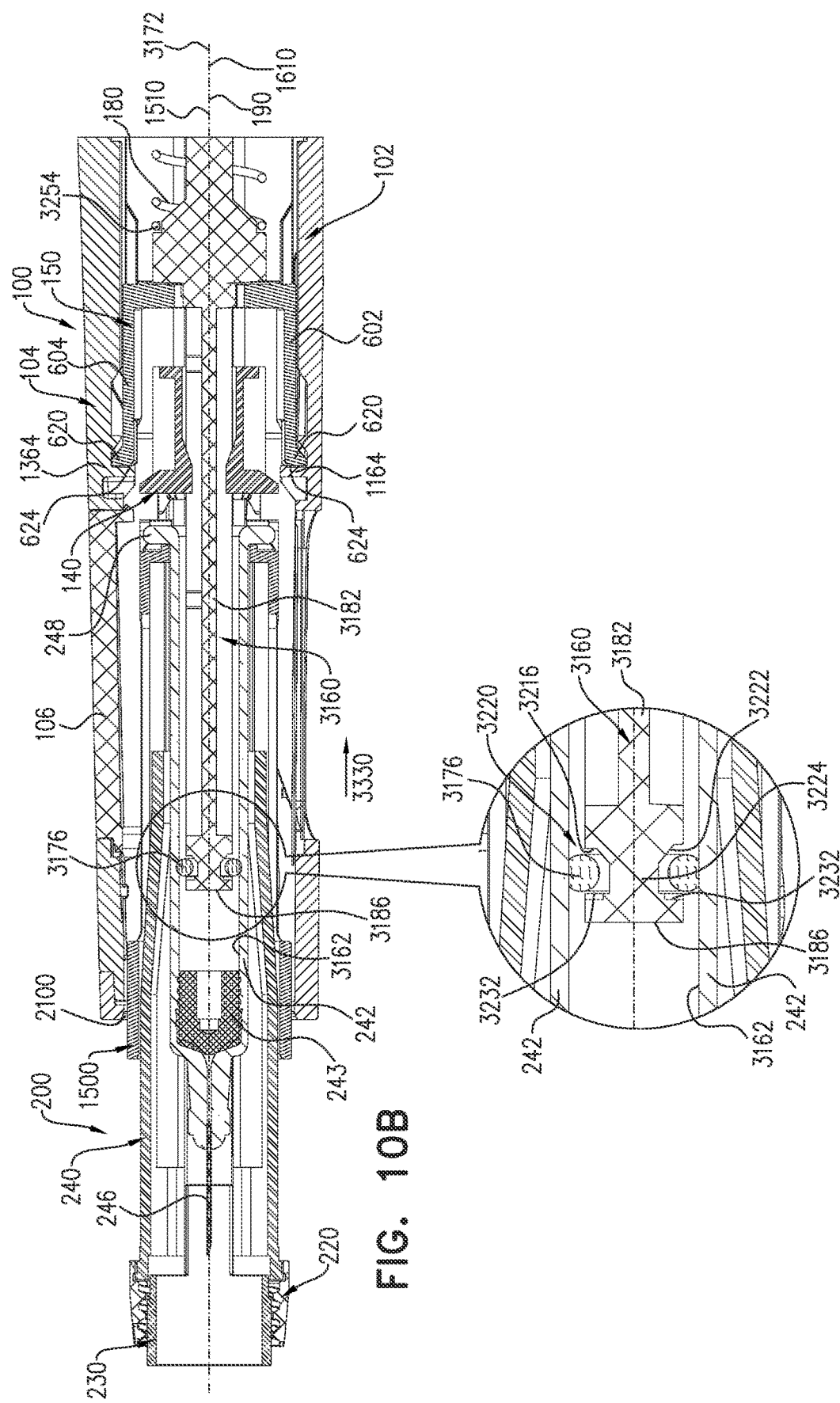
Figure 10C:
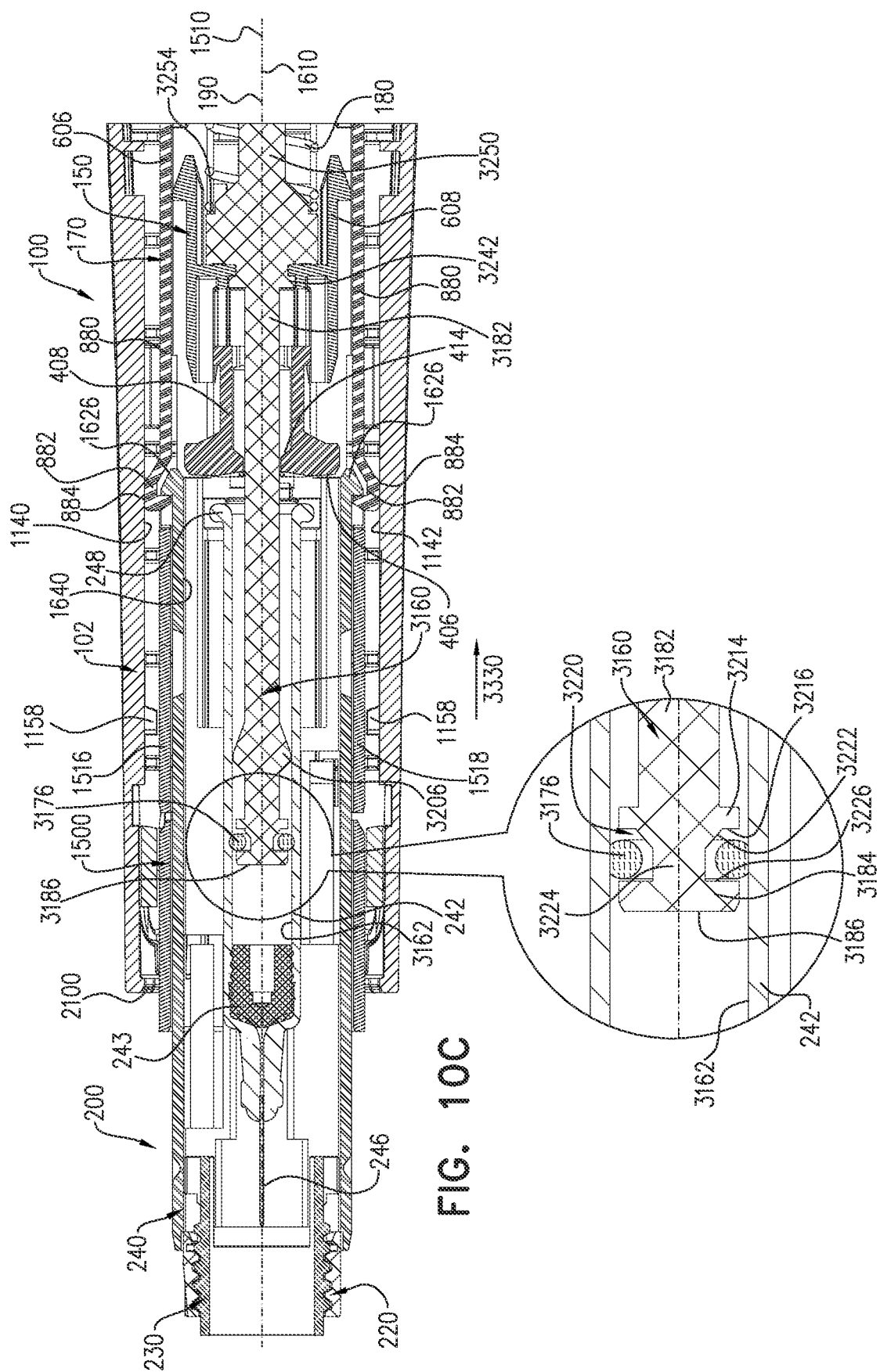

Reference is now made to FIGS. 10A-10C, which are respectively a simplified pictorial view and two orthogonal sectional illustrations of the automatic injection device 100 with the medicament module 200 of FIGS. 1A & 1B, where the improved plunger and damper assembly 3160 of FIG. 2 is forming part of the automatic injection device 100, sections being taken along lines B-B and C-C in FIG. 10A, the automatic injection device 100 is shown in a removal from the injection site operative orientation.

It is noted that all components of the automatic injection device 100 are preferably identical to that shown in PCT Patent application PCT/IL2016/050929 and described therein, other than the improved plunger and damper assembly 3160, which is different from the elongate damping driver element 160 described in the PCT/IL2016/050929. The disclosure of PCT Patent application PCT/IL2016/050929 is hereby incorporated by reference.

It is also noted that the improved plunger and damper assembly 3160 is useful in various automatic injection devices, such as described in the following Published PCT Patent Applications, for example: WO2008/047372; WO2017/033193; WO2015/118550 or WO2014/174519.

It is seen in FIGS. 10A & 10B that the entire amount of medicament is ejected from the syringe 242 and the piston 243 is disposed at the forwardmost end of the syringe 242. The medicament module 200 is in the process of removal from the automatic injection device 100 in this operative orientation, thus the medicament module 200, including the syringe 242, are displaced forwardly with respect to the improved plunger and damper assembly 3160, and as a result the improved plunger and damper assembly 3160 becomes more rearwardly spaced from the piston 243, as indicated by an arrow 3330.

It is a particular feature of an embodiment of the present invention that forward dampening element 3176 is mounted within forward damping control friction element seat 3220 of the improved plunger and damper assembly 3160 and the forward end of the improved plunger and damper assembly 3160 is still inserted into syringe 242, such that forward dampening element 3176 is disposed in a friction-fit interference with the inner surface 3162 of the syringe 242.

It is particularly seen in FIG. 10B that during forward displacement of the medicament module 200 relative to the improved plunger and damper assembly 3160, forward dampening element 3176 is urged into engagement with rearwardly facing surface 3226 of forward damping control friction element seat 3220 by means of friction-fit engagement of the forward dampening element 3176 with the inner surface 3162 of the syringe 242, as shown in stage II in FIGS. 6A & 6B.

It is noted that in this particular embodiment of the present invention, the forward dampening element 3176 is an O-ring, however it may alternatively be any other resilient element that provides for friction-fit interference between the improved plunger and damper assembly 3160 and the inner surface 3162 of the syringe 242.

It is seen in FIG. 10B that in this operative orientation the piston 243 is more forwardly spaced from the contact portion 3186 of the improved plunger and damper assembly 3160 in comparison with FIG. 9B, such that there is no contact between the contact surface 3186 and the piston 243.

It is a particular feature of an embodiment of the present invention that when the medicament module 200 is displaced forwardly with respect to the improved plunger and damper assembly 3160, air can be released from the space between the contact portion 3186 and the piston 243 through recess 3232 thus relieving air pressure within this space and minimizing the air pressure resistance for removing the medicament module 200 from the automatic injection device 100.

It is appreciated that, as seen in FIG. 10B, engagement of forward dampening element 3176 with the rearwardly facing surface 3226 of forward damping control friction element seat 3220 decreases the amount of friction forces during forward displacement of the medicament module 200 relative to the improved plunger and damper assembly 3160 as seen in stage II in FIGS. 6A & 6B. Upon engagement of forward dampening element 3176 with the rearwardly facing surface 3226 of forward damping control friction element seat 3220, clearance is formed underneath the forward dampening element 3176, which causes minimization of the forward dampening element 3176 profile. Profile minimization or shrinkage of the forward dampening element 3176 provides for smaller contact surface between the forward dampening element 3176 and the inner surface 3162 of the syringe 242, which in turn provides for lower friction forces therebetween, which facilitates removal of the medicament module 200 from the automatic injection device 100.

Figure 11A:
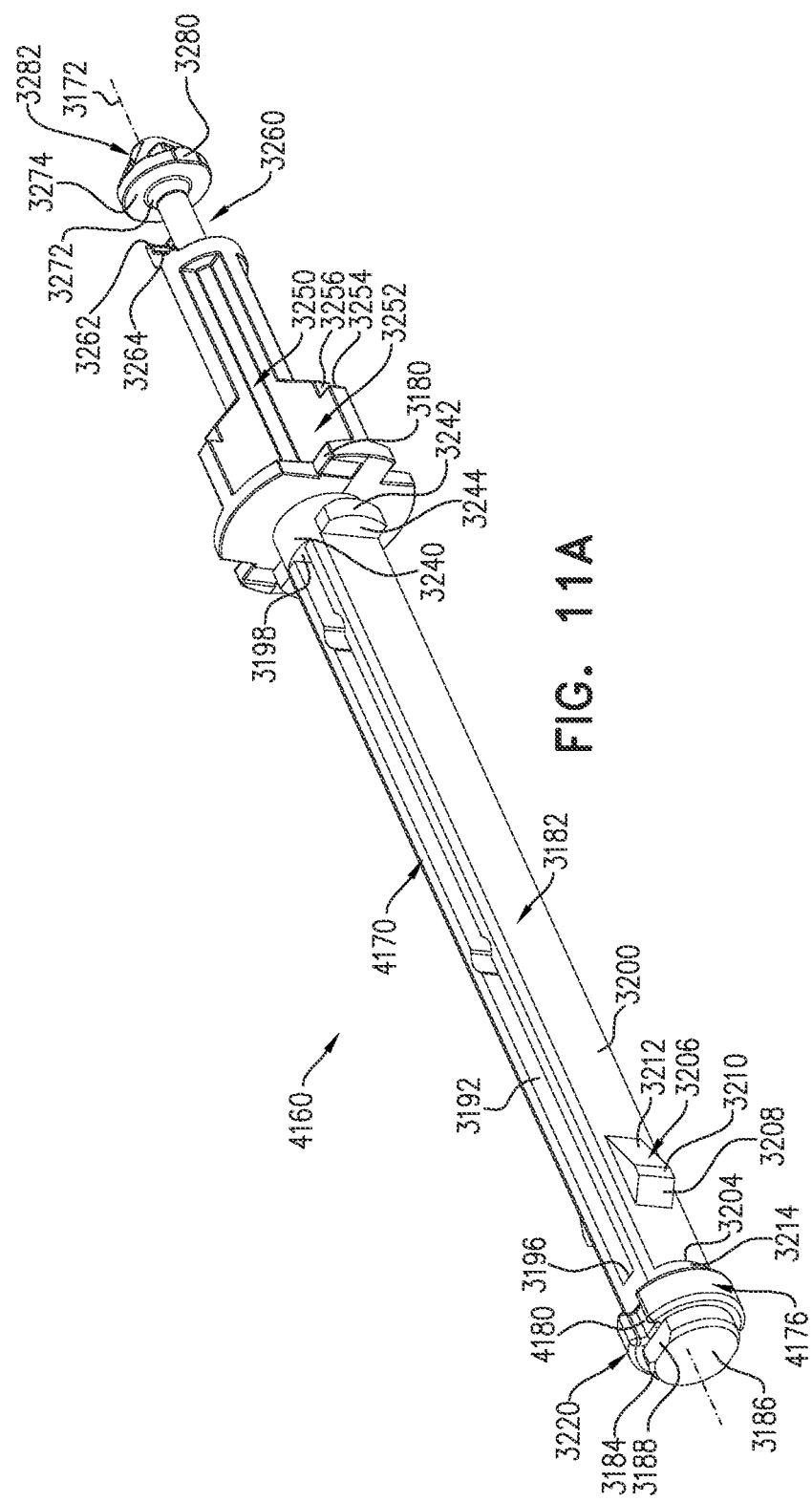

Reference is now made to FIGS. 11A-11C, which are respectively a simplified pictorial illustration, a side view and a sectional illustration of an improved plunger and damper assembly useful in various automatic injection devices, such as shown in FIGS. 1A & B and constructed and operative in accordance with another embodiment of the present invention, section being taken along lines C-C in FIG. 11B.

An improved plunger and damper assembly 4160 having a plunger and damper body 4170 is seen in FIGS. 11A-11C, being constructed and operative in accordance with another embodiment of the present invention. It is noted that the improved plunger and damper assembly 4160 is preferably identical in all respects to the improved plunger and damper assembly 3160 as shown and described with respect to FIGS. 2-4C hereinabove and identical reference numerals are used to indicate identical parts of the improved plunger and damper assembly 3160 and 4160, with the exception of the following:

Instead of the forward dampening element 3176 in a form of an O-ring, a generally annular forward resilient dampening element 4176 is formed at a forward end of the plunger and damper body 4170, within forward damping control friction element seat 3220, typically adjacent the contact surface 3186 and being typically formed by overmolding. It is noted that the forward resilient dampening element 4176 extends radially outwardly with respect to the outer surface of longitudinal rod 3182 of the plunger and damper body 4170.

It is noted that the annular forward resilient dampening element 4176 is generally fixedly attached to the plunger and damper body 4170 and radially extends outwardly with respect to the circumference of the plunger and damper body 4170.

It is further seen in FIGS. 11A-11C that at least one channel 4180 is formed in forward resilient dampening element 4176 and extends generally longitudinally from circular cylindrical portion 3184 towards the half-circular section 3214. The circular cylindrical portion 3184 preferably includes flat wall surface 3188, which is generally aligned with channel 4180.

It is noted that, alternatively, series of forward resilient dampening elements 4176 can be formed at the forward end of longitudinal rod 3182 of the plunger and damper body 4170.

It is further noted that, alternatively, the forward resilient dampening element 4176 can be formed without channel 4180.

It is a particular feature of an embodiment of the present invention that forward resilient dampening element 4176 is integrally formed with the plunger and damper body 4170 and is configured to be inserted into syringe 242 such that forward resilient dampening element 4176 is disposed in a friction-fit interference with the inner surface 3162 of the syringe 242.

It is noted that the forward resilient dampening element 4176 is configured to be deformed and thus provide a friction force, as shown with respect to forward dampening element 3176 both during forward and rearward displacement of the improved plunger and damper assembly 4160.

Specifically, when the improved plunger and damper assembly 4160 is mounted within the automatic injection device 100 in a start of injection operative orientation as shown in FIGS. 9A & 9B, and the improved plunger and damper assembly 4160 is adapted to be forwardly displaced along axis 3172, the forward resilient dampening element 4176 is disposed in a friction-fit engagement with the inner surface 3162 of the syringe 242 and provides damping of the forward displacement of the improved plunger and damper assembly 4160 relative to the syringe 242. Such damping reduces the impact of the improved plunger and damper assembly 4160 on the piston 243 and thus minimizing the risk of breakage of the syringe 242 and the noise created by the impact.

It is an additional embodiment of the present invention that the forward dampening element 4176 further enables dampening the movement of the improved plunger and damper assembly 3160 before engagement between the improved plunger and damper assembly 4160 and the piston 243, thereby minimizing the risk of syringe breakage, even if the improved plunger and damper assembly 4160 has to travel a substantial distance up until engagement with the piston 243, such as in case of injecting a low volume dosage of medication, such as under 1.5 ml, for example.

It is a further particular feature of an embodiment of the present invention that during forward displacement of the improved plunger and damper assembly 4160 relative the syringe 242, as shown in FIGS. 9A & 9B, the forward resilient dampening element 4176 is deformed due to its axial displacement along the inner surface 3162 of the syringe 242. The deformation of the forward resilient dampening element causes enhanced friction between the improved plunger and damper assembly 4176 and the syringe 242, thus providing a relatively high level of damping of axial motion of the improved plunger and damper assembly 4160 in forward motion.

It is a further particular feature of an embodiment of the present invention that during forward displacement of the improved plunger and damper assembly 4160, air pressure is created between forward resilient dampening element 4176 and the inner surface 3162 of the syringe 242, which enhances damping of forward axial displacement of the improved plunger and damper assembly 4160 relative to the syringe 242.

It is a particular feature of an embodiment of the present invention that axial forward insertion of the plunger and damper body 4170 with the forward dampening element 4176 into the syringe 242 creates friction between the forward dampening element 4176 and the inner surface 3162 of the syringe 242 and also creates an at least temporary air spring between the forward dampening element 4176 and the piston 243, wherein the friction and the air spring dampen motion of the plunger and damper body 4170.

In accordance with an embodiment of the present invention, air can be released from the space formed between the forward dampening element 4176 and the piston 243 via channel 4180.

It is noted that in accordance with an alternative embodiment of the present invention, there is no channel 4180 provided in forward dampening element 4176. According to this embodiment, air is trapped between the forward dampening element 4176 and the piston 243, since the forward dampening element 4176 is disposed in a sealing relationship with the inner surface 3162 of the syringe 242. It is a particular feature of this alternative embodiment of the present invention that upon forward displacement of the improved plunger and damper assembly 4160 under the force of spring 180, the pressure between the forward dampening element 4176 and the piston 243 builds up, thus causing advancement of piston 243 relative to syringe 242 without any mechanical contact between the contact surface 3186 of the plunger and damper body 4170 and the piston 243. It is noted that in accordance with an embodiment of the present invention, the injection of medicament contained within syringe 242 may begin before engagement of the improved plunger and damper assembly 4160 and the piston 243.

When the improved plunger and damper assembly 4160 is mounted within the automatic injection device 100 in the removal from the injection site operative orientation as shown in FIGS. 10A-10C, and the improved plunger and the syringe 242 is displaced forwardly relative to the damper assembly 4160, the forward resilient dampening element 4176 is still disposed in a friction-fit engagement with the inner surface 3162 of the syringe 242.

It is noted that the air release is dependent on the existence and size of channel 4180. In an alternative embodiment, the channel 4180 may be eliminated from the forward resilient dampening element 4176.

Figure 12A:
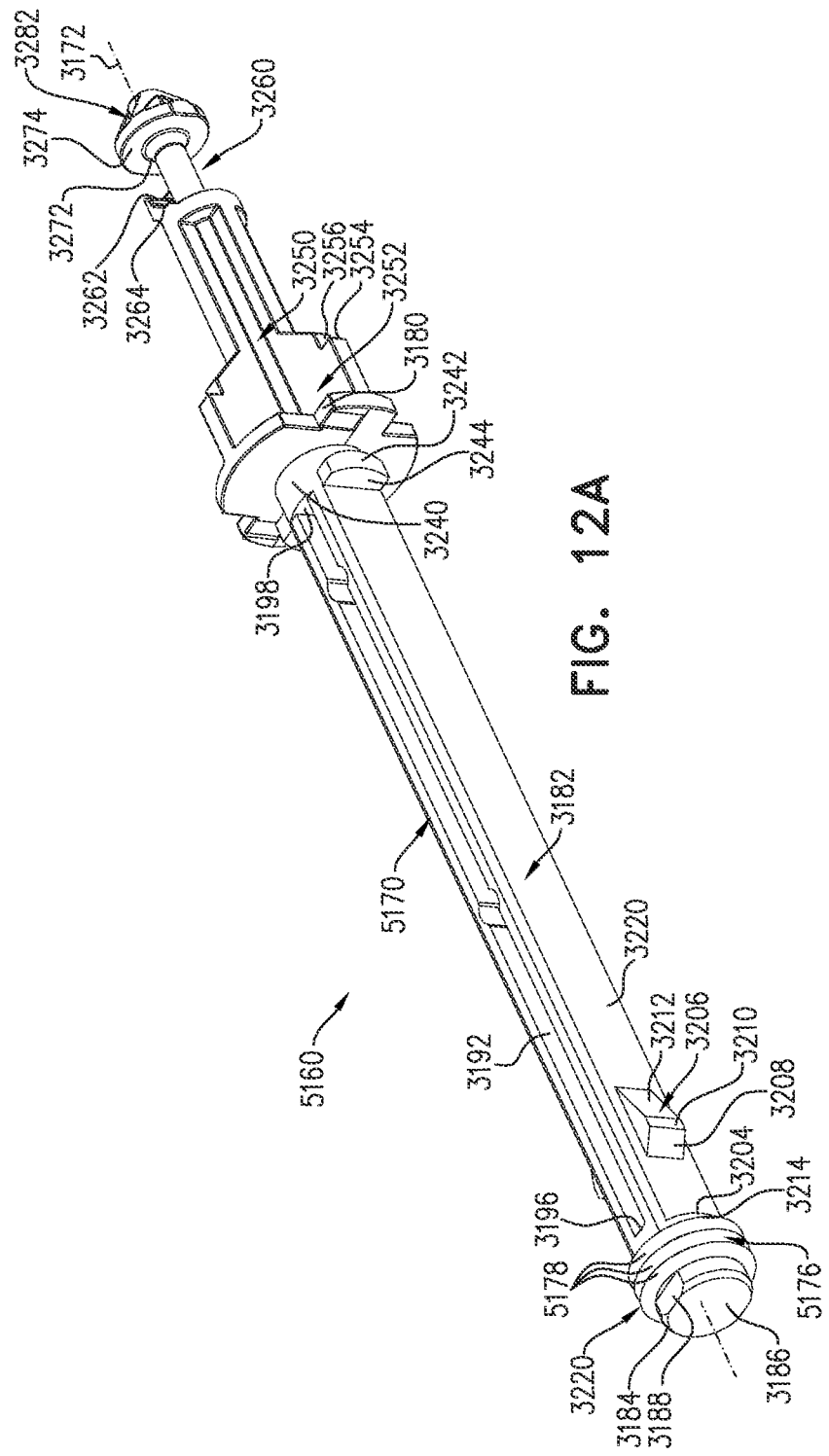

Reference is now made to FIGS. 12A-12C, which are respectively a simplified pictorial illustration, a side view and a sectional illustration of an improved plunger and damper assembly useful in various automatic injection devices, such as shown in FIGS. 1A & B and constructed and operative in accordance with still another embodiment of the present invention, section being taken along lines C-C in FIG. 12B.

An improved plunger and damper assembly 5160 having a plunger and damper body 5170 is seen in FIGS. 12A-12C, being constructed and operative in accordance with another embodiment of the present invention. It is noted that the improved plunger and damper assembly 5160 is preferably identical in all respects to the improved plunger and damper assembly 4160 as shown and described with respect to FIGS. 11A-11C hereinabove and identical reference numerals are used to indicate identical parts of the improved plunger and damper assembly 4160 and 5160, with the exception of the following:

Instead of the forward dampening element 4176 in a form of generally annular forward resilient dampening element, a generally rubber-edged blade set forward resilient dampening element 5176 is formed at a forward end of the plunger and damper body 5170, within forward damping control friction element seat 3220, typically adjacent the contact surface 3186 and being typically formed by overmolding. It is noted that the rubber-edged blade set forward resilient dampening element 5176 extends radially outwardly with respect to the outer surface of longitudinal rod 3182 of the plunger and damper body 5170.

It is noted that the forward resilient dampening element 5176 is generally fixedly attached to the plunger and damper body 5170 and radially extends outwardly with respect to the circumference of the plunger and damper body 5170.

It is further seen in FIGS. 12A-12C that the rubber-edged blade set forward resilient dampening element 5176 preferably includes one more circular resilient portions 5178, which are generally axially spaced apart one from another and extends generally longitudinally from circular cylindrical portion 3184 towards the half-circular section 3214.

It is noted that, alternatively, series of rubber-edged blade set forward resilient dampening element 5176 can be formed at the forward end of longitudinal rod 3182 of the plunger and damper body 5170.

It is a particular feature of an embodiment of the present invention that rubber-edged blade set forward resilient dampening element 5176 is integrally formed with the plunger and damper body 5170 and is configured to be inserted into syringe 242 such that forward resilient dampening element 5176 is disposed in a friction-fit interference with the inner surface 3162 of the syringe 242.

It is noted that flat wall surface 3188 is provided in the cylindrical portion 3184 of plunger and damper body 5170, thus forming a recess therein. Corresponding recess may be provided on the resilient portions 5178, or the resilient portions 5178 may be not fully-circumferential, leaving passage for air, and thus air which would otherwise be trapped between the contact surface 3186 and the piston 243 of the syringe 242 is released via these recesses.

It is noted that the rubber-edged blade set forward resilient dampening element 5176 is configured to be deformed and thus provide a friction force both during forward and rearward displacement of the improved plunger and damper assembly 5160. The forward resilient dampening element 5176 at least temporarily seals the volume therebetween and between the piston 243, thus creating pressure build-up between the forward resilient dampening element 5176 and the piston 243. Upon reaching a sufficient pressure level, the forward resilient dampening element 5176 is deformed such that the resilient portions 5178 are deflected inwardly, thus allow partial air release from the volume enclosed between the forward resilient dampening element 5176 and the piston 243.

Specifically, when the improved plunger and damper assembly 5160 is mounted within the automatic injection device 100 in a start of injection operative orientation as shown in FIGS. 9A & 9B, and the improved plunger and damper assembly 5160 is adapted to be forwardly displaced along axis 3172, the rubber-edged blade set forward resilient dampening element 5176 is disposed in a friction-fit engagement with the inner surface 3162 of the syringe 242 and provides damping of the forward displacement of the improved plunger and damper assembly 5160 relative to the syringe 242. Such damping reduces the impact of the improved plunger and damper assembly 5160 on the piston 243 and thus minimizing the risk of breakage of the syringe 242 and the noise created by the impact.

It is an additional embodiment of the present invention that the forward dampening element 5176 further enables dampening the movement of the improved plunger and damper assembly 5160 before engagement between the improved plunger and damper assembly 5160 and the piston 243, thereby minimizing the risk of syringe breakage, even if the improved plunger and damper assembly 5160 has to travel a substantial distance up until engagement with the piston 243, such as in case of injecting a low volume dosage of medication, such as under 1.5 ml, for example.

It is a further particular feature of an embodiment of the present invention that during forward displacement of the improved plunger and damper assembly 5160 relative the syringe 242, as shown in FIGS. 9A & 9B, the resilient portions 5178 of rubber-edged blade set forward resilient dampening element 5176 are deformed due to their axial displacement along the inner surface 3162 of the syringe 242. The deformation of resilient portions 5178 of the rubber-edged blade set forward resilient dampening element 5176 causes enhanced friction between the improved plunger and damper assembly 5176 and the syringe 242, thus providing a relatively high level of damping of axial motion of the improved plunger and damper assembly 5160 in forward motion.

It is a particular feature of an embodiment of the present invention that axial forward insertion of the plunger and damper body 5170 with the forward dampening element 5176 into the syringe 242 creates friction between the forward dampening element 5176 and the inner surface 3162 of the syringe 242 and also creates an at least temporary air spring between the forward dampening element 5176 and the piston 243, wherein the friction and the air spring dampen motion of the plunger and damper body 5170.

It is a further particular feature of an embodiment of the present invention that during forward displacement of the improved plunger and damper assembly 5160, air pressure is created between rubber-edged blade set forward resilient dampening element 5176 and the piston 243, which enhances damping of forward axial displacement of the improved plunger and damper assembly 5160 relative to the syringe 242. When the improved plunger and damper assembly 5160 is mounted within the automatic injection device 100 in the removal from injection site operative orientation as shown in FIGS. 10A-10C, and the syringe 242 is forwardly displaced relative to the improved plunger and damper assembly 5160 along axis 3172, the rubber-edged blade set forward resilient dampening element 5176 is still disposed in a friction-fit engagement with the inner surface 3162 of the syringe 242.

It is noted that air pressure between the plunger and damper body 5170 and the piston 243 can be released by inward deflection of resilient portions 5178 during injection of medicament.

Figure 13A:
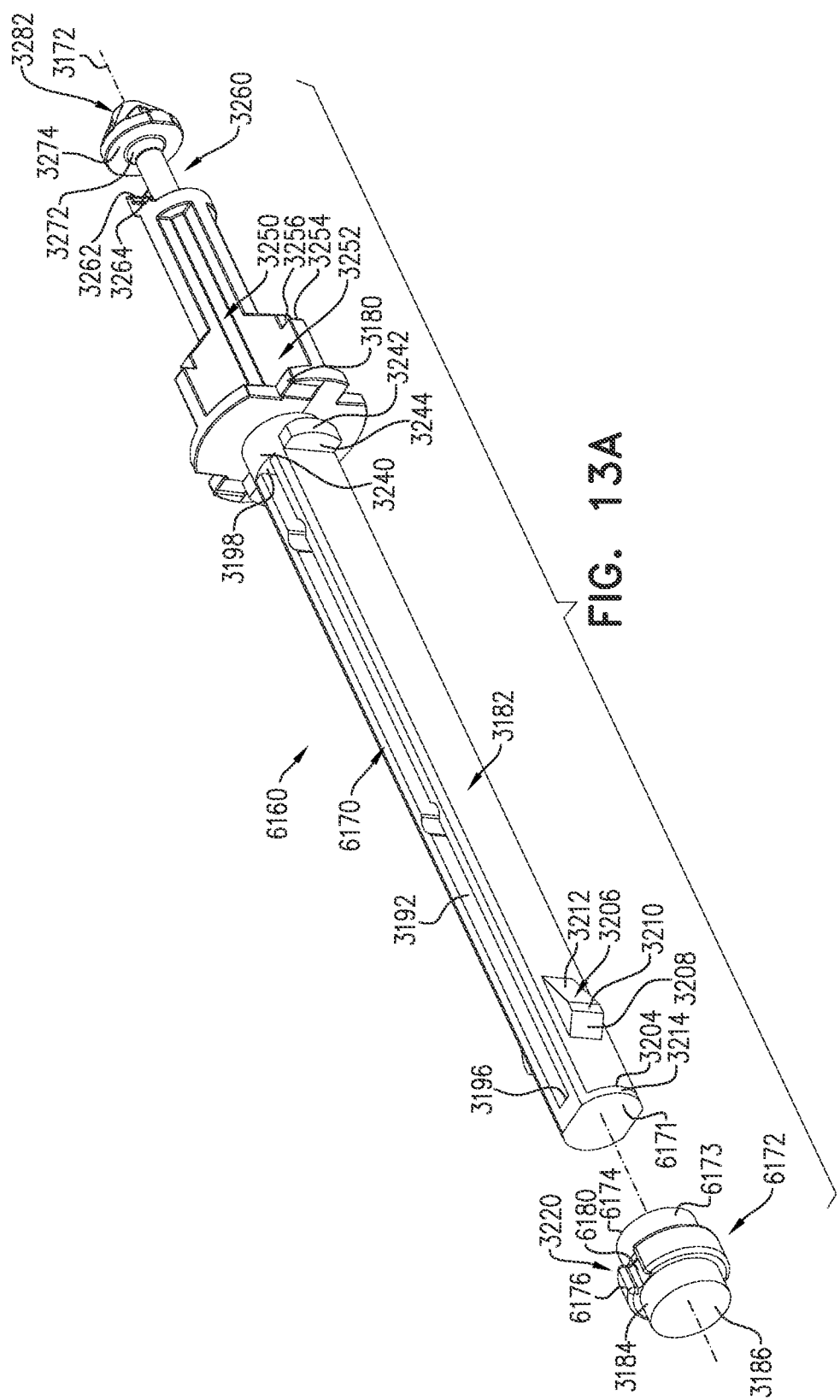

Reference is now made to FIGS. 13A-13C, which are respectively a simplified pictorial illustration, a side view and a sectional illustration of an improved plunger and damper assembly useful in various automatic injection devices, such as shown in FIGS. 1A & B and constructed and operative in accordance with yet another embodiment of the present invention, section being taken along lines C-C in FIG. 13B.

An improved plunger and damper assembly 6160 having a plunger and damper body 6170 is seen in FIGS. 13A-13C, being constructed and operative in accordance with another embodiment of the present invention. It is noted that the improved plunger and damper assembly 6160 is preferably identical in all respects to the improved plunger and damper assembly 4160 as shown and described with respect to FIGS. 11A-11C hereinabove and identical reference numerals are used to indicate identical parts of the improved plunger and damper assembly 4160 and 6160, with the exception of the following:

The improved plunger and damper assembly 6160 is not integrally made, rather it includes a plunger and damper body 6170 having a forwardly facing surface 6171 and a separate forward dampening portion 6172 having a cylindrical rod portion 6173 and a rearwardly facing surface 6174. A generally annular forward resilient dampening element 6176 is formed at the forward dampening portion 6172 of the improved plunger and damper assembly 6160, within forward damping control friction element seat 3220, typically adjacent the contact surface 3186 and being typically formed by overmolding. It is noted that the forward resilient dampening element 6176 extends radially outwardly with respect to the outer surface of cylindrical rod portion 6173 of the forward dampening portion 6172.

It is further seen in FIGS. 13A-13C that at least one channel 6180 is formed in forward resilient dampening element 6176 and extends generally longitudinally along the forward resilient dampening element 6176.

It is noted that the annular forward resilient dampening element 6176 is generally fixedly attached to the forward dampening portion 6172 and radially extends outwardly with respect to the circumference of the forward dampening portion 6172.

It is noted that, alternatively, series of forward resilient dampening elements 6176 can be formed at the forward dampening portion 6172 of the improved plunger and damper assembly 6160.

It is further noted that, alternatively, the forward resilient dampening element 6176 can be formed without channel 6180.

It is a particular feature of an embodiment of the present invention that both the plunger and damper body 6170 and the forward dampening portion 6172 with forward resilient dampening element 6176 are configured to be inserted into syringe 242 such that forward resilient dampening element 6176 is disposed in a friction-fit interference with the inner surface 3162 of the syringe 242.

It is a particular feature of an embodiment of the present invention that a forward dampening portion 6172 is disposed within the syringe 242 between the piston 243 and the plunger and damper body 6170 and is spaced apart from both the piston 243 and the forwardly facing surface 6171 of the plunger and damper body 6170. The forward end of the plunger and damper body 6170 is inserted into syringe 242, and the forward dampening portion 6172 is disposed forwardly thereof and in a friction-fit interference with the inner surface 3162 of syringe 242.

When the improved plunger and damper assembly 6160 is mounted within the automatic injection device 100 in a start of injection operative orientation as shown in FIGS. 9A & 9B, and the improved plunger and damper assembly 6160 is adapted to be forwardly displaced along axis 3172, the forward resilient dampening element 6176 is disposed in a friction-fit engagement with the inner surface 3162 of the syringe 242 and provides damping of the forward displacement of the improved plunger and damper assembly 6160 relative to the syringe 242. Such damping reduces the impact of the improved plunger and damper assembly 6160 on the piston 243 and thus minimizing the risk of breakage of the syringe 242 and the noise created by the impact.

It is an additional embodiment of the present invention that the forward dampening element 6176 further enables dampening the movement of the improved plunger and damper assembly 6160 before engagement between the improved plunger and damper assembly 6160 and the piston 243, thereby minimizing the risk of syringe breakage, even if the improved plunger and damper assembly 6160 and the forward dampening portion 6172 has to travel a substantial distance up until engagement with the piston 243, such as in case of injecting a low volume dosage of medication, such as under 1.5 ml, for example.

It is a further particular feature of an embodiment of the present invention that during forward displacement of the improved plunger and damper assembly 6160 relative the syringe 242, as shown in FIGS. 9A & 9B, the forward resilient dampening element 6176 provides friction forces due to its axial displacement along the inner surface 3162 of the syringe 242. The forward resilient dampening element 6176 provides for damping of axial motion of the improved plunger and damper assembly 6160 in forward motion.

It is a further particular feature of an embodiment of the present invention that in absence of channel 6180, air pressure is created between forward resilient dampening element 6176 and the piston 243 during forward displacement of the improved plunger and damper assembly 6160, which enhances damping of forward axial displacement of the improved plunger and damper assembly 6160 relative to the syringe 242.

It is a particular feature of an embodiment of the present invention that axial forward insertion of the plunger and damper body 6170 with the forward dampening element 6176 into the syringe 242 creates friction between the forward dampening element 6176 and the inner surface 3162 of the syringe 242 and also creates an at least temporary air spring between the forward dampening element 6176 and the piston 243, wherein the friction and the air spring dampen motion of the plunger and damper body 6170.

It is noted that in accordance with an alternative embodiment of the present invention, there is no channel 6180 provided in forward dampening element 6176. According to this embodiment, air is trapped between the forward dampening element 6176 and the piston 243, since the forward dampening element 6176 is disposed in a sealing relationship with the inner surface 3162 of the syringe 242. It is a particular feature of this alternative embodiment of the present invention that upon forward displacement of the improved plunger and damper assembly 4160 under the force of spring 180, the pressure between the forward dampening element 6176 and the piston 243 builds up, thus causing advancement of piston 243 relative to syringe 242 without any mechanical contact between the contact surface 3186 of the forward dampening portion 6172 and the piston 243. It is noted that in accordance with an embodiment of the present invention, the injection of medicament contained within syringe 242 may begin before engagement of the improved plunger and damper assembly 6160 and the piston 243.

It is further noted that if channel 6180 is provided on the forward dampening element 6176, then air pressure from the space between the forward dampening portion 6172 and the piston 243 is released via channel 6180.

It is noted that the air release is dependent on the existence and size of channel 6180. In an alternative embodiment, the channel 6180 may be eliminated from the forward resilient dampening element 6176.

It is further noted that any one of forward dampening elements 3176 (shown in FIGS. 6A & 6B), 4176 (shown in FIGS. 11A-11C), 5176 (shown in FIGS. 12A-12C), or 6176 (shown in FIGS. 13A-13C), can be used in conjunction with rearward dampening element 3174 (shown in FIGS. 5A & 5B). Additionally, any one of forward dampening elements 3176, 4176 or 5176 can be mounted on the forward dampening portion 6172, which is illustrated and described in detail with reference to FIGS. 13A-13C.

Figure 14:
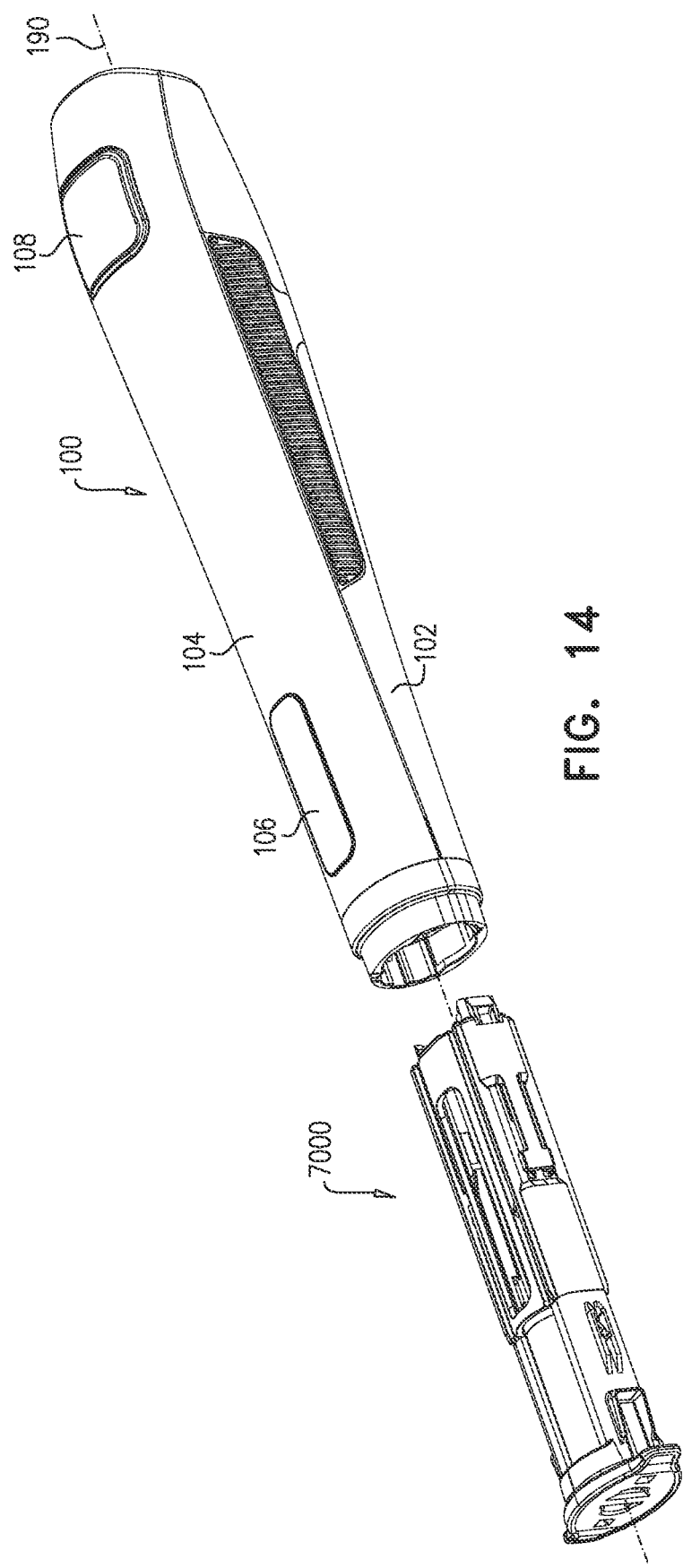
FIG. 14 is a simplified drawing illustrating the automatic injection device of FIGS. 1A & 1B and an improved medicament module just prior to operative engagement of the improved medicament module with the automatic injection device.

Reference is now made to FIG. 14, which is a simplified drawing illustrating the automatic injection device 100 of FIGS. 1A & 1B and an improved medicament module just prior to operative engagement of the improved medicament module with the automatic injection device 100.

It is seen in FIG. 14 that an improved medicament module 7000 can be inserted into operative engagement with the automatic injection device 100 of FIGS. 1A & 1B.

All components of the automatic injection device 100 are preferably identical to that shown in FIGS. 1A & 1B of PCT Patent application PCT/IL2016/050929 and described therein, the improved medicament module 7000 is similar to that shown in FIGS. 2A & 2B of PCT Patent application PCT/IL2016/050929, but is different therefrom in various aspects which are described in detail hereinbelow. The disclosure of PCT Patent application PCT/IL2016/050929 is hereby incorporated by reference.

Preferably, the automatic injection device 100 is reusable and the improved medicament module 7000 is disposable. Alternatively, both the automatic injection device 100 and the improved medicament module 7000 are disposable. Further alternatively, both the automatic injection device 100 and the improved medicament module 7000 are reusable. It is noted that both the automatic injection device 100 and the improved medicament module 7000 are mutually disposed along longitudinal axis 190.

Figure 15A:
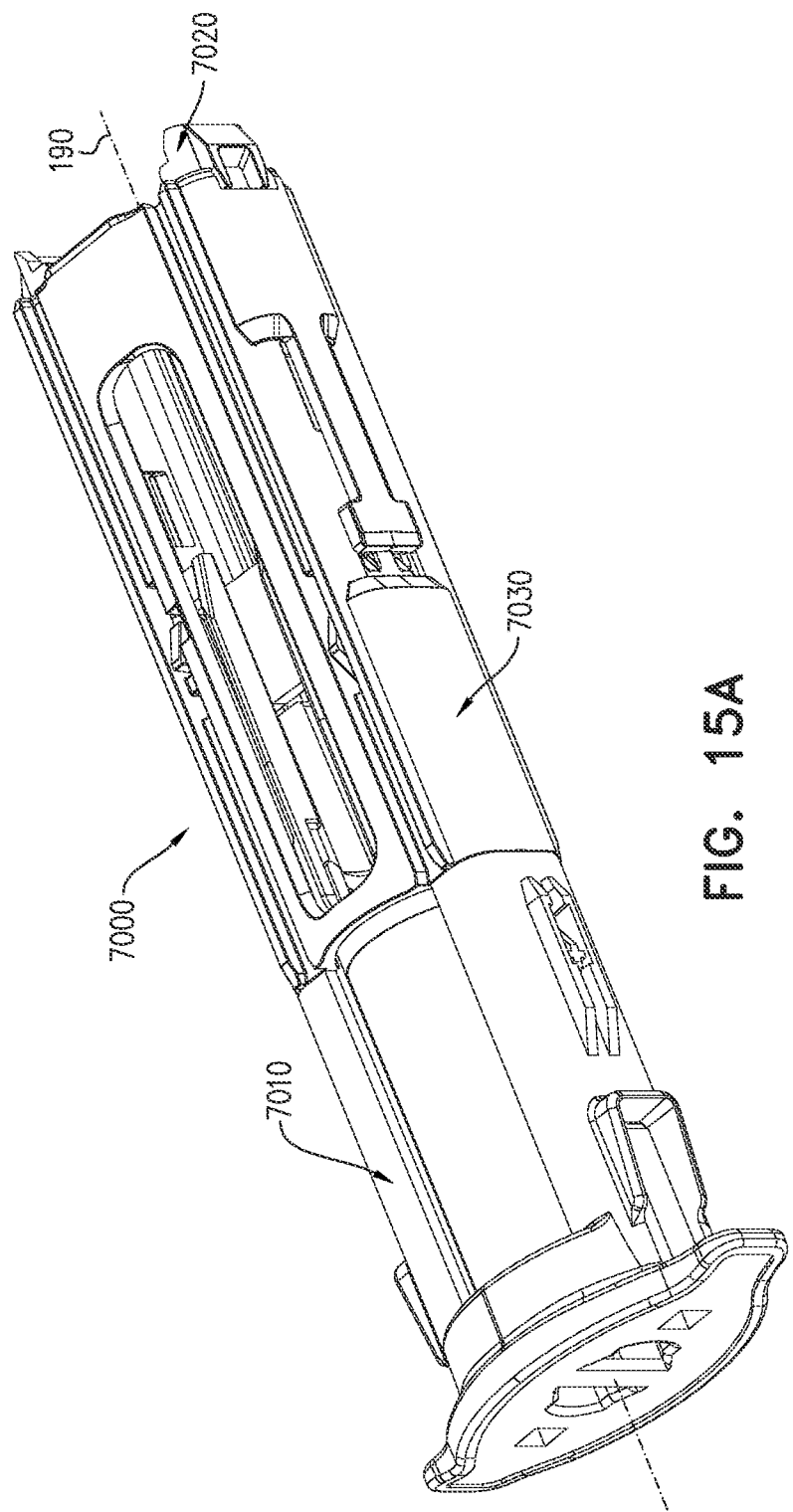
FIGS. 15A and 15B are respectively simplified assembled view and exploded view pictorial illustrations of the improved medicament module constructed and operative in accordance with an embodiment of the present invention and usable in conjunction with the reusable automatic injection device such as that illustrated in FIGS. 1A & 1B.
Figure 15B:
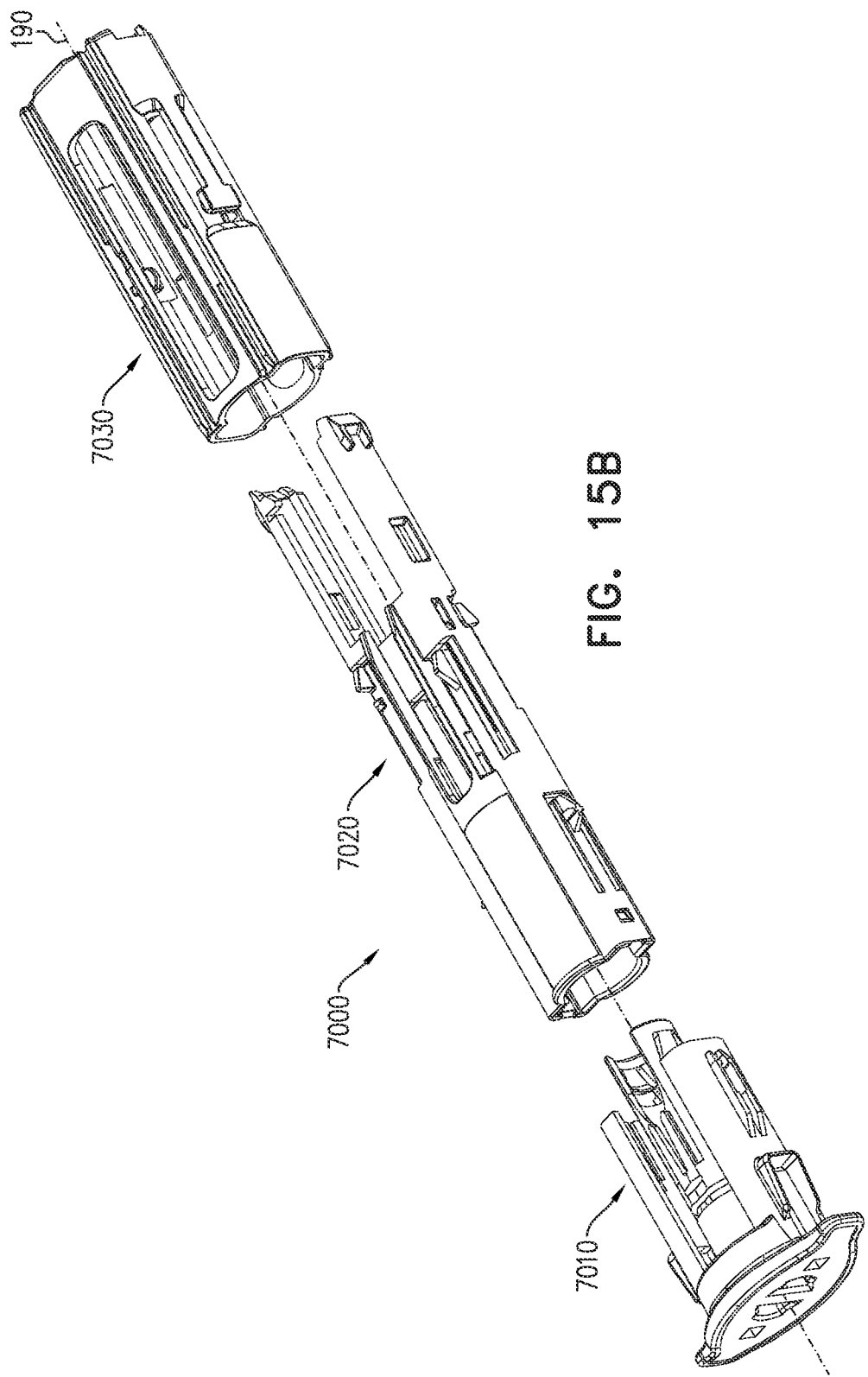

As seen in FIGS. 15A and 15B, the improved medicament module 7000 comprises a cover removal assembly, hereinafter referred as an RNS frigid needle shield) remover assembly 7010, a needle shield 7020, and a module housing 7030, which partially encloses the needle shield 7020, all mutually arranged along longitudinal axis 190. The improved medicament module 7000 is adapted to receive a syringe 242 having a piston 243 contained therein and removable needle cover 244 surrounding a needle 246, which extends forwardly of a syringe flange 248, such as described in detail with reference to FIGS. 1A & 1B.

As seen in FIGS. 15A and 15B, the improved medicament module 7000 comprises an RNS remover assembly 7010, a needle shield 7020, and a module housing 7030, which partially encloses the needle shield 7020, all mutually arranged along longitudinal axis 190. The improved medicament module 7000 is adapted to receive a syringe 242 having a piston 243 contained therein and removable needle cover 244 surrounding a needle 246, which extends forwardly of a syringe flange 248, such as described in detail with reference to FIGS. 1A & 1B.

It is appreciated that syringe 242 can be any type of a medicament container, such as pre-filled syringe, cartridge.

Figure 16A:
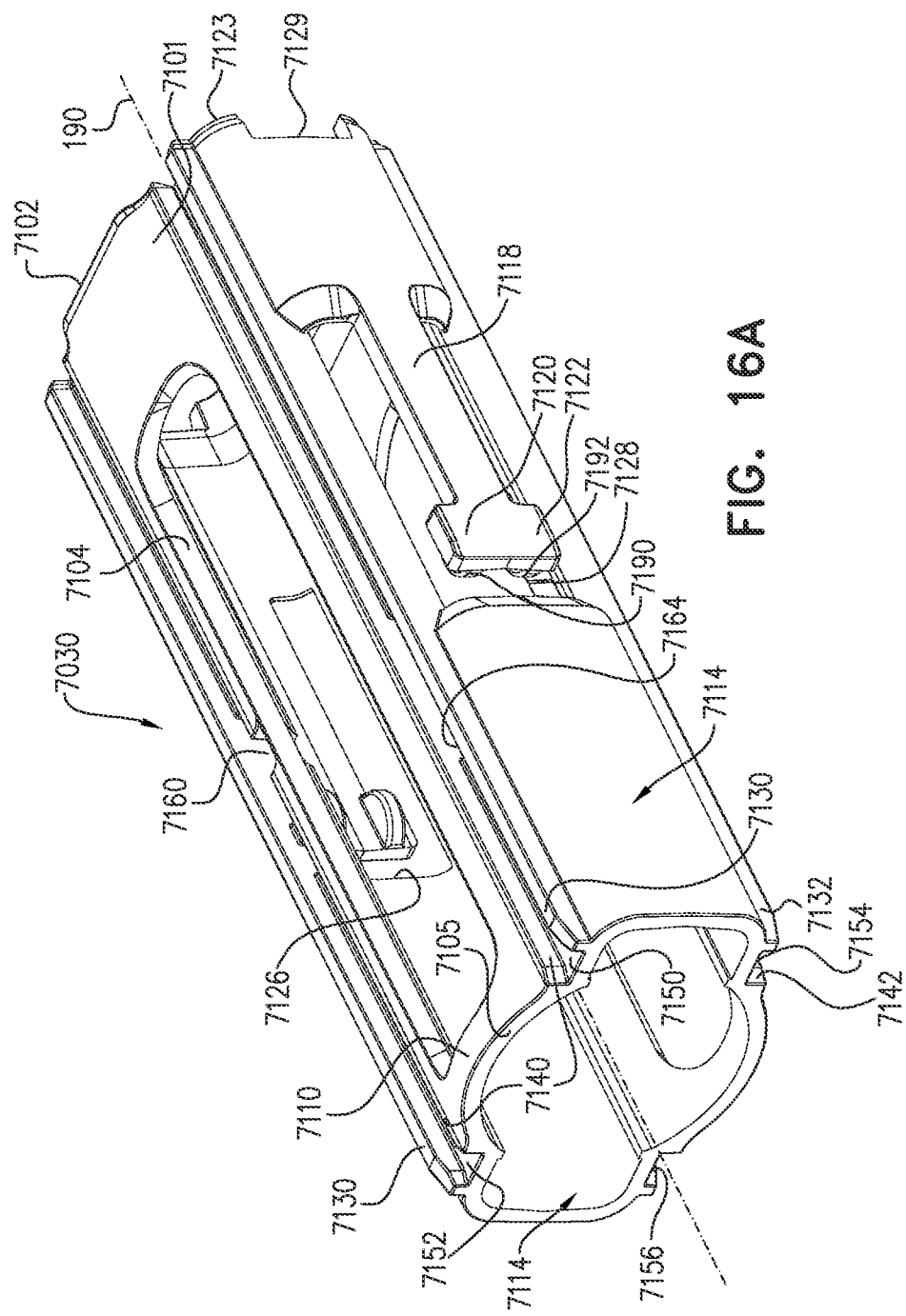
Figure 16B:
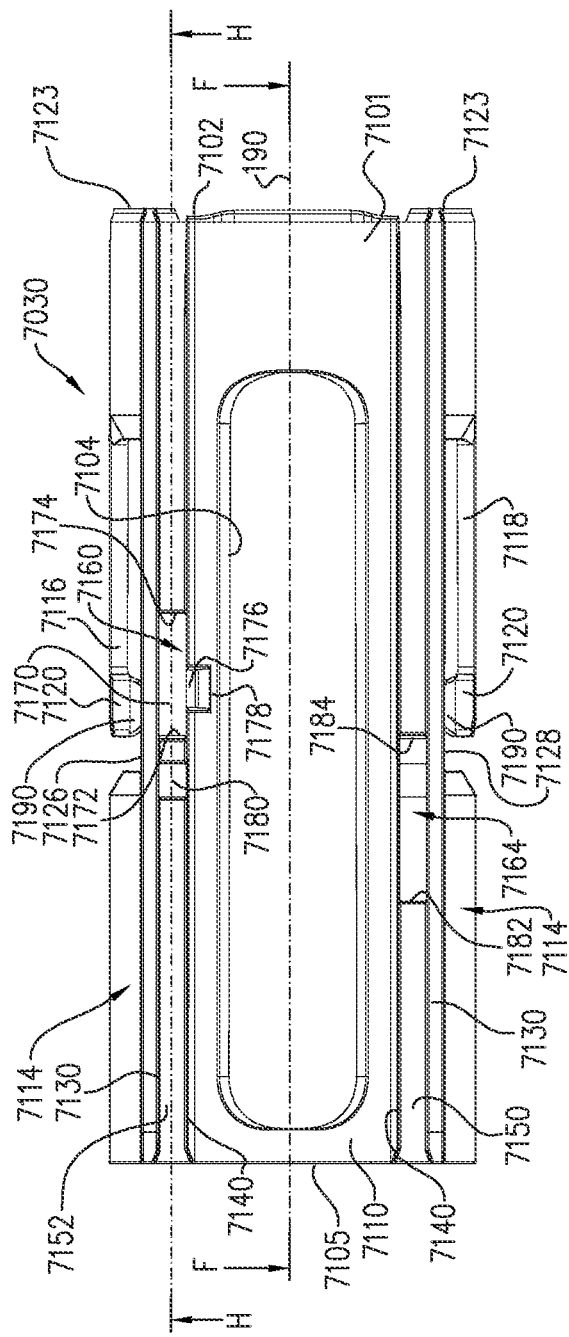
Figure 16C:
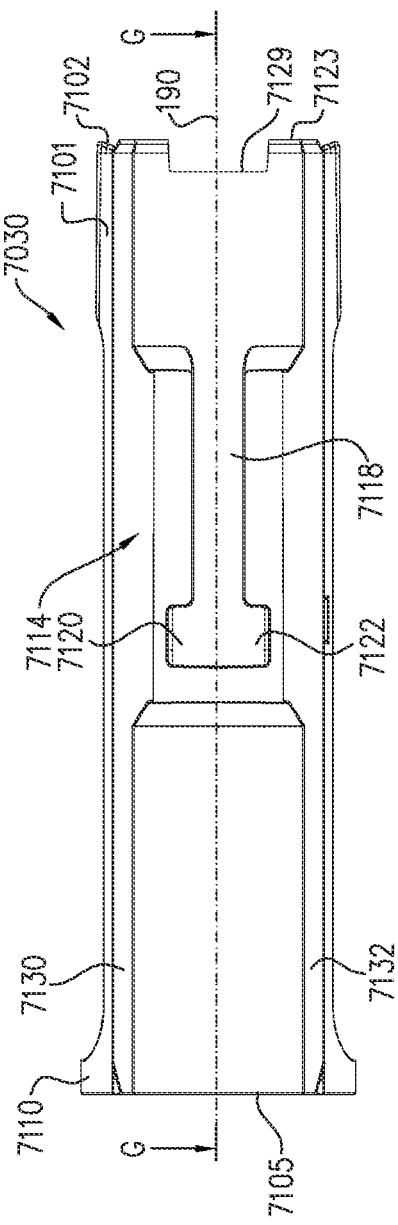
Figure 16E:
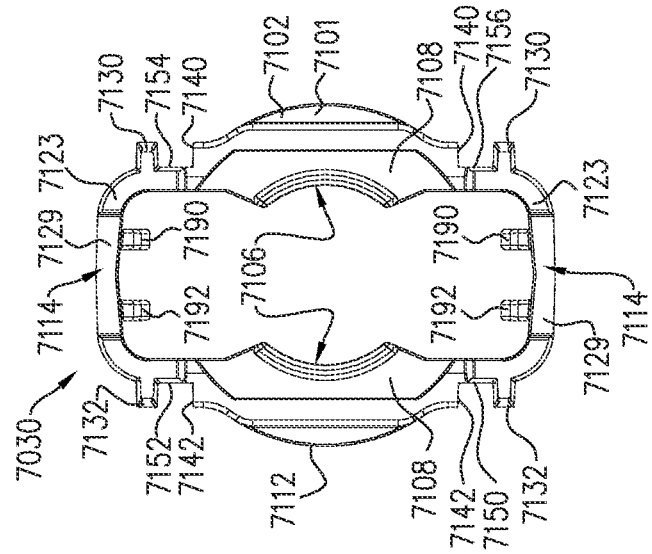
Figure 16D:
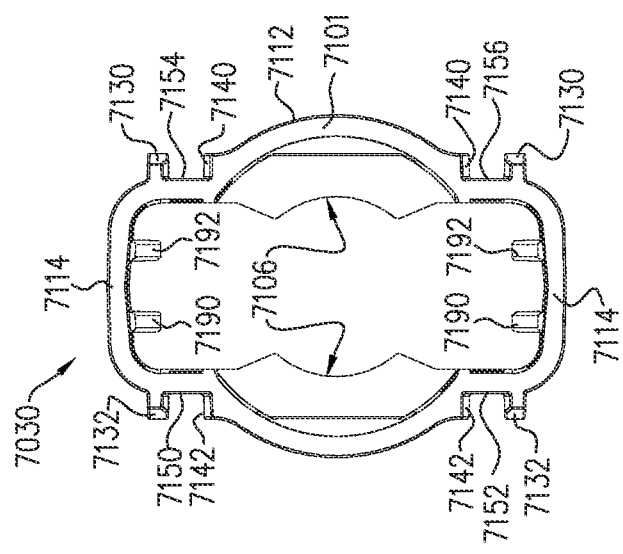
Figure 16H:
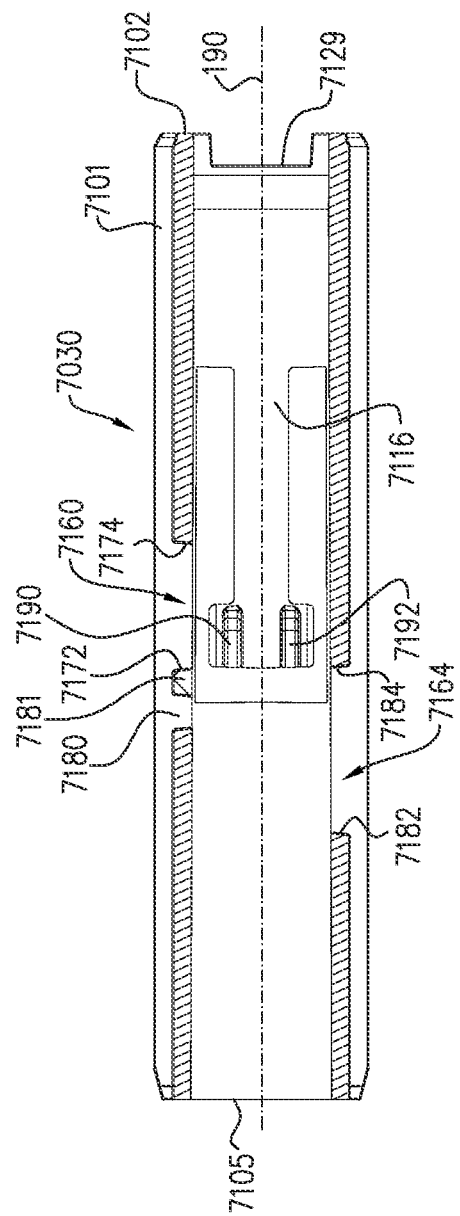

Reference is now made to FIGS. 16A, 16B, 16C, 16D, 16E, 16F, 16G and 16H, which are simplified respective perspective, top and bottom view, side view, first and second end view and three sectional illustrations taken along lines F-F in FIG. 16B, lines G-G in FIG. 16C and line H-H in FIG. 16B of the module housing 7030, forming part of the improved medicament module 7000 of FIGS. 15A & 15B.

As seen in FIGS. 16A-16H, the module housing 7030 preferably is an integrally formed element, preferably injection molded of plastic and preferably has a generally cylindrical configuration including a generally tubular portion 7101, which defines backward-facing generally symmetric edges 7102 having generally symmetric top/bottom facing windows 7104 and forward-facing generally symmetric edges 7105. Top-bottom facing windows 7104 may be obviated, if module housing 7030 is formed of a transparent material. Generally forwardly of edges 7102 are a pair of inwardly directed partially azimuthal bulkheads 7106, having rearwardly-facing surfaces 7108.

Module housing 7030 is preferably side-to-side symmetric about longitudinal axis 190. Module housing 7030 is preferably formed with a central, generally circular cylindrical portion 7112 and a pair of generally symmetric side-disposed longitudinal wall portions 7114 extending from backward-facing generally symmetric edges 7102 to forward-facing generally symmetric edges 7105.

Fingers 7116 and 7118 extend forwardly in respective cut outs 7126 and 7128 formed in longitudinal wall portions 7114 and parallel to longitudinal axis 190, each of fingers 7116 and 7118 preferably terminating in side-to-side facing protrusions 7120 and 7122.

Longitudinal wall portions 7114 preferably each terminate rearwardly at a rearward edge 7123, which defines a generally rectangular cut-out 7129.

A pair of mutually spaced longitudinal ribs 7130 and 7132 are formed on opposite sides of each of the wall portions 7114. Ribs 7130 and 7132 each define, together with an adjacent respective mutually facing rib 7140 and 7142 a longitudinal channel. The channels are respective designated by reference numerals 7150, 7152, 7154 and 7156.

First slots 7160 and 7162 are formed along channels 7152 and 7156 respectively and second slots 7164 and 7166 are defined along channels 7150 and 7154 respectively. First slots 7160 and 7162 are generally T-shaped, such that each includes a longitudinal portion 7170 having a forward facing edge 7172 and a rearward facing edge 7174 and a lateral portion 7176 generally transversely extending from the longitudinal portion 7170, The lateral portion 7176 has an inwardly facing edge 7178.

An aperture 7180 is formed slightly forwardly of and spaced from the forward facing edge 7172. A protrusion 7181 is formed between slot 7160 and aperture 7180.

Second slots 7164 and 7166 each include a forward facing edge 7182 and a rearward facing edge 7184.

A pair of inwardly directed side protrusions 7190 and 7192 extend inwardly from each of arms 7116 and 7118 in a plane perpendicular to axis 190 and each define a generally circular inwardly facing edge 7194.

Figure 17E:
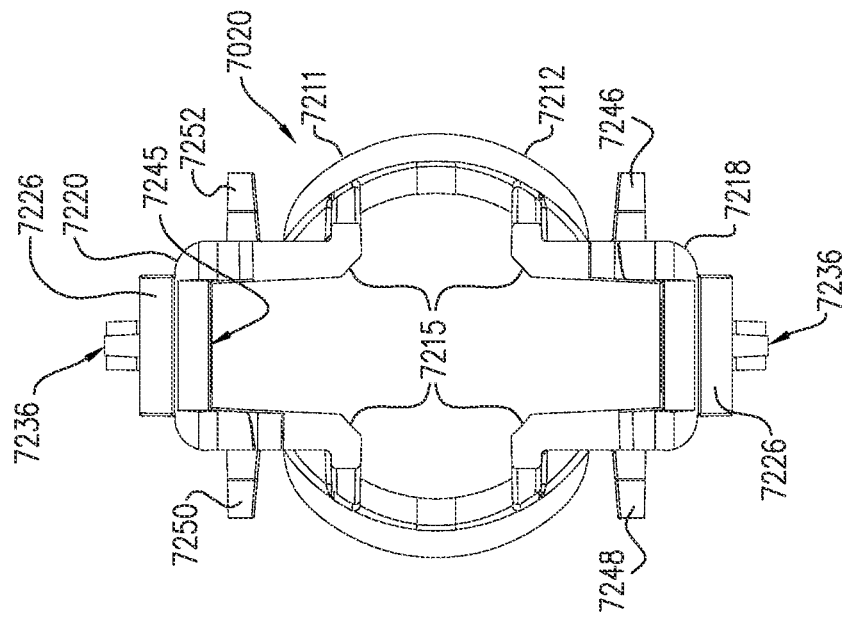
Figure 17D:
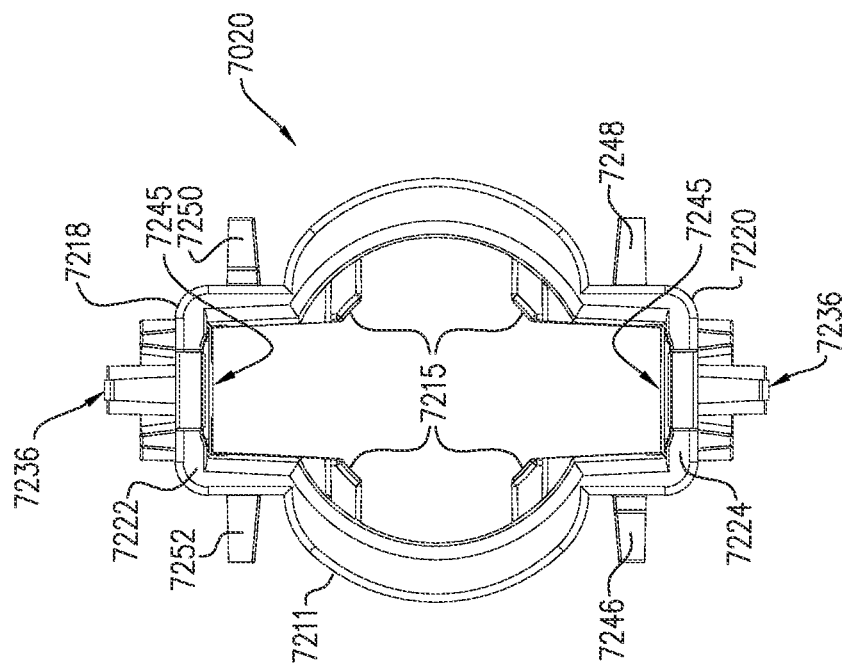

Reference is now made to FIGS. 17A, 17B, 17C, 17D, 17E, 17F, 17G and 17H, which are simplified respective perspective, top and bottom view, side view, first and second end view and three sectional illustrations taken along lines F-F in FIG. 17B, lines G-G in FIG. 17C and lines H-H in FIG. 17B of the needle shield 7020, forming part of the improved medicament module 7000 of FIGS. 15A & 15B.

As seen in FIGS. 17A-17H, needle shield 7020 preferably is an integrally formed element, preferably injection molded of plastic and preferably has a generally cylindrical configuration arranged about a longitudinal axis 190.

Needle shield 7020 preferably includes a generally conical tubular portion 7211 terminating at a partially circumferential rim 7212 extending radially outwardly therefrom and defining a generally circular cylindrical hollow bore. Generally conical tubular portion 7211 preferably defines a plurality of generally longitudinal guide surfaces 7215 which serve to guide the axial travel of a syringe therein. Needle shield 7020 preferably includes a pair of side mounting arms 7218 and 7220, extending rearwardly from tubular portion 7211 and having respective rearward facing edges 7222 and 7224.

Adjacent each of rearward facing edges 7222 and 7224 there is preferably formed an inwardly directed toothed syringe retaining protrusion 7225.

Each of mounting arms 7218 and 7220 is formed with a generally U-shaped outer facing protrusion 7226 adjacent respective edges 7222 and 7224. Each of mounting arms 7218 and 7220 is formed with a rearward-facing flexible finger 7228, a forward recess 7229 located between the flexible finger 7228 and the circumferential rim 7212 and a rearward slot 7230 as well as a pair of narrow slots 7231 and 7232, forwardly of which are formed tapered surfaces 7233 and 7234 respectively. The forward recess 7229 has a forward tapered surface 7235.

Rearward-facing flexible finger 7228 preferably is formed with an outwardly-facing protrusion 7236 having a forwardly-facing tapered surface 7238 and a rearwardly-facing tapered surface 7240 joined at an outermost flat surface 7242.

Each of mounting arms 7218 and 7220 is preferably formed with an axial inwardly-facing surface 7243, which together with side ribs 7244 defines a channel 7245.

Mounting arm 7218 is formed with respective forward and rearward resilient finger portions 7246 and 7248. Mounting arm 7220 is formed with respective forward and rearward resilient finger portions 7250 and 7252. Finger portions 7248 and 7252 each include an outwardly-facing protrusion 7260 having a forward-facing surface 7262, a rearward-facing tapered surface 7264 and a rearward facing edge 7266. A protrusion 7268 is slightly forwardly spaced from protrusion 7260.

Finger portions 7246 and 7250 each include an outwardly-facing protrusion 7280 having a forward-facing tapered surface 7282, a rearward-facing tapered surface 7284 and a rearward facing edge 7286.

A forwardly tapered surface 7290 connects each of the respective edges 7222 and 7224 with the respective one of protrusions 7225.

A generally U-shaped aperture 7292 is formed between finger portion 7246 and 7252. A similar U-shaped aperture 7292 is formed between finger portion 7248 and 7250. It is seen in FIGS. 17A-17G that side mounting arms 7218 and 7220 preferably respectively extend from rearward extending edges 7222 and 7224 to circumferential rim 7212. A rearwardly extending recess 7294 is formed at the forward ends of side mounting arms 7218 and 7220, located adjacent the circumferential rim 7212.

Figure 19B:
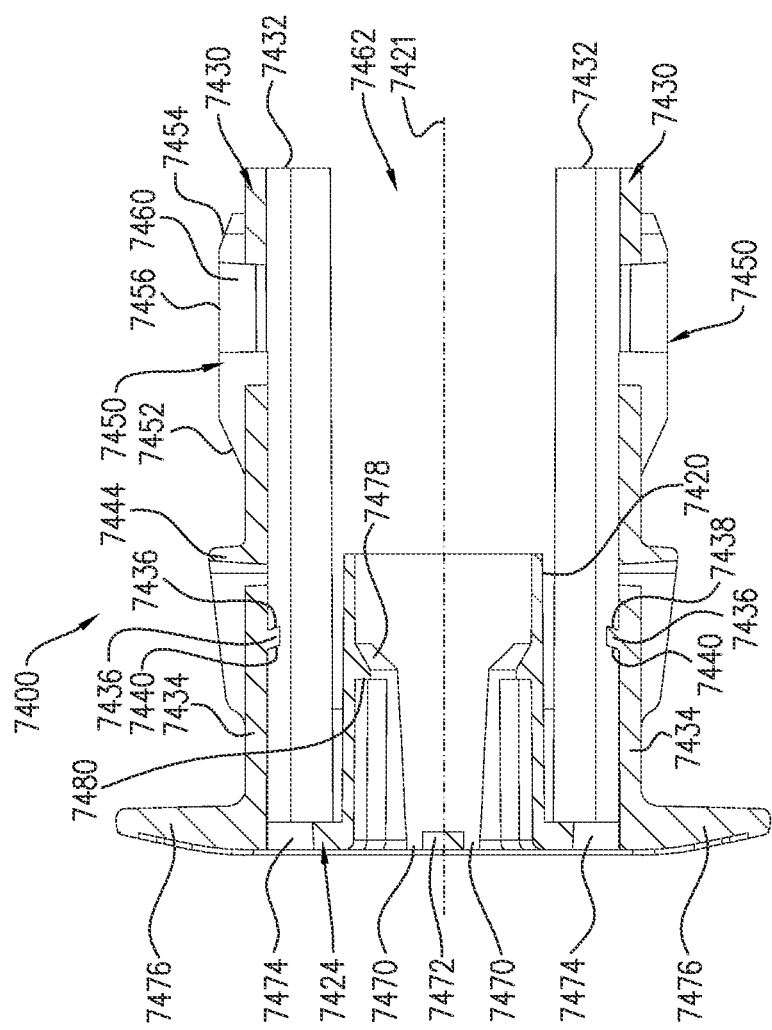
Figure 20A:
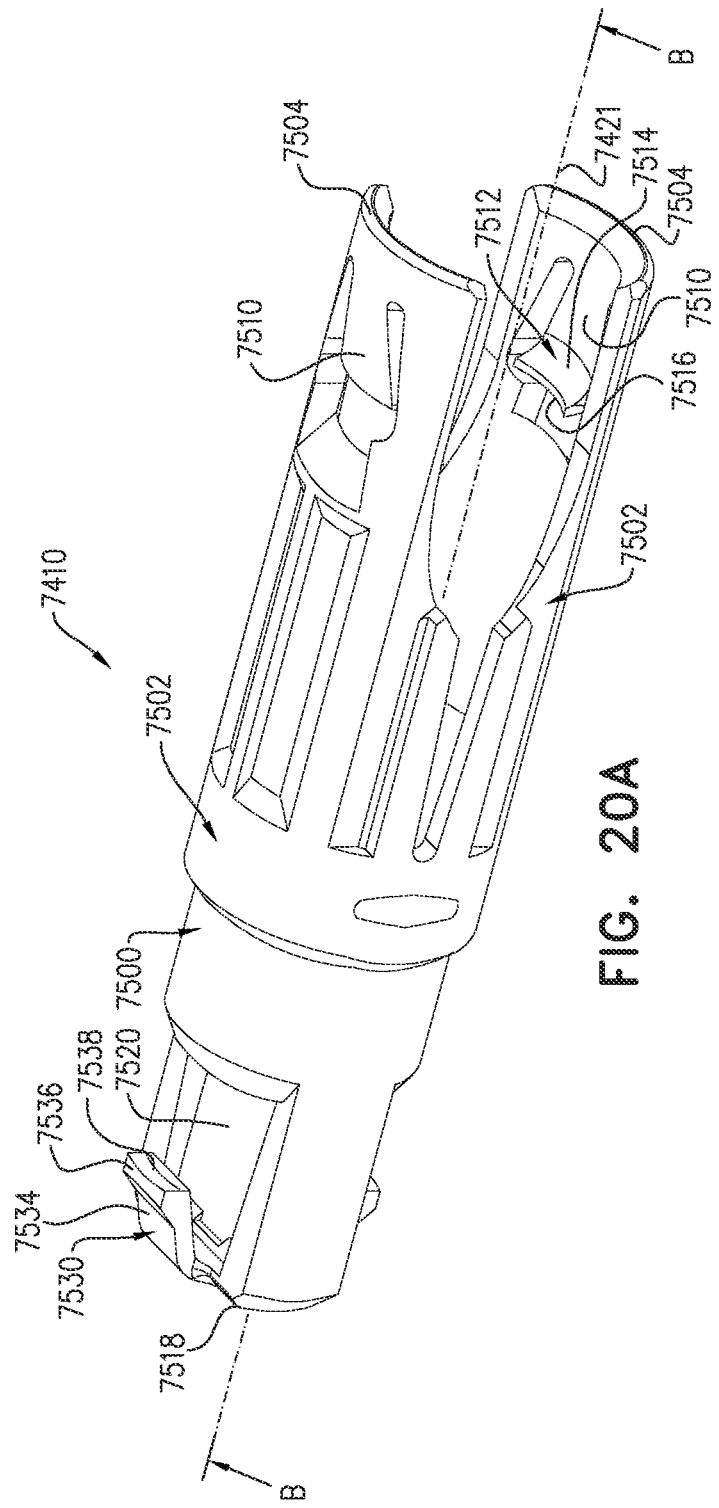
Figures 21A, 21B:
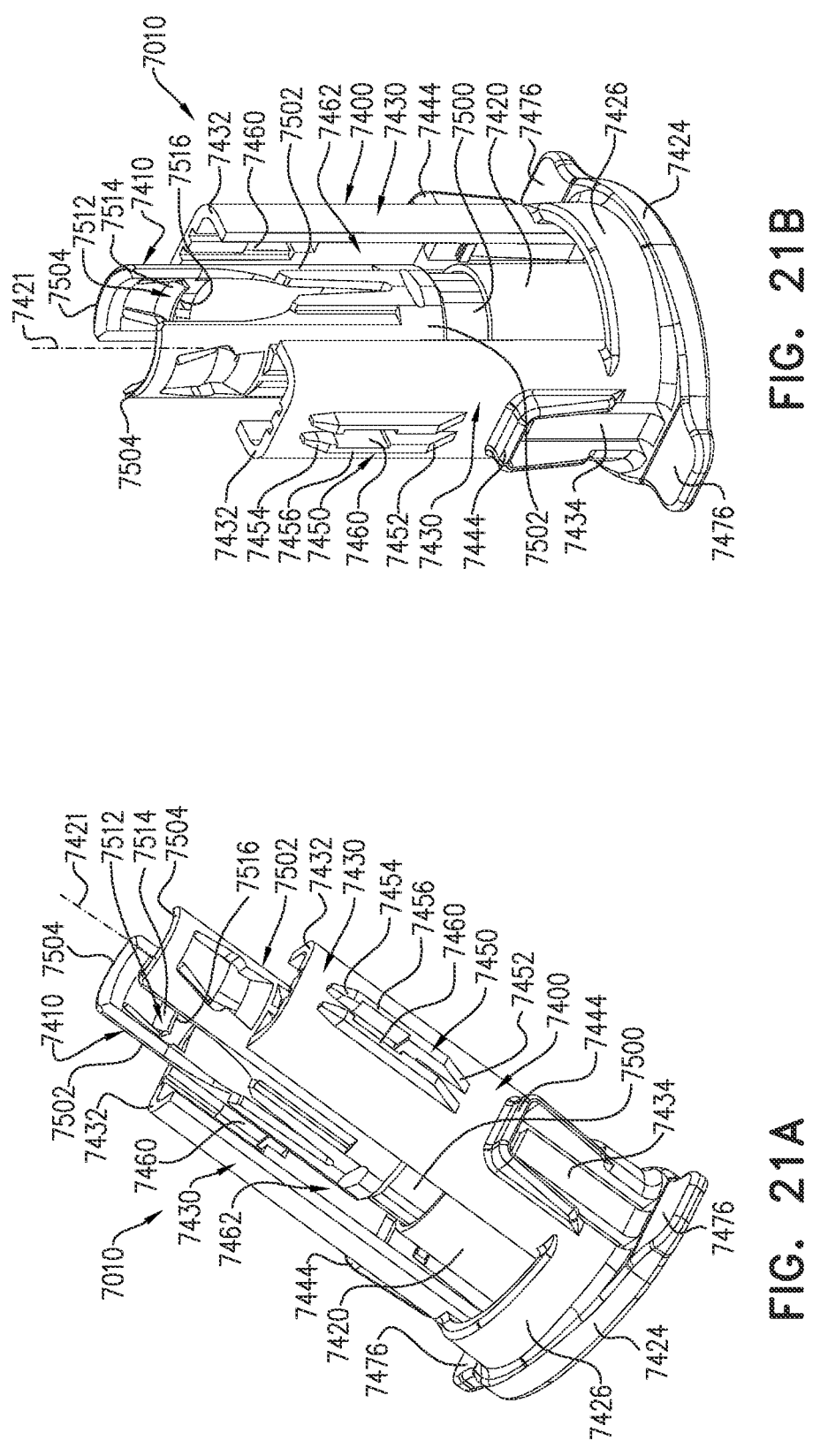

Reference is now made to FIGS. 18A and 18B, which are respectively simplified assembled view and exploded view pictorial illustrations of the RNS remover assembly 7010, forming part of the improved medicament module 7000 of FIGS. 15A & 15B and to FIGS. 19A & 19B, which are simplified respective pictorial and sectional illustrations of an outer portion of the RNS remover assembly 7010 of FIGS. 18A & 18B, section being taken along lines B-B in FIG. 19A and to FIGS. 20A & 20B, which are simplified respective pictorial and sectional illustrations of an inner portion of the RNS remover assembly 7010 of FIGS. 18A & 18B, section being taken along lines B-B in FIG. 20A. Reference is additionally made to FIGS. 21A, 21B, 21C, and 21D, which are simplified respective first and second perspective views, end view and a sectional view taken along lines D-D in FIG. 21C of the assembled RNS remover assembly, forming part of the improved medicament module 7000 of FIGS. 15A & 15B.

As seen in FIGS. 18A-21D, the RNS remover assembly 7010 is preferably comprised of an outer portion 7400 and an inner portion 7410, both of which are integrally formed elements preferably injection molded of plastic.

The outer portion 7400, seen specifically in FIGS. 19A & 19B, includes a generally tubular portion 7420 arranged along a longitudinal axis 7421 extending rearwardly from a base wall 7424. A generally forwardly extending circumferential protrusion 7426 has a generally oval cross-section and extends forwardly from base wall 7424 and along a certain longitudinal extent of the tubular portion 7420.

The outer portion 7400 has a pair of rearwardly extending arms 7430, each of which to extends rearwardly of the generally tubular portion 7420 to a rearwardmost edge surface 7432. Arms 7430 are each formed with resilient fingers 7434 disposed generally adjacent the base wall 7424. An inwardly extending protrusion 7436 is formed on the inside of each of the resilient fingers 7434, the protrusion has a rearwardly-facing angled edge 7438 and a forwardly-facing angled edge 7440. Radially outwardly extending generally U-shaped protrusions 7444 are formed partially around the outside perimeter of each of the resilient fingers 7434.

A pair of radially outwardly extending protrusions 7450 extend outwardly from each of arms 7430 and located between the U-shaped protrusions 7444 and the rearwardmost end 7432 of arms 7430. The protrusions 7450 include a forwardly tapered surface 7452, a rearwardly tapered surface 7454 and a flat surface 7456 connecting therebetween. An opening 7460 is formed through the pair of protrusions 7450 and extends into an inner volume 7462 that is formed by an imaginary circumference formed by the arms 7430.

There are two openings 7470 formed through the base wall 7424. The openings 7470 are generally spaced from each other, forming a bridge 7472 therebetween. Another two openings 7474, each formed on one side of each of openings 7470.

Two ear portions 7476 that are generally diametrically opposed to each other are formed on two opposite sides of the base wall 7424.

The tubular portion 7420 has a generally annular radially inwardly extending protrusion 7478 including a forwardly facing circular edge 7480, which is rearwardly spaced from the base wall 7424.

The inner portion 7410, seen specifically in FIGS. 20A & 20B, includes a generally tubular cylindrical portion 7500 and two arms 7502 which are mutually diametrically opposed to each other and extend rearwardly from the cylindrical portion 7500 to a rearward edge 7504. The imaginary diameter formed by the two arms 7502 is generally greater than the diameter of the cylindrical portion 7500.

A resilient finger 7510 is formed on each arm 7502 and extend forwardly from a location adjacent the rearward edge 7504. Each of the resilient fingers 7510 has a radially inwardly extending protrusion 7512, having a rearward tapered surface 7514 and a forwardly facing surface 7516.

The cylindrical portion 7500 has a forward end wall 7518. A circumferential opening 7520 is formed through the cylindrical portion 7500 and revolves about the longitudinal axis 7421. An anchor-shaped resilient protrusion 7530 extends rearwardly from the forward end wall 7518. The anchor-shaped resilient protrusion 7530 has a central portion 7532 and two mutually opposed side extensions 7534, each having a radially outwardly extending protrusion 7536 that to has a rearwardly facing surface 7538.

It is particularly seen in FIG. 21D that the inner portion 7410 is partially inserted into the inner volume 7462 of the outer portion 7400, specifically the cylindrical portion 7500 of the inner portion 7410 is inserted into the tubular portion 7420 of the outer portion 7400.

It is a particular feature of an embodiment of the present invention that the anchor-shaped resilient protrusion 7530 of the inner portion 7410 is snapped behind protrusion 7478 of the tubular portion 7420 of the outer portion 7400, such that rearwardly facing surface 7538 of resilient protrusion 7530 is snapped behind forwardly facing circular edge 7480 of protrusion 7478. The inner portion 7410 is freely slidable with respect to the outer portion 7400 along longitudinal axis 7421 between two operative positions. First operative position is when forward end wall 7518 of the inner portion engages the base wall 7424 of the outer portion 7400. Second operative position is when rearwardly facing surface 7538 of resilient protrusion 7530 is snapped behind forwardly facing circular edge 7480 of protrusion 7478.

Figure 22C:
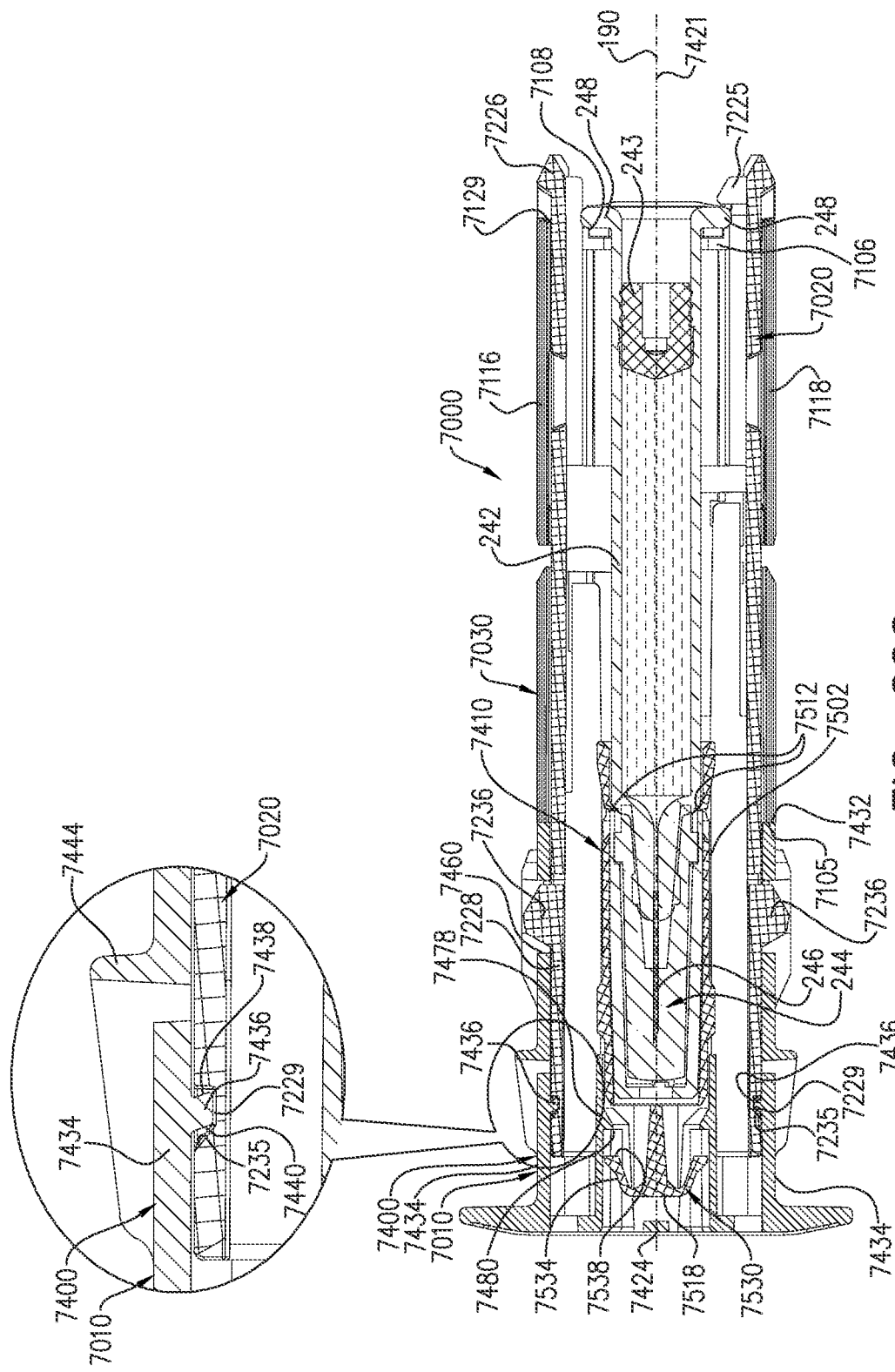
FIGS. 22C and 22D are two orthogonal section views taken along lines C-C in FIG. 22A and lines D-D in FIG. 22B of the assembled improved medicament module in the operative orientation shown in FIGS. 22A & 22B.
Figure 22D:
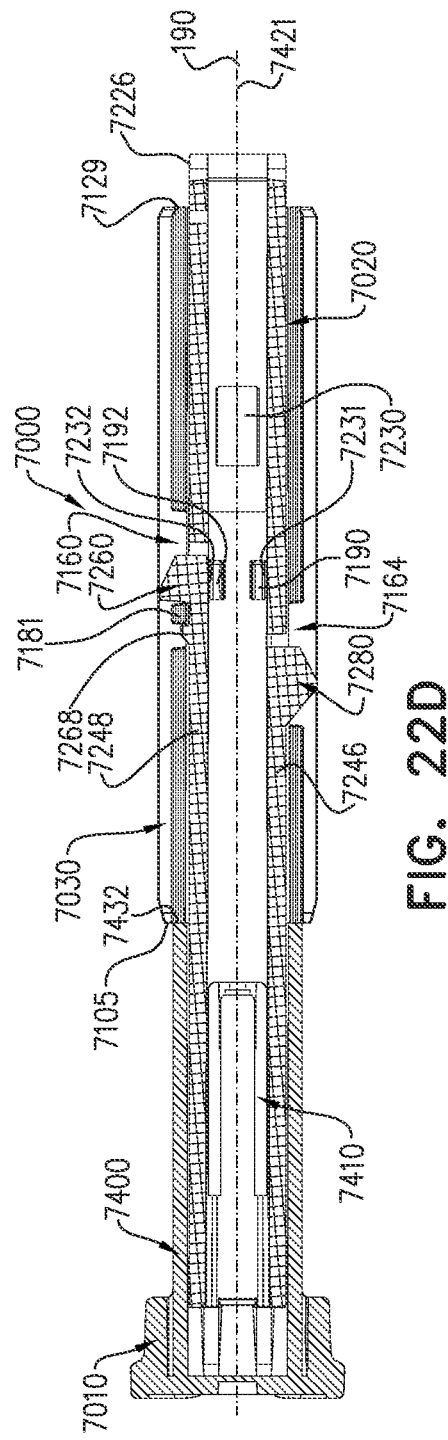

Reference is now made to FIGS. 22A and 22B, which are two different simplified plan views of the assembled improved medicament module 7000 of FIGS. 15A & 15B in a storage operative orientation, showing the RNS remover assembly 7010 of FIGS. 18A & 18B attached to the needle shield 7020 of FIGS. 17A-17H. Reference is additionally made to FIGS. 22C and 22D, which are two orthogonal section views taken along lines C-C in FIG. 22A and lines D-D in FIG. 22B of the assembled improved medicament module 7000 in the operative orientation shown in FIGS. 22A & 22B.

FIGS. 22A-22D particularly illustrate the structural relationship of needle shield 7020 (FIGS. 17A-17H), module housing 7030 (FIGS. 16A-16H) and RNS remover assembly 7010 (FIGS. 21A-21D).

As seen particularly in FIGS. 22A-22D, needle shield 7020 is located generally inside and coaxial with module housing 7030, arranged along mutual longitudinal axis 190.

It is also seen that in a "storage" operative orientation, when the RNS remover assembly 7010 is attached to the needle shield 7020, that the needle shield 7020, is fixedly retained in the module housing 7030 against axial relative movement therebetween. Needle shield 7020 is retained against forward axial displacement relative to module housing 7030 along axis 190 by engagement of protrusions 7226 at the rearward end of the needle shield 7020 in cutouts 7129 at the edge 7123 of the module housing 7030.

It is additionally seen that syringe 242 is fixedly retained against rearward axial motion along axis 190 relative to needle shield 7020 and module housing 7030 by engagement of protrusion 7225 of needle shield 7020 with flange 248 of syringe 242.

It is further noted that syringe 242 is fixedly retained against forward axial motion along axis 190 relative to needle shield 7020 and module housing 7030 by engagement of flange 248 of syringe 242 with rearwardly-facing surfaces 7108 of bulkheads 7106 of module housing 7030.

It is seen in FIGS. 22A-22D that needle shield 7020 is retained against forward or rearward axial displacement relative to module housing 7030 along longitudinal axis 190 by engagement of protrusions 7260 of finger protrusions 7248 and 7252 of needle shield 7020 in slots 7160 of the module housing 7030 and protrusions 7260 are safely held within slots 7160 due to engagement of protrusion 7181 of the module housing 7030 in between protrusion 7260 and protrusion 7268 of the needle shield 7020. Additionally, needle shield 7020 is retained against rearward or forward axial displacement relative to module housing 7030 along axis 190 by engagement of protrusions 7280 of finger portions 7246 and 7250 of needle shield 7020 in slots 7164 of the module housing 7030.

Additionally, it is seen that protrusions 7190 and 7192 of arms 7116 and 7118 respectively of module housing 7030 are seated in narrow slots 7231 and 7232 of the needle shield 7020.

It is a particular feature of an embodiment of the present invention that in this storage operative orientation, inwardly directed side protrusions 7190 and 7192 of each of fingers 7116 and 7118 of the module housing 7030 are inserted into respective narrow slots 7231 and 7232 of the needle shield 7020. As seen in FIGS. 22A-22D, the rearwardmost edge surface 7432 of the outer portion 7400 of the RNS remover assembly 7010 abuts the forward-facing generally symmetric edges 7105 of the module housing 7030, thus contributing to the fact that the inwardly directed side protrusions 7190 and 7192 cannot disengage from narrow slots 7231 and 7232 of needle shield 7020 upon application of force on the improved medicament module 7000 in either direction.

It is also seen that RNS remover assembly 7010 is located generally forwardly of the module housing 7030 and both inside and outside of needle shield 7020 and coaxially therewith such that, respective axes 190 and 7421 are coaxial. More specifically, two arm portions 7502 of the inner portion 7410 of RNS remover assembly 7010 is located in the generally circular cylindrical hollow bore of needle shield 7020. Arm portions 7502 of the inner portion 7410 of RNS remover assembly 7010 generally surrounds and attachably engages removable needle cover 244 by virtue of the engagement of inwardly directed protrusions 7512 of the inner portion 7410 of RNS remover assembly 7010 with a rearward edge of removable needle cover 244.

As mentioned above with respect to FIGS. 21A-21D, anchor-shaped resilient protrusion 7530 of the inner portion 7410 is snapped behind protrusion 7478 of the outer portion 7400, such that rearwardly facing surface 7538 of resilient protrusion 7530 is snapped behind forwardly facing circular edge 7480 of protrusion 7478. The inner portion 7410 is freely slidable with respect to the outer portion 7400 along longitudinal axis 7421 between two positions. First position is when forward end wall 7518 of the inner portion engages the base wall 7424 of the outer portion 7400. Second position is when rearwardly facing surface 7538 of resilient protrusion 7530 is snapped behind forwardly facing circular edge 7480 of protrusion 7478. Slidable displacement of the anchor-shaped resilient protrusion 7530 ensures positive engagement of the protrusions 7512 of the inner portion 7410 of RNS remover assembly 7010 and thus in turn ensures the removal of the removable needle cover 244 upon detachment of the RNS remover assembly 7010 from the improved medicament module 7000, as described in detail hereinbelow.

It is a particular feature of an embodiment of the present invention, as seen specifically in FIG. 22C, that protrusions 7436 of the resilient fingers 7434 of the outer portion 7400 of the RNS remover assembly 7010 are inserted and held within forward recesses 7229 of the needle shield 7020, by means of engagement of forwardly facing angled edges 7440 of the outer portion 7400 of the RNS remover assembly 7010 with the forward tapered surfaces 7235 of recesses 7229 of the needle shield 7020.

It is further seen that protrusions 7236 of rearward-facing flexible fingers 7228 of needle shield 7020 are seated in corresponding openings 7460 of the outer portion 7400 of the RNS remover assembly 7010, thereby locking the needle shield 7020 to the RNS remover assembly 7020.

Figure 23B:
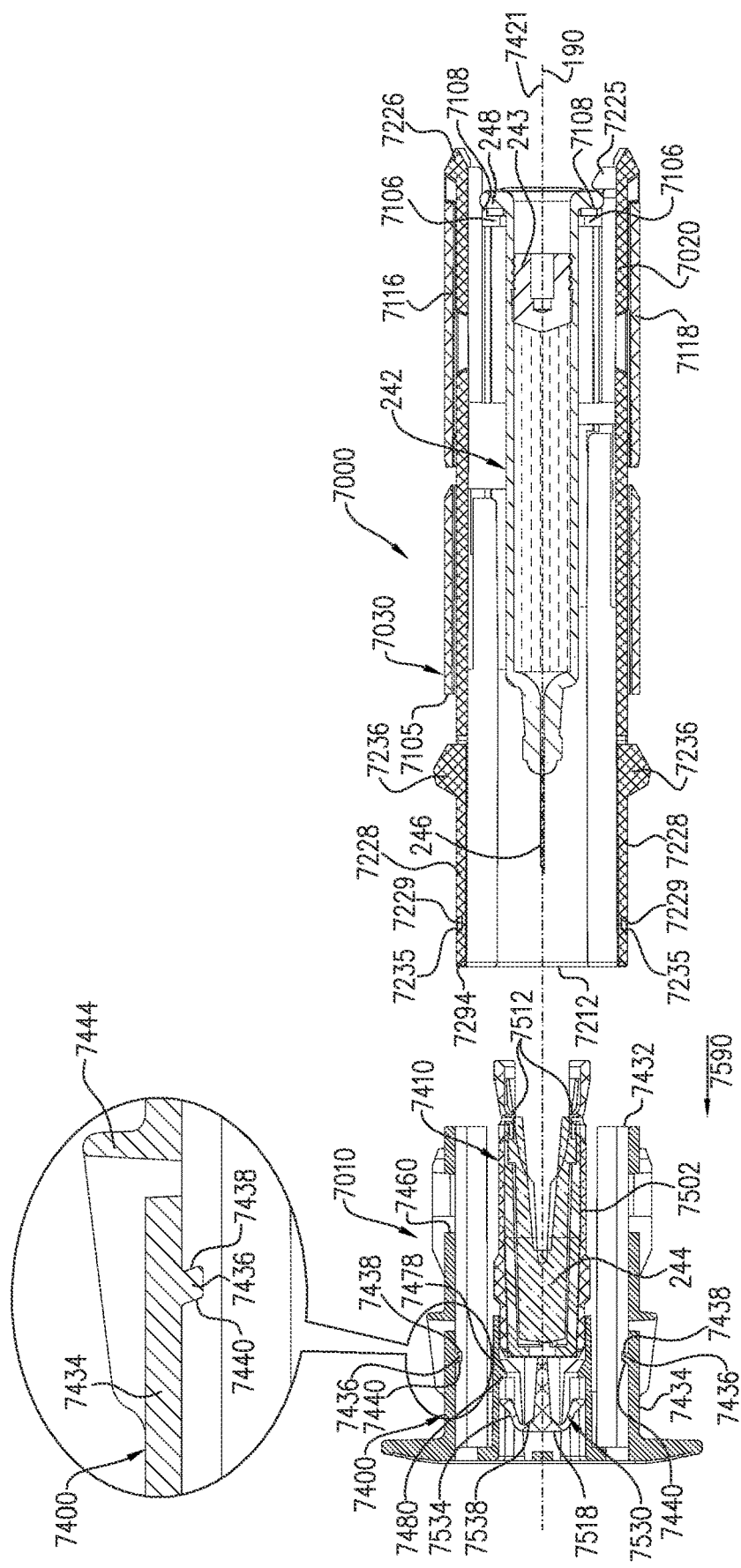

Reference is now made to FIGS. 23A and 23B, which are respectively simplified pictorial and section view illustrations of the improved medicament module of FIGS. 15A & 15B, showing the RNS remover assembly 7010 of FIGS. 18A & 18B detached from the needle shield 7020 of FIGS. 17A-17H, section being taken along lines B-B in FIG. 23A.

As seen in FIGS. 23A and 23B, when the RNS remover assembly 7010 (FIGS. 21A—21D) is detached from the needle shield 7020 of the improved medicament module 7000, as by axial forward pulling of the RNS remover assembly 7010 along axis 190, which is enabled by disengagement of outwardly-facing protrusions 7236 of needle shield 7020 from openings 7460 of RNS remover assembly 7010. It is a particular feature of an embodiment of the present invention that this disengagement is only possible when the improved medicament module 7000 and the reusable automatic injection assembly 100 are in an axial operative orientation corresponding to that shown in FIGS. 45A-45D of PCT Patent application PCT/IL2016/050929, which is incorporated by reference herein, such that ribs 1315 (FIGS. 21A-21G of PCT Patent application PCT/IL2016/050929), engage protrusions 7236 (FIGS. 22A-22D).

The removable needle cover 244 is retained interiorly of the inner portion 7410 of the to RNS remover assembly 7010, preferably by engagement of inwardly directed protrusions 7512 of arms 7502 of the inner portion 7410 of the RNS remover assembly 7010 with a rearward-facing edge or adjacent to this edge of the removable needle cover 244.

It is a particular feature of an embodiment of the present invention that notwithstanding the exact location of the protrusion 7512 of the inner portion 740 of the RNS remover assembly 7010 relative to the rearward edge of the removable needle cover 244, the removable needle cover 244 is removed in all instances due to the slidable displacement of the inner portion 7410 relative the outer portion 7400 of the RNS remover assembly 7010. This relative displacement between the two portions of the RNS remover assembly 7010 compensates for any manufacturing tolerances that may cause dimensional incompatibility between the removable needle cover 244 and the RNS remover assembly 7010.

It is a particular feature of an embodiment of the present invention, as seen specifically in FIG. 23C, that upon application of force on the RNS remover assembly 7010 in a direction indicated by arrow 7590, protrusions 7436 of the resilient fingers 7434 of the outer portion 7400 of the RNS remover assembly 7010 are disengaged from forward recesses 7229 of the needle shield 7020, by means of rearward slidable displacement of forwardly facing angled edges 7440 of the outer portion 7400 of the RNS remover assembly 7010 rearwardly over the forward tapered surfaces 7235 of recesses 7229 of the needle shield 7020. It is noted that rearward displacement of protrusions 7436 of the resilient fingers 7434 of the outer portion 7400 of the RNS remover assembly 7010 relative to forward tapered surfaces 7235 of recesses 7229 of the needle shield 7020 is facilitated by the fact that both forwardly facing angled edges 7440 and forward tapered surfaces 7235 are angled in the same direction.

Figure 24B:
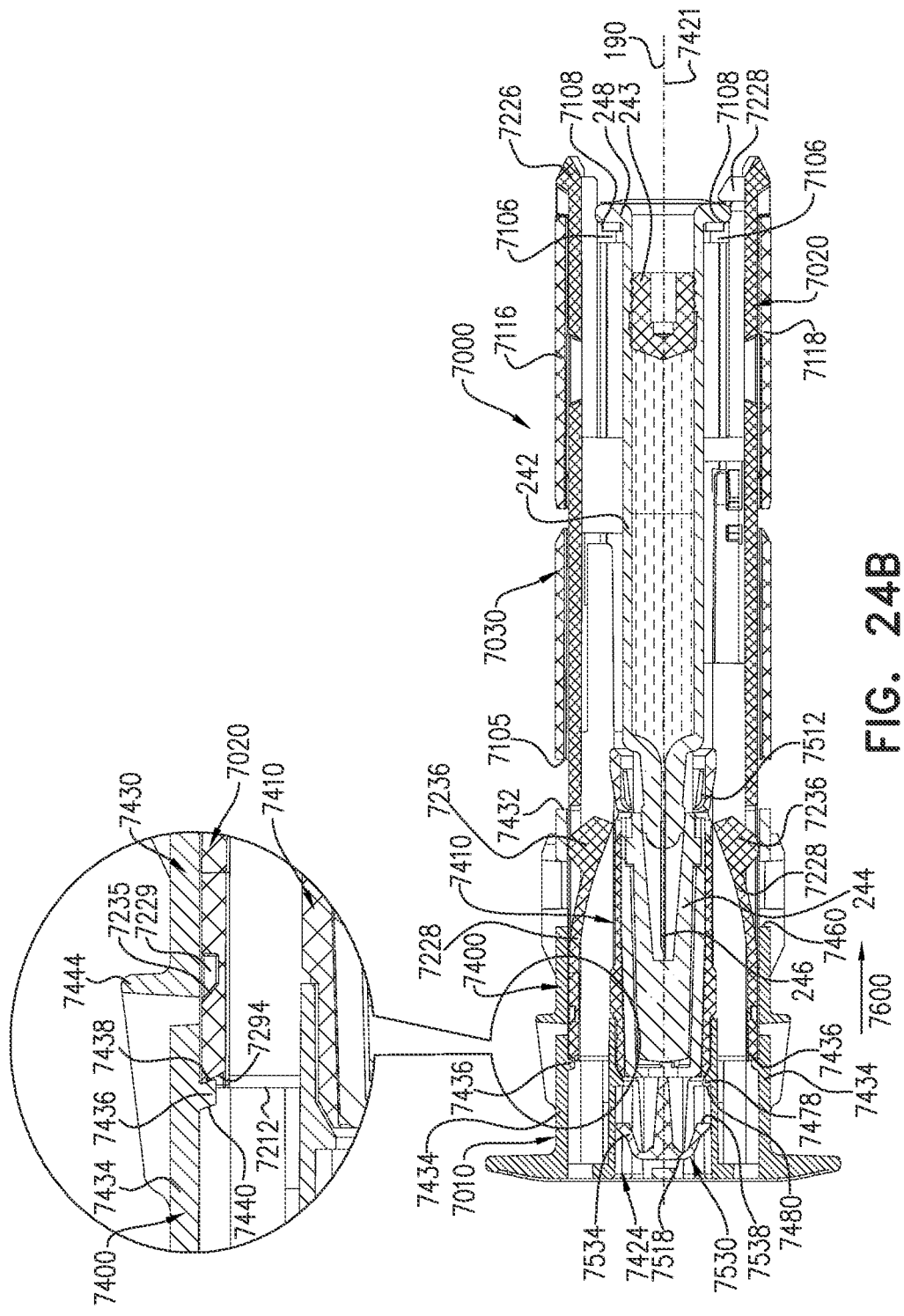

Reference is now made to FIGS. 24A and 24B, which are respectively simplified pictorial and section view illustrations of the improved medicament module 7000 of FIGS. 15A & 15B, shown in a mis-use orientation of the improved medicament module 7000 associated with the automatic injection device 100 of FIGS. 1A & 1B, when the user attempts to re-attach the RNS remover assembly 7010 back onto the needle shield 7020 of FIGS. 17A-17H of the improved medicament module 7000, section being taken along lines B-B in FIG. 24A.

An undesirable orientation is seen in FIGS. 24A and 24B, in which the user attempts to insert the RNS remover assembly 7010 back into the improved medicament module 7000 after it was already removed from it. It is appreciated that in this mis-use orientation, the user may attempt to charge a used medicament module 7000 into the reusable automatic injection assembly 100 and it is desirable to prevent such charging, thus the following structural relationships exist:

It is a particular feature of an embodiment of the present invention and is seen in FIG. 24B that attachment of the RNS remover assembly 7010 to the needle shield 7020 of the improved medicament module 7000 is prevented following detachment thereof. Once the RNS remover assembly 7010 is pushed rearwardly with respect to the module housing 7030 and needle shield 7020 in the direction indicated by arrow 7600, in attempt to re-attach the RNS remover assembly 7010 back to the needle shield 7020 of the improved medicament module 7000, it is prevented from being re-attached back to the improved medicament module 7000. The re-attachment of the RNS remover assembly 7010 to the needle shield 7020 of the improved medicament module 7000 is prevented by means of engagement of protrusions 7436 of the RNS remover assembly 7010 with circumferential rim 7212 of the needle shield 7020, and specifically by means of engagement of rearwardly facing angled edges 7438 of protrusions 7436 with recesses 7294 formed in circumferential rim 7212. In this operative orientation, protrusions 7436 are held securely by recesses 7294 and prevent rearward displacement of the RNS remover assembly 7010 relative to needle shield 7020 in the direction indicated by arrow 7600.

It is a further particular feature of an embodiment of the present invention that due to engagement of protrusions 7436 with circumferential rim 7212 of the needle shield 7020, the protrusions 7236 of flexible fingers 7228 of needle shield 7020 are prevented from being inserted into openings 7460 of the RNS remover assembly 7010.

It was previously described in FIGS. 64A-64C of PCT Patent application PCT/IL2016/050929, which is incorporated by reference herein, that medicament module 200/300 without the RNS remover 210 cannot be charged into the automatic injection assembly 100. Similarly, the improved medicament module 7000 cannot be charged into the automatic injection assembly 100 once the RNS remover assembly 7010 is removed therefrom and is prevented to be mounted back on to the improved medicament module 7000, as described hereinabove.

It is a particular feature of an embodiment of the present invention that a gap is formed between the rearwardmost edge surface 7432 of the outer portion 7400 of the RNS remover assembly 7010 and the forward-facing generally symmetric edges 7105 of the module housing 7030, such that the outer portion 7400 of the RNS remover assembly 7010 is forwardly spaced from the module housing 7030 and the user is not able to apply force on the module housing 7030 through the RNS remover assembly 7010. This gap between the RNS remover assembly 7010 and the module housing 7030 is created due to engagement of inwardly-facing protrusions 7436 of the RNS remover assembly 7010 with the circumferential rim 7212 of the needle shield 7020. It is mentioned hereinabove with reference to FIGS. 22A-22D that inwardly directed side protrusions 7190 and 7192 of each of fingers 7116 and 7118 of the module housing 7030 are inserted into respective narrow slots 7231 and 7232 of the needle shield 7020.

It is previously described and illustrated with reference to FIGS. 22A-22D that the rearwardmost edge surface 7432 of the outer portion 7400 of the RNS remover assembly 7010 abuts the forward-facing generally symmetric edges 7105 of the module housing 7030, thus the inwardly directed side protrusions 7190 and 7192 cannot disengage from narrow slots 7231 and 7232 of needle shield 7020 upon application of force on the improved medicament module 7000 in either direction.

In comparison, it is seen specifically in FIGS. 24A and 24B there is a gap between the RNS remover assembly 7010 and the module housing 7030, thus upon application of longitudinal force on the improved medicament module 7000, such as during pushing the improved medicament module 7000 into the automatic injection device 100 during charging, as shown in FIGS. 64A-64C of PCT Patent application PCT/IL2016/050929, axial displacement between the module housing 7030 and the needle shield 7020 is permitted. This axial displacement causes disengagement of fingers 7116 and 7118 of the module housing 7030 from narrow slots 7231 and 7232 of the needle shield 7020 and thus in turn does not allow charging of a used improved medicament module 7000 into automatic injection device 100, as described in detail with reference to FIGS. 64A-64C of PCT Patent application PCT/IL2016/050929.

This invention generally relates to a reusable automatic injection device for parenteral administration of substances (e.g., a medication) to a living organism (human or animal). The administration may be delivered into the subcutaneous tissue.

The invention is further related to, but is not limited to a self-administration of patients with chronic diseases such as rheumatoid arthritis (RA), multiple sclerosis (MS), HIV, and growth hormone deficiency.

It is appreciated that in accordance with an embodiment of the present invention the medicament is enclosed in a pre-filled syringe, but it can alternatively be used with other drug enclosures such as vials or ampoules, where a vial adaptor or an ampoule adaptor is used to reconstitute, mix, or pump the drug into the syringe prior to injection. The pre-filled syringe can be either a conventional one chambered pre-filled syringe with a ready-to-inject liquid form drug, or it can be a multiple-chambered pre-filled syringe.

The reusable automatic injection device provides an automatic needle insertion through the skin, which therefore overcomes the main obstacle in self-administration, i.e., the needle phobia; the user does not see the needle through all the procedure, i.e., before, during and after injection.

It will be appreciated by persons skilled in the art that the present invention is not limited by what has been specifically shown and described hereinabove. Rather the scope of the invention includes both combinations and sub-combinations of features described and shown hereinabove as well as modifications thereof which would occur to persons reading the foregoing description and which are not in the prior art.

What is claimed is:

1. A medicament module, comprising:
a module housing at least partially surrounding a needle shield and arranged along a mutual longitudinal axis therewith, said needle shield has a forward circumferential rim;
an RNS remover assembly having an outer portion and an inner portion, said inner portion is slidable relative said outer portion along said longitudinal axis and wherein said outer portion has at least one longitudinally extending arm formed with a protrusion,
said RNS remover assembly being attached to said needle shield and configured to be detachable from said needle shield and further configured to be prevented from being subsequently re-attachable to said needle shield after detachment thereof, such that when said RNS remover assembly is being pushed forwardly with respect to said needle shield, re-attachment of said RNS remover assembly to said needle shield is prevented by engagement of said protrusion of said outer portion with said circumferential rim of said needle shield.

2. A medicament module according to claim 1, and wherein said module housing has a forward end and a rearward end and at least one finger disposed between said forward end and said rearward end and wherein said finger has at least one side protrusion.

3. A medicament module according to claim 2, and wherein said needle shield has at least one mounting arm formed with a recess.

4. A medicament module according to claim 3, and wherein said at least one mounting arm is also formed with at least one slot, arranged rearwardly of said recess.

5. A medicament module according to claim 4, and wherein said recess is disposed at a forward end of said mounting arm, said recess has a forward tapered surface.

6. A medicament module according to claim 1, and wherein said at least one longitudinally extending arm extends to an edge surface, and wherein said at least one longitudinally extending arm is formed with a protrusion.

7. A medicament module according to claim 6, and wherein said outer portion has at least one rearwardly extending arm, which extends to a rearwardmost edge surface, and wherein said at least one rearwardly extending arm is formed with an inwardly extending protrusion, having a rearwardly-facing angled edge and a forwardly-facing angled edge, both being angled with respect to said longitudinal axis.

8. A medicament module according to claim 7, and wherein said needle shield has at least one mounting arm formed with a recess and at least one slot, arranged rearwardly of said recess, said needle shield also has a forward circumferential rim.

9. A medicament module according to claim 8, and wherein said module housing has a forward end and a rearward end and at least one finger disposed between said forward end and said rearward end and wherein said finger has at least one side protrusion.

10. A medicament module according to claim 9, and wherein in a storage operative orientation, when said RNS remover assembly is attached to said needle shield, said forward end of said module housing abuts said rearwardmost edge surface of said outer portion of said RNS remover assembly.

11. A medicament module according to claim 10, and wherein in said storage operative orientation, relative displacement between said module housing and said needle shield is not permitted due to engagement of said at least one side protrusion of said module housing with said at least one slot of said needle shield.

12. A medicament module according to claim 11, and wherein said protrusion of said outer portion is inserted into said recess of said needle shield in said storage operative orientation.

13. A medicament module according to claim 9, and wherein said RNS remover assembly is configured to be detached from said needle shield when said RNS remover assembly being pulled forwardly relative to said needle shield.

14. A medicament module according to claim 13, and wherein said protrusion of said outer portion is disengaged from said recess of said needle shield when said RNS remover assembly is being detached from said needle shield.

15. A medicament module according to claim 13, and wherein said RNS remover assembly is being detached from said needle shield due to slidable displacement of said rearwardly-facing angled edge of said protrusion of said outer portion relative to said tapered surface of said recess of said needle shield.

* * * * *